United States Patent
Rice et al.

(10) Patent No.: US 6,892,512 B2
(45) Date of Patent: May 17, 2005

(54) AUTOMATED PRESCRIPTION FILLING SYSTEM/METHOD WITH AUTOMATED LABELING AND PACKAGING SYSTEM/METHOD AUTOMATED ORDER CONSOLIDATION SYSTEM/METHOD

(75) Inventors: Dennis Wayne Rice, Flanders, NJ (US); James G. McErlean, Allendale, NJ (US); E. Christian Hess, Flanders, NJ (US); P. Thomas Shupert, Parkton, MD (US); Chih-Jen Leu, East Brunswick, NJ (US); Robert Gregory Howell, Philadelphia, PA (US); Michael Joseph Szesko, Freehold, NJ (US); Andrew P. Booler, Kitchener (CA); Peter Monkhouse, Warrington, PA (US); Douglas W. Walton, Southampton, PA (US); Michael W. G. Bell, Las Vegas, NV (US); Christopher J. Lasher, Ridgewood, NJ (US); Thomas P. Bonkenburg, York, PA (US)

(73) Assignee: Medco Health Solutions, Inc., Franklin Lakes, NJ (US)

( * ) Notice: Subject to any disclaimer, the term of this patent is extended or adjusted under 35 U.S.C. 154(b) by 25 days.

(21) Appl. No.: 10/215,249

(22) Filed: Aug. 9, 2002

(65) Prior Publication Data
US 2004/0065053 A1 Apr. 8, 2004

Related U.S. Application Data
(60) Provisional application No. 60/401,340, filed on Aug. 7, 2002.

(51) Int. Cl.$^7$ .......................... B65B 35/30; B65B 61/20
(52) U.S. Cl. ............................. 53/445; 53/55; 53/495; 53/473; 53/411; 53/168; 53/237; 53/249
(58) Field of Search .......................... 53/55, 495, 493, 53/473, 445, 411, 168, 420, 238, 237, 251, 250, 249, 131.4, 131.2, 500

(56) References Cited

U.S. PATENT DOCUMENTS 3,653,176 A   4/1972   Gess (Continued)

FOREIGN PATENT DOCUMENTS

| CA | 2226379 | 1/1997 |
| EP | 0 328 003 A1 | 8/1989 |

(Continued)

OTHER PUBLICATIONS

Jan. 28, 2004. International Search Report from PCT/US03/24687.

(Continued)

Primary Examiner—Stephen F. Gerrity
Assistant Examiner—Hermant Desai
(74) Attorney, Agent, or Firm—Irah H. Donner; Wilmer Cutler Pickering; Hale and Dorr LLP

(57) ABSTRACT

Computer assisted systems, methods and mediums for filling one or more orders. One embodiment of the present invention is a system that includes an order consolidation station configured to receive at least one bottle containing pills individually counted and/or at least one package containing pharmaceutical products without having been designated for any of the orders when the package was created and/or at least one literature pack optionally including patient specific information. The order consolidation station is further configured to combine automatically the received bottle and/or package and/or literature pack into a container to be sent to a recipient including, for example, mail order pharmacies, wholesalers and/or central fill dealers for subsequent distribution or sale including retailer distribution or sale. The bottle is specifically designated for the order, and the order generally includes at least one prescription for the package.

75 Claims, 38 Drawing Sheets

U.S. PATENT DOCUMENTS

| | | | |
|---|---|---|---|
| 3,703,834 A | | 11/1972 | Beezer |
| 3,933,564 A | | 1/1976 | Jensen |
| 3,939,998 A | | 2/1976 | Soltermann |
| 4,351,679 A | | 9/1982 | Dreher |
| 4,363,685 A | | 12/1982 | White |
| 4,573,852 A | | 3/1986 | Rinfret et al. |
| 4,595,447 A | | 6/1986 | Lindstrom |
| 4,647,333 A | | 3/1987 | Voltmer et al. |
| 4,668,327 A | | 5/1987 | Voltmer et al. |
| 4,835,730 A | | 5/1989 | Shimano et al. |
| 4,944,647 A | | 7/1990 | Oleson et al. |
| 5,208,762 A | * | 5/1993 | Charhut et al. ............ 700/216 |
| 5,298,104 A | | 3/1994 | Absher |
| 5,660,305 A | | 8/1997 | Lasher et al. |
| 5,713,485 A | | 2/1998 | Liff et al. |
| 5,771,657 A | * | 6/1998 | Lasher et al. .................. 53/55 |
| 6,230,927 B1 | * | 5/2001 | Schoonen et al. ............ 221/10 |
| 6,370,841 B1 | | 4/2002 | Chudy et al. |
| 6,413,345 B1 | | 7/2002 | Treleaven |
| RE37,829 E | | 9/2002 | Charhut et al. |
| 6,471,089 B2 | * | 10/2002 | Liff et al. ..................... 221/13 |
| 6,511,569 B1 | | 1/2003 | Nixon et al. |
| 6,580,968 B1 | * | 6/2003 | Yuyama et al. ............ 700/241 |
| 2001/0017817 A1 | | 8/2001 | De La Huerga |

FOREIGN PATENT DOCUMENTS

| | | |
|---|---|---|
| EP | 0 684 130 A2 | 11/1995 |
| EP | 0 292 018 A2 | 11/1998 |
| EP | 0 974 524 A1 | 1/2000 |
| EP | 1 186 285 A2 | 3/2002 |
| GB | 990140 | 4/1965 |
| JP | 063155196 | 11/1994 |
| JP | 08052198 | 2/1996 |
| WO | WO 89/05727 | 6/1989 |
| WO | WO 99/17218 | 4/1999 |
| WO | WO00/34925 | 6/2000 |

OTHER PUBLICATIONS

Nov. 25, 2003. Communication from European Patent Office regarding European Patent Application No. 03005846.5.

Jan. 29, 2004. International Search Report from PCT/US03/24686.

Dec. 2, 2003. International Search Report from PCT/US03/24685.

Nov. 26, 2003. International Search Report from PCT/US03/24688.

* cited by examiner

ALPS OVERALL LAYOUT (3 ALPS SUBSYSTEMS)

SINGLUATE/SCAN TUNNEL/LABEL STATION

FIG. 20 BAGGER

AUTOMATED PRESCRIPTION FILLING SYSTEM/METHOD WITH AUTOMATED LABELING AND PACKAGING SYSTEM/METHOD AUTOMATED ORDER CONSOLIDATION SYSTEM/METHOD

This application claims priority from U.S. Provisional Application No. 60/401,340, filed Aug. 7, 2002, incorporated herein by reference.

FIELD OF THE INVENTION

The present invention generally relates to methods, systems and medium for automatically dispensing and/or packaging of prescriptions and/or prescription orders wherein disparate pharmaceutical packages, e.g., bottles with automatically and/or manually dispensed pills, packages with pharmaceutical products, literature packs that are optionally patient specific, etc., are automatically dispensed and/or combined into packages. The present invention may be used for mail order pharmacies, wholesalers and/or central fill dealers for subsequent distribution or sale including a retailer.

BACKGROUND OF THE INVENTION

In mail service pharmacies and large retail pharmacies, prescription drugs are dispensed in a high volume. For such services, it is known to use an automatic pill dispensing system to carry out the dispensing of the prescription drugs automatically at a rapid rate and to label pill containers which can then be provided to the patient for whom the prescriptions were written.

A known automatic pill dispensing system is described in U.S. Pat. No. 5,771,657 issued to Lasher et al., which is incorporated herein by reference. In the patent, as shown in the schematic illustration of FIG. 1A, orders (e.g., orders to fill prescriptions) are received by a host computer 9 which forwards the orders to a distributed computer system including a central computer called Pharmacy Automation Controller 10 (PAC). PAC maintains an order file of the information about each prescription to be filled in an order including all of the information needed to fill each prescription, prepare a prescription label for each prescription and the information to print literature to go in a shipping container with the prescription or prescriptions. PAC updates the order file to maintain a record of the current status of each prescription being filled as it progresses through the automated system.

PAC 10 controls a set of PAL stations 14 which print prescription bottle labels, apply the prescriptions to prescription bottles, and load the labeled bottles onto bottle carriers, a carrier conveyer system 21 which carries the bottle carriers to different parts of the system, automatic drug dispensing machines 23 which dispense tablets or capsules into the prescription bottles in the bottle carriers as they are carried by the conveyer system 21, bottle cappers 25 which apply caps to the bottles, and OCP stations 29 at which the bottles are unloaded from the carriers and placed in the shipping containers corresponding to the patient orders. The conveyer system 21 carries the bottles in the carriers from the PAL stations through the automatic drug dispensing machines 23 to the bottle cappers 25 and then from the bottle cappers to the OCP stations 29. The conveyer system 21 also carries the empty carriers back to the PAL stations 14. The OCP stations each also have a literature dispensing mechanism, which inserts printed literature into each shipping container with the filled and capped prescription bottles. PAC 10 controls literature printers 31 which print literature for each prescription order and enclose the literature for each prescription order in an envelope, print a bar code that shows through a window in the envelope identifying the prescription order, and then place each envelope on a literature conveyer 34 which carries the envelope from the literature printers 31 to the OCP stations 29.

As shown in FIG. 1B, bottles to be automatically filled with the prescription drugs are introduced to the automated system by hoppers 37 which receive the bottles in bulk form and automatically feed the bottles to unscramblers 39. One of the hoppers 37 and one of the unscramblers 39 will be for large bottles of 160 cc. and the remaining hoppers and unscramblers will be for small bottles of 110 cc. The small bottle size can accommodate a majority of the automatically filled prescriptions. The large bottles are large enough for 91 percent of the prescriptions and are used to fill the prescriptions in that 91 percent which are too large for the small bottles. The remaining 9 percent of the prescriptions which are too large for the large bottles are filled by using multiple bottles. A large bottle and a small bottle will contain a volume required for 97.5 percent of the automatically filled prescriptions. In the unscramblers, the bottles are singulated and oriented so that the bottle opening first faces downward. The bottles are then righted and directed to PAL stations 14 on bottle conveyers 41 and 43, one for large bottles and one for small bottles.

In the above described conventional system, bottles from one order and corresponding literature are combined into one package. However, many orders include prescriptions for non-pill pharmaceutical products. For example, prescriptions may include liquid pharmaceutical packages, boxes and/or pre-packaged bulk bottles. In addition, as noted above, when prescriptions are filled and mailed to patients, the mail package may include literatures relating to the drugs in the package. The conventional systems are not configured to dispense and combine automatically the above-listed disparate pharmaceutical products into packages.

SUMMARY OF THE INVENTION

Computer-assisted methods, systems and mediums of the present invention overcome, among others, the shortcomings of the above-described conventional systems.

The present invention includes a system for filling at least one order that includes one or more prescriptions. The system includes at least one order consolidation station configured to receive at least one bottle containing pills individually counted and/or the at least one package containing pharmaceutical products without having been pre-designated for the at least one order when the at least one package was created. The at least one bottle is specifically designated for the at least one order, and the at least one order includes at least one prescription for the at least one package. The order consolidation station is further configured to combine automatically the received at least one bottle and/or the at least one package to send the combined the at least one bottle and/or the at least one package to a patient for whom the at least one order was written, thereby filling the at least one prescription.

The at least one order consolidation station can be further configured to receive at least one literature pack containing printed literature relating to the at least one order and configured to combine the at least one literature pack with the combined at least one bottle and/or the at least one package.

The system may also include a package storage device having an array of locations and configured to store the at least one package into one of the array of locations. The system can also include a package dispenser configured to identify the one of the array of locations, pick the at least one package from the one of the array of locations and send the at least one package to the order consolidation station.

The system may also include a package storage device having an array of locations and configured to store a plurality of packages into the array of locations and store the at least one package into one of the array of locations. The system can include a package dispenser configured to identify the one of the array of locations, pick the at least one package from the one of the array of locations and send the at least one package to the order consolidation station.

The package dispenser can include a package label printer to print at least one label for the at least one package. The label is printed with patient specific information including instructions by a prescribing doctor to the patient. The package dispenser may further include a label folder and/or manipulator configured to fold and/or manipulate the at least one label into a wrapped label having a sufficiently small footprint to be affixed on the at least one package. The package dispenser can also include an error detection system configured to detect and read the label affixed on the at least one package and configured to reject the at least one package and the label if an incorrect label is affixed thereto.

The system can also include a bottle storage device having an array of locations and configured to store a plurality of bottles into one of the array of locations, and a bottle dispenser configured to identify the one of the array of locations and send the at least one bottle from the one of the array of the locations to the order consolidation station.

The bottle dispenser can also comprise a metal detector configured to detect a present of a metallic substance in the at least one bottle. The bottle dispenser can be further configured to reject the at least one bottle if a metallic substance is detected therein. The bottle dispenser can also include a bottle magazine to receive the at least one bottle belonging to the one of at least one order. The bottle magazine is disposed and configured to release the received at least one bottle into the bag.

In addition, the system can also include a bagger configured to open a bag to receive the at least one bottle and/or the at least one package into the bag. The bagger can also include an address label or internal control label printer configured to print an address of the patient. The bagger can be further configured to affix the address label or internal control label on the bag before the bag is opened.

The present invention also includes a system for filling at least one order. The system may include a bottle handling station configured to store and dispense at least one bottle containing pills individually counted. The at least one bottle is specifically designated for the at least one order. The system can also include a package handling station configured to store and dispense at least one package containing pharmaceutical products without having been pre-designated for the at least one order when the at least one package was created. The at least one order includes at least one prescription for the at least one package. The system can further include an order consolidation station configured to combine the received at least one bottle and/or the at least one package to send the received at least one bottle and the at least one package to a patient for whom the at least one order was written, to thereby fill the one of at least one order and/or prescription.

The system may also include a literature handling station configured to store and dispense at least one literature pack containing printed literature relating to the at least one order. The order consolidation station can be further configured to receive the at least one literature pack and combine the at least one literature pack with the received at least one bottle and/or the at least one package.

The present invention also provides a system for filling a plurality of orders. The system comprises a bottle handling station configured to store a plurality of bottles each containing pills individually counted. Each bottle is specifically designated for one of the plurality of orders. The system can also include a literature handling station configured to store a plurality of literature packs each containing printed literature relating to one of the plurality of orders and configured to determine a sequence in which the literature packs are stored with respect to corresponding orders. The system may also include a computer system configured to monitor the bottle handling and literature handling stations and configured to cause the bottle handling station to dispense the bottles in the sequence in which the literature packs are stored with respect to corresponding orders and/or prescriptions. The system may further include an order consolidation station configured to receive the bottles and the literature packs in the sequence in which the literature packs are stored with respect to corresponding orders and/or prescriptions and configured to combine the bottles and the literature packs belonging to one of the plurality of orders.

The system may also include a package handling station configured to store a plurality of packages containing pharmaceutical products without having been designated for any of the plurality of orders when the plurality of packages is created. The computer system is further configured to monitor the package handling station and cause the package handling station to dispense the packages in the sequence in which the literature packs are stored with respect to corresponding orders. The order consolidation station can be further configured to receive the packages in the sequence in which the literature packs are stored with respect to corresponding orders and/or prescriptions and configured to combine the packages belonging to the one of the plurality of orders with the combined bottles and literature packs.

The computer system can also be configured to detect an error when the bottles are not received by the order consolidation station in the sequence in which the literature packs are stored. The computer system can also be configured to detect an error when the packages are not received by the order consolidation station in the sequence in which the literature packs are stored.

The present invention also provides a method for filling at least one order. The method can include the step of receiving at least one bottle containing pills individually counted and/or the at least one package containing pharmaceutical products without having been pre-designated for the at least one order when the at least one package was created. The at least one bottle is specifically designated for the at least one order, and the at least one order includes at least one prescription for the at least one package. The method may also include the step of automatically combining the received at least one bottle and/or the at least one package to send the at least one bottle and/or the at least one package to a patient for whom the at least one order was written, to thereby fill the one of at least one order.

The method may also include the step of receiving at least one literature pack containing printed literature relating to the at least one order and configured to combine the at least one literature pack with the received at least one bottle and/or the at least one package.

The method can also include the steps of storing the at least one package into one of an array of locations of a package storage device, identifying the one of the array of locations, and picking the at least one package from the one of the array of locations. The method may further include the step of printing at least one label for the at least one package. The label is printed with patient specific information including instructions by a prescribing doctor to the patient. The method can also include the step of folding, configuring or manipulating the at least one label into a sufficiently small footprint to be affixed on the at least one package.

The method may also include the steps of detecting and reading the label affixed on the at least one package, and rejecting the at least one package and the label if an incorrect label is affixed thereto. The method can also include the steps of storing the at least one bottle into one of an array of locations in a bottle storage device, and identifying the one of the array of locations. The method may further comprise the steps of detecting the presence of a metallic substance in the at least one bottle and rejecting the at least one bottle if a metallic substance is detected therein.

The method may also include the step of opening a bag to receive the at least one bottle and/or the at least one package into the bag. The method may also include the steps of printing an address of the patient and affixing the address label on the bag before the bag is opened.

The present invention also provides a method for filling at least one order. The method comprises the step of storing and dispensing at least one bottle containing pills individually counted. The at least one bottle is specifically designated for the at least one order. The method may also include the step of storing and dispensing at least one package containing pharmaceutical products without having been designated for any of the at least one order when the at least one package was created. The at least one order includes at least one prescription for the at least one package. The method can also include the step of combining the received at least one bottle and/or the at least one package to send directly or indirectly using a variety of means, for example, through a retailer, wholesaler, and/or central fill, the at least one bottle and/or the at least one package to a patient for whom the at least one order was written, to thereby fill the one of at least one order.

The method may also include the steps of storing and dispensing at least one literature pack containing printed literature relating to the at least one order and receiving the at least one literature pack and combining the at least one literature pack with the received at least one bottle and/or the at least one package.

The present invention also provides a system for filling at least one order. The system includes at least one order consolidation means for receiving at least one bottle containing pills individually counted and/or the at least one package containing pharmaceutical products without having been pre-designated for the at least one order when the at least one package was created. The at least one bottle is specifically designated for the at least one order, and the at least one order includes at least one prescription for the at least one package. The order consolidation means can be further configured for automatically combining the received at least one bottle and/or the at least one package into a bag to be sent to a patient for whom the at least one order was written, to thereby fill the one of at least one order.

The order consolidation means can be further configured for receiving at least one literature pack containing printed literature relating to the at least one order and combining the at least one literature pack with the received at least one bottle and at least one package.

The system may also include a package storage means, having an array of locations, for storing the at least one package into one of the array of locations and a package dispense means for identifying the one of the array of locations, picking the at least one package from the one of the array of locations and sending the at least one package to the order consolidation means. The package dispense means can also include a package label printer to print at least one label for the at least one package. The label is printed with patient specific information including instructions by a prescribing doctor to the patient. The package dispense means can further include a label folder configured to fold the at least one configured or manipulated label having a sufficiently small footprint to be affixed on the at least one package.

The package dispense means can further include an error detection system configured to detect and read the label affixed on the at least one package and discard the at least one package and the label if an incorrect label is affixed thereto.

The system can also include a bottle storage means, having an array of locations, for storing the at least one bottle into one of the array of locations and a bottle dispense means for identifying the one of the array of locations and sending the at least one bottle from the one of the array of the locations to the order consolidation means.

The bottle dispense means can include a metal detector means for detecting the presence of a metallic substance in the at least one bottle. The bottle dispense means may be further configured for rejecting the at least one bottle if a metallic substance is detected therein.

The bottle dispense means can include a bottle magazine means for receiving the at least one bottle belonging to the one of at least one order. The bottle magazine means is disposed and configured to release all received at least one bottle into the bag.

The system may also include a bagger means for opening the bag to receive the at least one bottle and at least one package into the bag. The bagger means may include an address label printer means for printing an address of the patient. The bagger means can be further configured for affixing the address label on the bag before the bag is opened.

The present invention may also provide a system for filling at least one order. The system may include a bottle handling means for storing and dispensing at least one bottle containing pills individually counted. The at least one bottle is specifically designated for the at least one order. The system may also include a package handling means for storing and dispensing at least one package containing pharmaceutical products without having been designated for any of the at least one order when the at least one package was created. The at least one order may include at least one prescription for the at least one package. The system may also include an order consolidation means for combining the received at least one bottle and at least one package into a bag to be sent to a patient for whom the at least one order was written, to thereby fill the one of at least one order.

The system may also include a literature handling means for storing and dispensing at least one literature pack containing printed literature relating to the at least one order. The order consolidation means can be further configured to receive the at least one literature pack and combining the at least one literature pack with the received at least one bottle and/or the at least one package.

The system can also provide a system for filling a plurality of orders. The system can include a bottle handling means for storing a plurality of bottles each containing pills individually counted. Each bottle and/or bottles is/are specifically designated for one of the plurality of orders. The system may also include a literature handling means for storing a plurality of literature packs each containing printed literature relating to one of the plurality of orders and for determining a sequence in which the literature packs are stored with respect to corresponding orders. The system may also include a computer system configured to monitor the bottle handling and literature handling means and configured to cause the bottle handling means to dispense the bottles in the sequence in which the literature packs are stored with respect to corresponding orders. The system may also include an order consolidation means for receiving the bottles and the literature packs in the sequence in which the literature packs are stored with respect to corresponding orders and for combining the bottles and the literature packs belonging to one of the plurality of orders.

The system may further include a package handling means for storing a plurality of packages containing pharmaceutical products without having been designated for any of the plurality of orders when the plurality of packages is created. The computer system can be further configured to monitor the package handling means and cause the package handling means to dispense the packages in the sequence in which the literature packs are stored with respect to corresponding orders. The order consolidation means can be further configured for receiving the packages in the sequence in which the literature packs are stored with respect to corresponding orders and configured for combining the packages belonging to the one of the plurality of orders with the received bottles and literature packs.

The present invention may also include a bottle storage apparatus. The device comprising a plurality of storage locations, each storage location, for example, having a top side and a bottom side, and a pin disposed on the bottom side of each of the plurality of storage locations, the pin having an open position and a closed position. Other storage location configurations may alternatively be used. The device also comprises a first gantry crane having a means for picking up a bottle and feeding the bottle to one of the plurality of storage locations via the top side thereof. The bottle is held by the one of the plurality of storage locations, for example, when the pin is in the closed position. The system may also include a second gantry crane having a means for moving, for example, one of the pins from the closed position to the open position. The system may also include a computer system coupled to the first and second loading devices (e.g., gantry cranes) and capable of identifying a location of each storage location. The computer system can be configured to instruct the first loading device to pick up one or more bottles belonging to a order and to feed the one or more bottles to one or more of the plurality of storage locations. The computer system can be further configured to instruct the second gantry crane to, for example, move the pins of the one or more of the plurality of storage locations from the close position to the open position when all of the one or more bottles belonging to the order has been fed to the one or more of the plurality of storage locations.

The plurality of storage locations forms a table. The first gantry crane is disposed on a top side of the table and the second gantry crane, robot arm and/or other standard mechanism is disposed on a bottom side of the table.

The invention of present application provides a system of filling a plurality of orders. A pinch belt including a plurality of locations each of which is capable of carrying a pack of printed material belong to a order. A bottle storage table includes a plurality of storage locations to store at least one bottle belonging to the order. A first conveyor line is located to receive the at least one bottle from the bottle storage table and having a moving surface to move the at least one bottle received from the bottle storage table. The system may also include a means for receiving and holding the at least one bottle and a plurality of shelf locations, each shelf location containing at least one package belonging to the order. The system may also include a robot having an end effector to pick the at least one package and a means to release the at least one package and a second conveyor line having a moving surface to move the at least one package received from the robot. The system can also include a robot arm or other standard mechanism having an end effector to pick up the at least one package and a bagger having a set of arms to open and hold a bag. The system can further include a computer system configured to instruct the pinch belt to convey at least one pack of printed material and discharge the at least one pack into the bag, instruct the bottle storage table to release the at least one bottle, instruct the first conveyor line to move the at least one bottle and dispose the at least one bottle into the bag, instruct the robot to pick up the at least one package and release the at least one package onto the second conveyor line, instruct the second conveyor line to move the at least one package, and instruct the robot arm to pick up and dispose the at least one package into the bag.

There has thus been outlined, rather broadly, the features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

Other features of the present invention will be evident to those of ordinary skill, particularly upon consideration of the following detailed description of the preferred embodiments.

Notations and Nomenclature

The detailed descriptions which follow may be presented in terms of program procedures executed on computing or processing systems such as, for example, a stand-alone computing machine, a computer or network of computers. These procedural descriptions and representations are the means used by those skilled in the art to most effectively convey the substance of their work to others skilled in the art.

A procedure is here, and generally, conceived to be a sequence of steps leading to a desired result. These steps are those that may require physical manipulations of physical quantities (e.g., combining various pharmaceutical products into packages). Usually, though not necessarily, these quantities take the form of electrical, optical or magnetic signals capable of being stored, transferred, combined, compared and otherwise manipulated. It proves convenient at times, principally for reasons of common usage, to refer to these signals as bits, values, elements, symbols, characters, terms, numbers, or the like. It should be noted, however, that all of these and similar terms are to be associated with the appropriate physical quantities and are merely convenient labels applied to these quantities.

Further, the manipulations performed are often referred to in terms, such as adding or comparing, which are commonly associated with mental operations performed by a human operator. No such capability of a human operator is necessary, or desirable in most cases, in any of the operations described herein which form part of the present invention; the operations are machine operations. Useful machines for performing the operation of the present invention include general purpose digital computers or similar devices, including, but not limited to, microprocessors.

BRIEF DESCRIPTION OF THE DRAWINGS

The detailed description of the present application showing various distinctive features may be best understood when the detailed description is read in reference to the appended drawing in which.

DETAILED DESCRIPTION OF THE INVENTION

Reference now will be made in detail to the presently preferred embodiments of the invention. Such embodiments are provided by way of explanation of the invention, which is not intended to be limited thereto. In fact, those of ordinary skill in the art may appreciate upon reading the present specification and viewing the present drawings that various modifications and variations can be made.

For example, features illustrated or described as part of one embodiment can be used on other embodiments to yield a still further embodiment. Additionally, certain features may be interchanged with similar devices or features not mentioned yet which perform the same or similar functions. It is therefore intended that such modifications and variations are included within the totality of the present invention.

Figure 2:
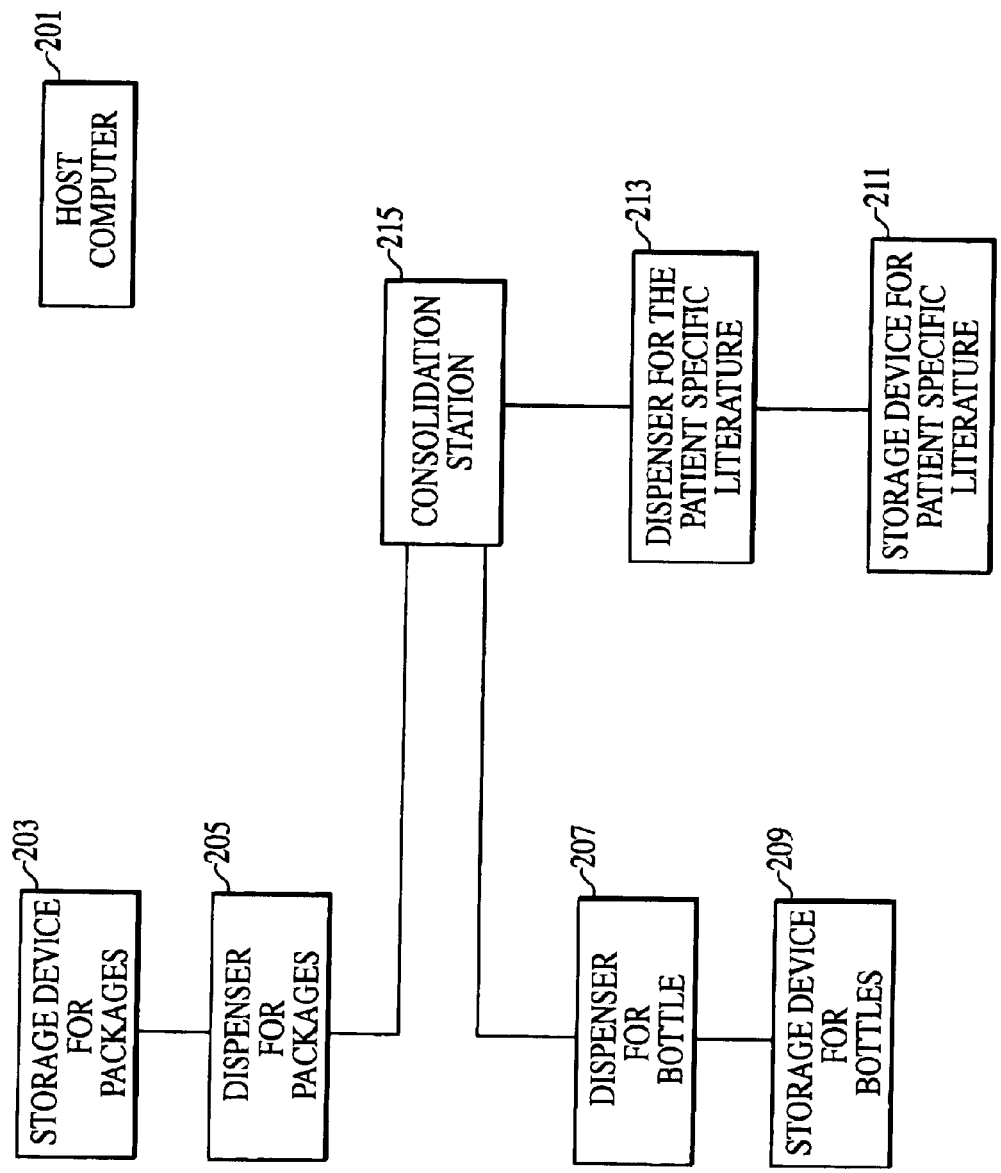
FIG. 2 is a diagram illustrating various components of embodiments of the present invention.

Embodiments of the present invention are directed to dispensing orders that include various pharmaceutical products (e.g., bottles that contain counted pills, packages that include liquid or pre-packaged pharmaceutical products and/or patient specific literatures). In embodiments of the present invention pills also refer to tablets, capsules and other similar terms known in the art. FIG. 2 is a schematic diagram illustrating various components that can be used in embodiments of the present invention. In particular, the components include a storage device for packages 203, dispenser for the packages 205, storage device for bottles filled with counted pills 209, dispenser for the bottled with counted pills 207, storage device for patient specific literatures 211, dispenser for the patient specific literatures 213, consolidation station 215 and host computer 201. Embodiments of the present invention can also include one or more local computers (Not shown in FIG. 2). For instance, each of the components listed above (e.g., the storage device for packages 203, dispenser for the packages 205, storage device for bottles 209, dispenser for bottles 207, storage device for literature packs 211 and dispenser for literature packs 213) can be connected to one or more local computers. The local computers in turn are connected to the host computer 201. In this way, the host computer 201 and local computers are configured to control the various components of the present invention as described below.

A local computer can also function with a standard Programmable Logic Controller (PLC). A PLC typically includes an I/O card to turn on/off a device. Accordingly, when a component is to be controlled by turning it on/off, a PLC can be used. When a large quantity of data is to be exchanged, a local computer can be used.

The storage device for packages 203 stores packages that contain pharmaceutical products. For example, one set of packages may contain a predetermined number of tablets (e.g., 500 tablets) of a certain drug (e.g., Allegra). Another set of example packages may include liquid pharmaceutical products. The packages can be made by original producers of drugs (e.g., Hoechst Marion Roussel). The packages can also be bulk bottles that are filled by any one of many automated (e.g., the ADDS) or manual methods known in the art. These packages can then be shelved so that their locations can be automatically identified. In turn, the dispenser for the packages 205 is configured to automatically identify the location of any package with a certain type of drug, dosage and/or quantity and configured to pick one or more packages from the identified location. In other words, a package contains a pharmaceutical product without having been pre-designated for any specific order when the package was created.

In operation, the command to locate and pick one or more packages is received from the host computer 201. The dispenser for packages can also be connected to its own local computer to perform the necessary functions to locate and pick one or more packages in accordance with the command from the host computer 201. It should be noted that the packages stored in the storage device for packages 203 are not designated for any specific patient. In other words, any package can be picked to fill a order of a patient as long as the type of drug, dosage and/or quantity are matched with the order.

Embodiments of the present invention can also include a standard sensor or a standard counter to indicate when a specific type of package is out of stock in the storage device for packages 203. These sensors or counters can be present at each location (or a substantial number of them). The signals from the sensors or counters can be communicated to, for example, the host computer 201 via the local computer. In turn, the host computer 201 can notify an operator or system to replenish the specific packages and/or stop the process of filling orders that require the specific type of package that are out of stock in the storage device for packages 203. In addition, or optionally, the host computer 201 can send a query to the storage device for packages 203 regarding whether a certain number of certain packages are available to be dispensed. In response, the storage device for packages 203, or in combination with its local computer, can send a response based on information from the sensors and/or counters. Alternatively, sensors may be placed on the robot arm or picking device to provide the similar functionality. In yet another alternative, sensors are not utilized and the system keeps logical control by knowing how many packages have been placed in a channel and how many packages have been removed from the channel.

The dispenser for bottles 207 is configured to receive bottles that contain specific number (e.g., 1–500 or more) of pills for a specific order. For example, one bottle may include 350 tablets of one type of drug for patient A, while another bottle may include 600 tablets of another type of drug for patient B. The bottles can be filled by any automatic dispensing mechanisms known in the art (e.g., the system shown in U.S. Pat. No. 5,771,657). The bottles can also be filled by a person (e.g., a pharmacist) manually counting pills.

If an automatic dispensing system is used, the host computer 201 sends commands to fill bottles with certain number of pills for a certain type of drug. Once they are filled, the bottles are stored in the storage device for bottles 209. In a similar fashion, in a manual system, the dispensing person would receive an instruction to count certain number of tablets for a certain type of drug. The person fills bottles according to the instructions and forwards the bottles to the storage device for bottles 209.

Once the storage device for bottles 209 receives all the bottles necessary to fill an order, the storage device for bottles 209 or in connection with its local computer sends a message to the host computer 201 indicating that the bottle portion of the order has been filled. For example, an order to fill an order may require 1450 pills of a certain type of drug. In this example, the storage device for packages 203 may already have two packages each with 500 pills of the drug. If so, one bottle with 450 pills of the drug is necessary to fill the bottle portion of the order. (If one bottle cannot receive all 450 pills then more than one bottle would become necessary to provide the 450 pills).

Now turning to describe the storage device for literature packs 211, contains literatures to be packaged with specific orders. For example, a set of literature packs for one order may include information relating to each of the prescribed drugs, how often each drug must be taken, billing information, special instructions from the prescribing doctor, insurance information, refilling information and/or general information, for example health or notification of other services. The set of literature packs is then packaged per order and collected in the storage device for literature packs 211. Once the necessary literature packs are created, the storage device for literature packs 211, or in combination with its local computer, can notify the host computer 201 that the literature pack has been printed.

Upon receiving various information from the storage device for packages 203, storage device for bottles 209 and storage device for literature packs 211, the host computer 201 then sends instructions to the dispenser for the packages 205, dispenser for bottles 207 and dispenser for literature packs 213, or to their local computers, to dispense necessary bottle(s), package(s) and literature pack(s) to fill one or more orders. The dispensed bottle(s), package(s) and literature pack(s) are then consolidated by the consolidation station 215 and then sent, distributed or mailed out directly or indirectly to patients associated with the orders. The interactions between the consolidation station 215 and the various components illustrated in FIG. 2 are further described in detail below.

Figure 3:
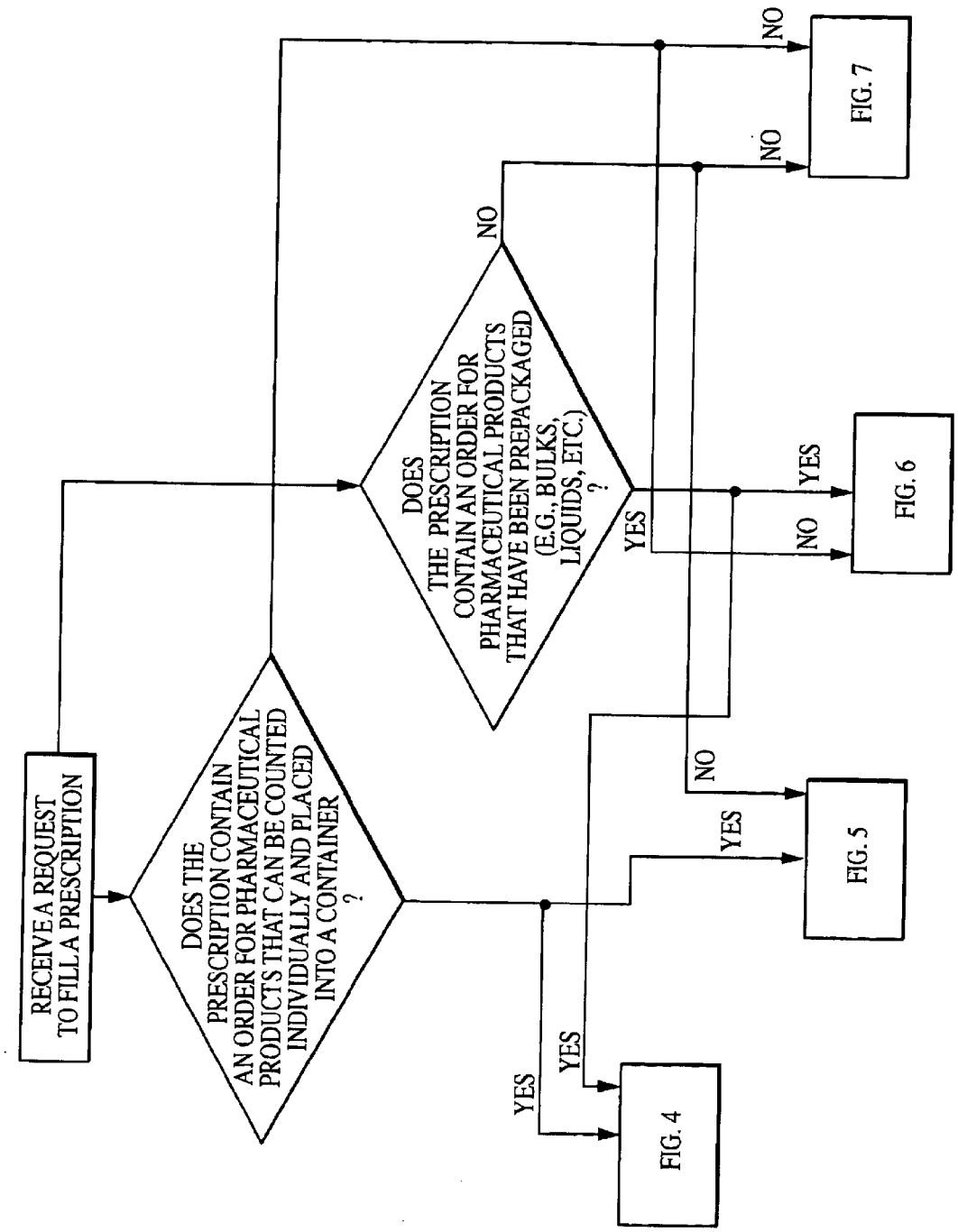
FIG. 3 is a diagram illustrating an initial set of determinations that a host computer is configured to make for embodiments of the present invention.

More specifically, FIG. 3 illustrates example steps taken by the host computer 201 in combination with the local computers and/or the various components. The host computer 201 first receives a request to fill a order. In response, the host computer 201 creates an order number and determines whether the order contains an order that requires bottles to be filled by counting individual tablets and whether the order contains an order that requires packages from the storage device for bottles 209. Depending upon the answers to the above two questions the host computer 201 conducts a number of different sets of steps.

Figure 4:
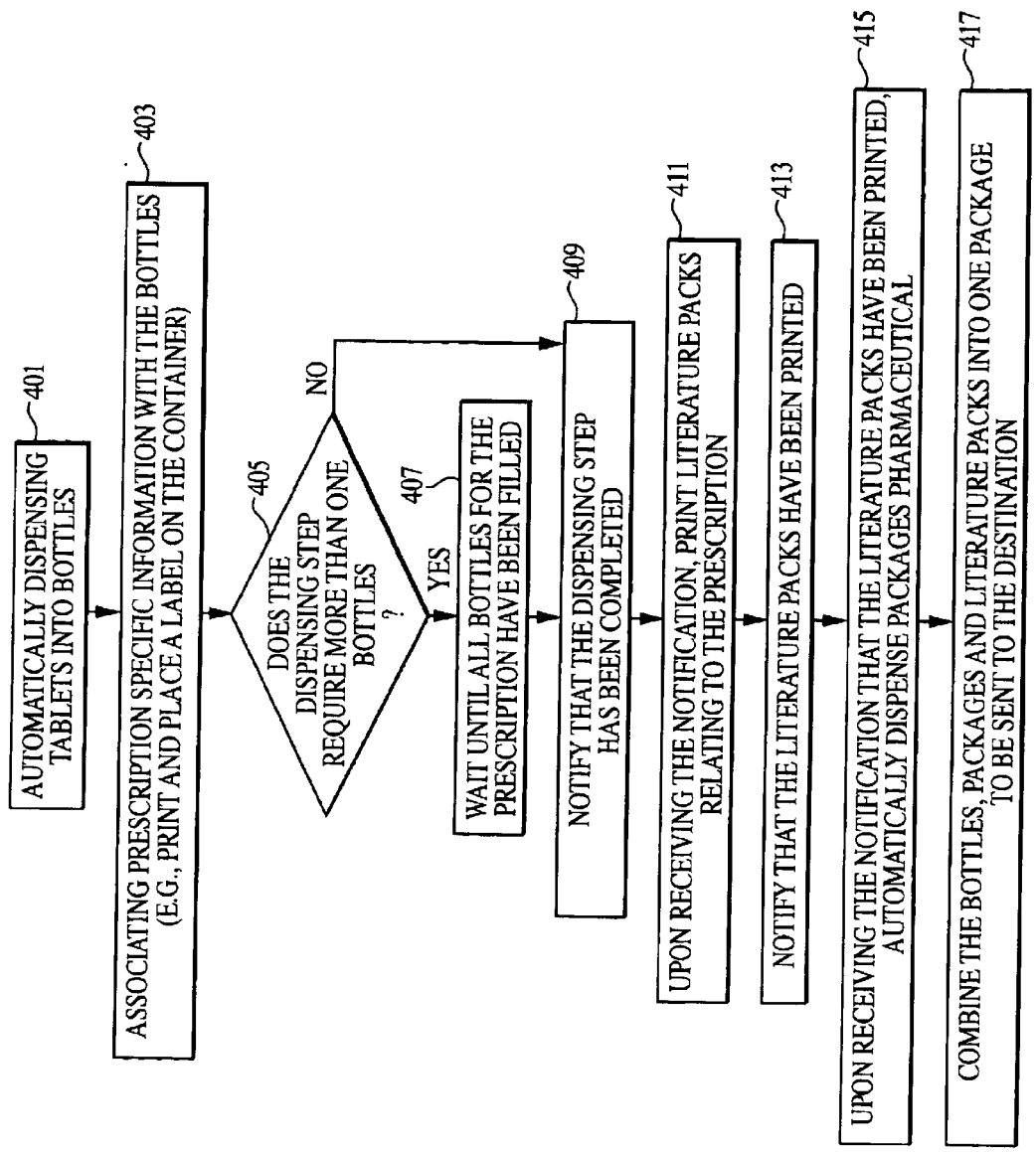
FIG. 4 is a diagram illustrating various steps performed by embodiments of the present invention.
Figure 5:
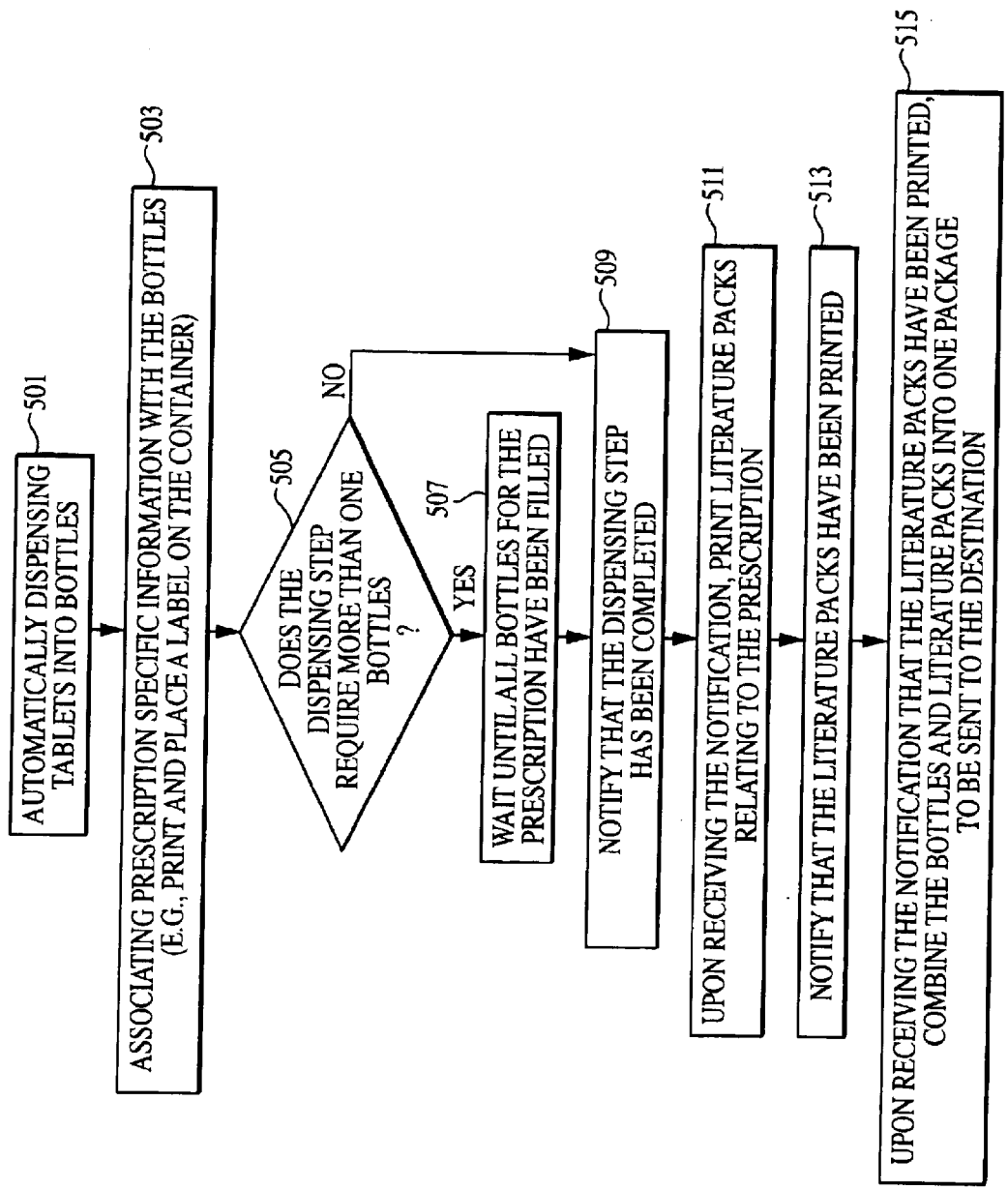
FIG. 5 is a diagram illustrating various steps performed by embodiments of the present invention.
Figure 6:
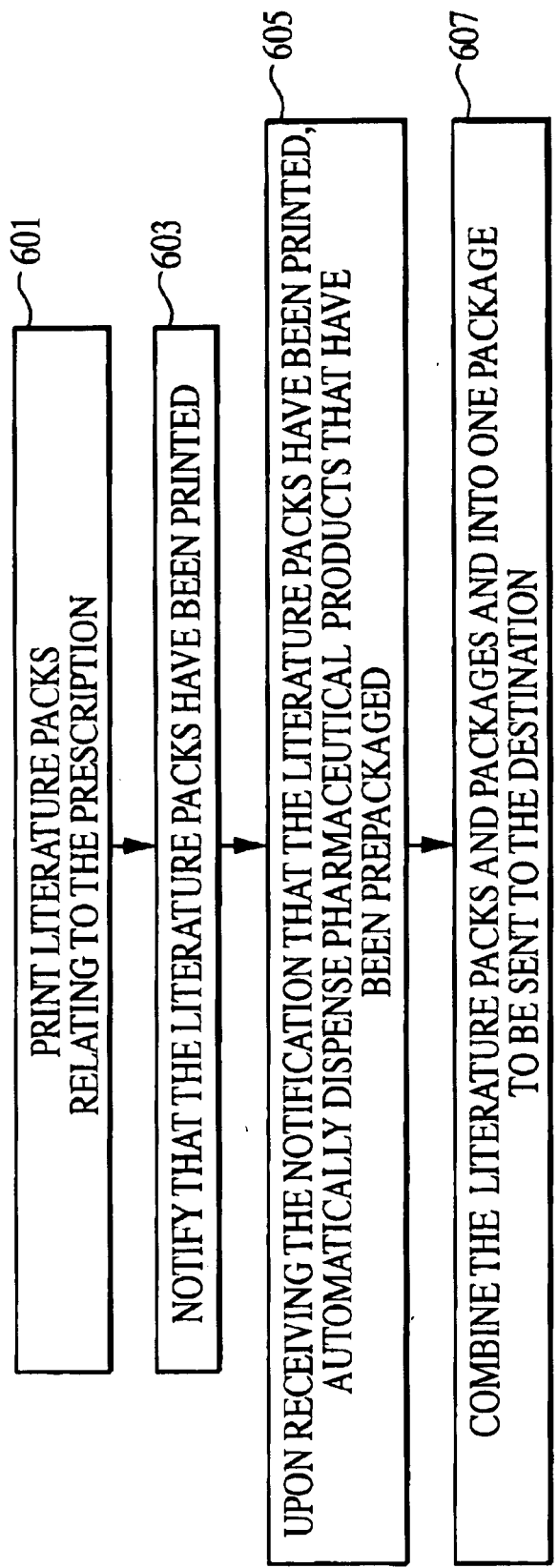
FIG. 6 is a diagram illustrating various steps performed by embodiments of the present invention.
Figure 7:
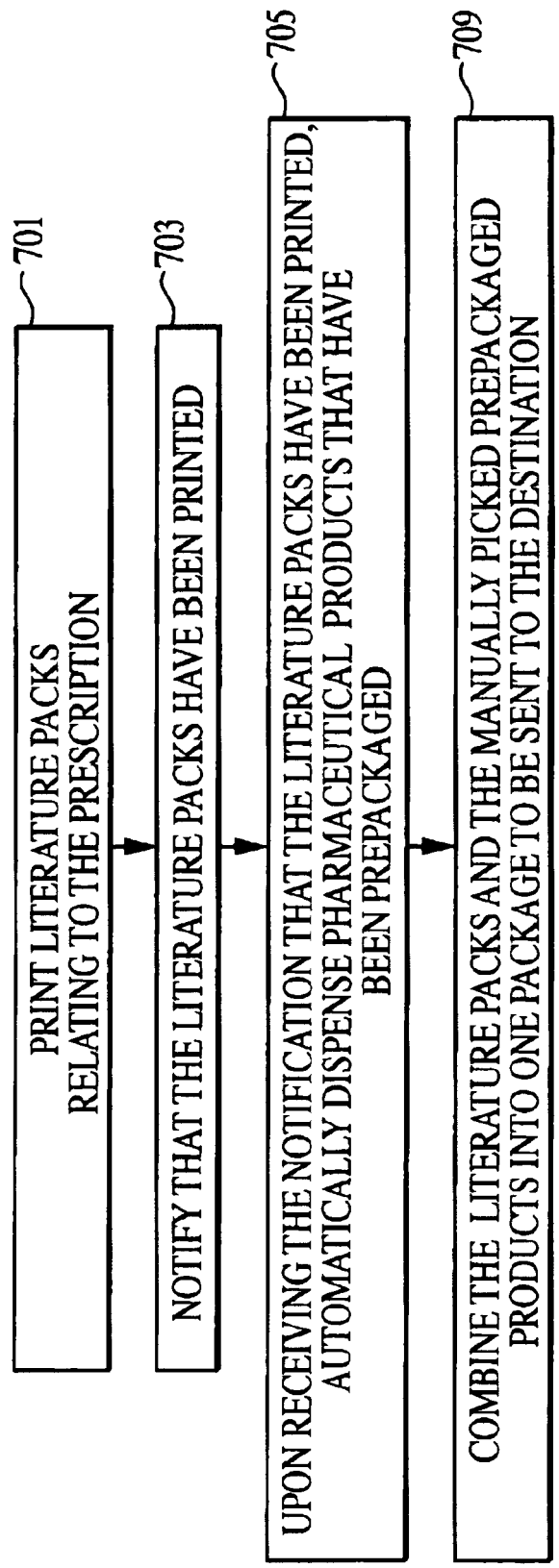
FIG. 7 is a diagram illustrating various steps performed by embodiments of the present invention.

If the order requires both one or more bottles from the storage device for bottles 209 and one or more packages from the storage device for packages 203, then the steps shown in FIG. 4 are executed. If the order requires one or more bottles from the storage device for bottles 209 but does not require any packages from the storage device for packages 203, then the steps shown in FIG. 5 are executed. If the order requires no bottles from the storage device for bottles 209 but requires one or more packages from storage device for packages 203, then the steps shown in FIG. 6 are executed. If the order requires no bottles from the storage device for bottles 209 and no packages from the storage device for packages 203, then the steps shown in FIG. 7 are executed.

Referring to FIG. 4, there is shown a set of steps that can be performed by the host computer 201, in combination with various other components illustrated in FIG. 2 and their local computers when both bottle(s) from the storage device for bottles 209 and package(s) from the storage device for packages 203 are required to be filled for a order. In the manual counting system, an instruction can be printed or shown on an operator's computer monitor to count and fill a specific drug. In the automated system, the host computer 201 can send a set of commands to cause a drug dispenser to count and fill a specific drug, thereby performing the step of automatically dispensing tablets into bottles (step 401).

Whether the manual system and/or the automated system is used, label(s) are prepared and printed to be affixed on the surface of the bottles, thereby performing the step of associating order specific information with the bottles (step 403). The label can be affixed on the caps, sides and/or bottom sides of the bottles as long as they can be located in the later processing steps. The printed labels can contain various information. At minimum, it can contain machine readable (e.g., barcodes) and/or human readable codes/texts so the bottles can be matched to the order numbers in the later processing steps. In addition, the labels can contain information relating to the patient, the drug or any other pertinent information or any combination thereof. One label or a set of labels can be printed and affixed on each bottle. The labels can be printed before, after and/or while the bottles are filled. If the labels are printed before or after the bottles are filled, then printed labels or the bottles need to be queued to be matched with correct bottles or labels, respectively. It should be noted that the information can be printed on the bottles directly and that the information can be alternatively contained in a unique identifier (e.g., radio tags).

As noted above, in filling some orders, more than one bottle may be required. Accordingly, the host computer 201 and/or the local computer determines how many bottles are required. If more than one bottle is required, a notification that the bottles are filled is sent after all the bottles have been filled (steps 405, 407, and 409). If only one bottle is required, a notification is sent as soon as the one bottle is filled (steps 405 and 409). The bottles with the labels affixed thereon are then sent and stored in the storage device for bottles 209. Upon receiving the notification, the host computer 201 and/or a local computer causes corresponding literature pack(s) to be printed (step 411). In some embodiments before, after and/or while the bottles are filled, the host computer 201 can cause literature pack(s) relating to the order to be printed. Once the literature pack(s) is printed, they can be sent and stored in the storage device for literature packs 211.

When the printing literature packs step is completed, a notification is sent to the host computer 201 and/or local computer (step 415). Upon receiving the notification that the literature packs have been printed, the host computer 201 and/or local computers cause packages required to fill the order to be automatically dispensed from dispenser for the packages 205 (steps 415).

With respect to the packages in the storage device for packages 203, as noted above, the host computer 201 can determine if the necessary packages are stocked in the storage device for packages 203. If not, then the host computer 201 can cause the necessary packages to be stocked in the storage device for packages 203 (either manually or automatically).

Although the steps illustrated in FIG. 4 can be performed in a sequence, such a sequence is not required in the present invention. For instance, the step of printing literature packs (step 411) can be performed before other steps. In another example, the step of filling bottles (steps 405, 407, 409) can be performed before other steps. It should be noted that determining which of the steps are performed before other steps can be an engineering design choice. In one instance, if the step of printing literature packs takes the longest time compared with other steps, then the printing step may be started the first. In another instance, if the step of filling bottle(s) takes the longest time compared with other steps, then the filling bottle(s) step may be started the first before other steps.

Now turning back to FIG. 4, once the host computer 201 receives notifications from the storage device for literature packs 211, storage device for bottles 209 and storage device for packages 203 that the respective literature(s), bottle(s) and package(s) for a order have been received and stored, then the host computer 201 causes the dispenser for literature packs 213, dispenser for bottles 207 and dispenser for the packages 205 to dispense and send the items to the consolidation station 215. The consolidation station 215, upon receiving the literature(s), bottle(s) and package(s), combines them into one or more bags (step 417). If the received packages completely fill a order, then the one or more bags can be sealed and a mailing label or internal control label can be affixed on each bag. If the received packages do not completely fill a order and require more packages to be put into the one or more bags, then those bags are sent over to a station where the remaining packages can be put into the bags or joined to the order.

In some embodiments of the present invention, the dispenser for literature packs 213, dispenser for bottles 207 and dispenser for the packages 205 can be configured to dispense literatures) bottle(s) and package(s) to fill one order at a time. In particular, the dispenser for literature packs 213 dispenses one set of literature(s) to fill one order for one patient, the dispenser for bottles 207 dispenses one set of bottles to fill the one order, the dispenser for the packages 205 dispenses one set of packages to fill the one order. In such embodiments, the consolidation station 215 is configured to receive the packages and put them into bags to be mailed or sent over to the next process stations.

In other embodiments of the present invention more than one (e.g., many tens of thousands) of orders can be filled continuously. In such embodiments, a batch of literature packs for a number of orders can be printed and queued in the storage device for literature packs 211. In this embodiment, the sequence in which the literature packs are queued can be used in determining which order's bottle(s) and package(s) are filled first. For instance, assume the literature packs queued in the dispenser for literature packs 213 are in the following sequence: Order A, Order B, Order C and so on. If so, the host computer 201 causes the bottle(s) for Order A be filled first. As soon as the bottle(s) are filled, the host computer 201 then can cause the dispenser for bottles 207 to dispense the bottle(s) for Order A to be dispensed and sent over to consolidation station 215, while causing the dispenser for literature packs 213 to dispense and send the literature pack for Order A be dispensed and sent over to the consolidation station 215. The host computer 201 also causes the same for the packages to dispensed by the dispenser for the packages 205. The consolidation station 215 then combines the received packages.

In yet other embodiments of the present invention, a batch of bottles for a number of orders can be queued in the dispenser for bottles 207. In such embodiments, the sequence in which the bottles are queued can be used in determining which order's literature(s) and package(s) are filled first in a similar manner as described above. Embodiments in which a batch of packages in the dispenser for the packages 205 that determines the sequence of dispensing are also contemplated within this invention.

Referring to FIG. 5, there is shown a set of steps that can be performed by the host computer 201, in combination with various other devices/components illustrated in FIG. 2 and their local computers when bottles from the storage device for bottles 209 but no package(s) from the storage device for packages 203 are required to fill orders. As shown in FIG. 5, most of the steps are similar to the steps shown in FIG. 4 but no steps to dispense packages are included.

In FIG. 6, there is shown a set of steps that can be performed by the host computer 201, in combination with various other devices/components illustrated in FIG. 2 and their local computers when package(s) from the storage device for packages 203 but no bottle from the storage device for bottles 209 are required to be filled. As shown in FIG. 6, most of the steps are similar to the steps shown in FIG. 4 but no steps to dispense bottles are included.

Referring to FIG. 7, there is shown a set of steps that can be performed by the host computer 201, in combination with various other devices/components illustrated in FIG. 2 and their local computers when only manually picked packages are required to fill orders. Examples of manually picked packages are oddly shaped boxes, large boxes, products packaged in plastic bags, manual assistance, etc. These packages cannot be stocked in the storage device for packages 203 because of their odd shapes or because of possible failures. As shown in FIG. 7, literature packs for the orders are printed (step 701). After one or a batch of the literature packs have been printed, the host computer 201 is notified that all packs have been printed (steps 703 and 705). Upon receiving the notification, the host computer 201 sends a set of instructions to an operator to fill the orders by manually counting the required packages. It should be noted that the steps of manually picking packages can also be included in the steps illustrated in FIGS. 4–6.

Figure 8:
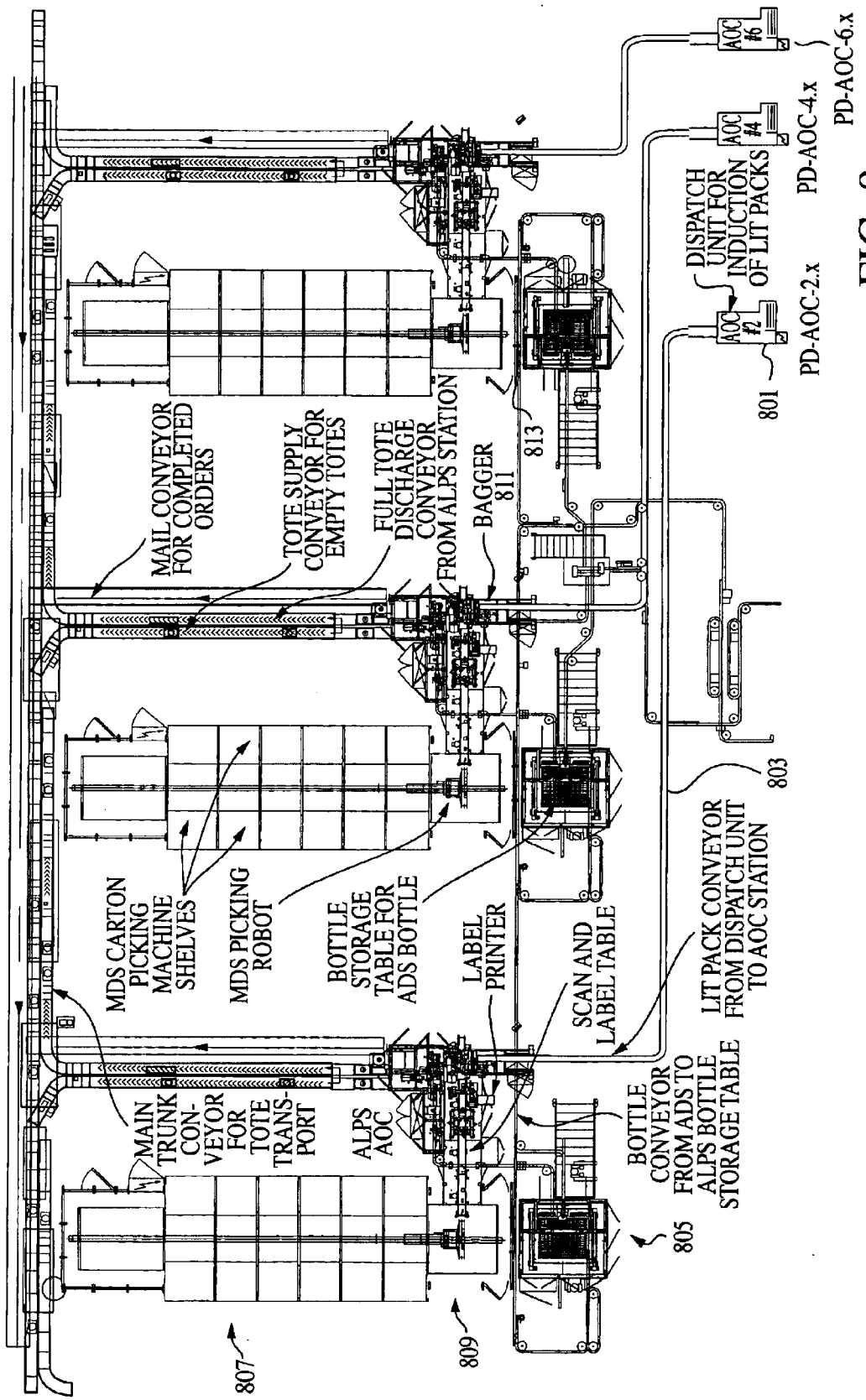
FIG. 8 is a diagram illustrating various example components of embodiments of the present invention.

Now turning to describe details of the various components shown in FIG. 2, FIG. 8 illustrates an overall plant layout of an example embodiment of the present invention. In the example embodiment, the storage device for literature packs 211 is a dispatch unit 801, the dispenser for literature packs 213 is a conveyor belt 803 (e.g., a pinch belt), the storage device for bottles 209 is a bottle storage table 805, the dispenser for bottles 207 is a mechanism that releases bottles queued in the bottle storage table 805, the storage device for packages 203 is a bank of shelves 807, the dispenser for the packages 205 is a standard picking robot 809, and the consolidation station 215 is an order consolidation station 811 including a bagger 813.

These various components can be provided in an assembly line configuration. As shown in FIG. 8, three sets of each component/system can be provided. For instance, the order consolidation station 813 receives literature packs from the dispatch unit 801 via the conveyor belt 803, receives bottles from the bottle storage table 805 and receives the packages from the picking robot 809. The dispatch unit 801 includes a scanner to read the barcodes on the literature packs. The dispatch unit 801 then mounts the literature packs on the belt 803. It should be noted that, although FIG. 8 illustrates only three sets of components, the present invention is not limited to the described number of sets of components. It follows that the present invention may include one to as many sets of the components required to fill orders as they may be received. In one alternative embodiment, a bottle storage table is not used. In another alternative embodiment, more than one AOC and/or bottle storage table may be used. In other alternative embodiments of the invention, manual intervention and/or manual processes may be substituted for one or more components.

Figure 9A:
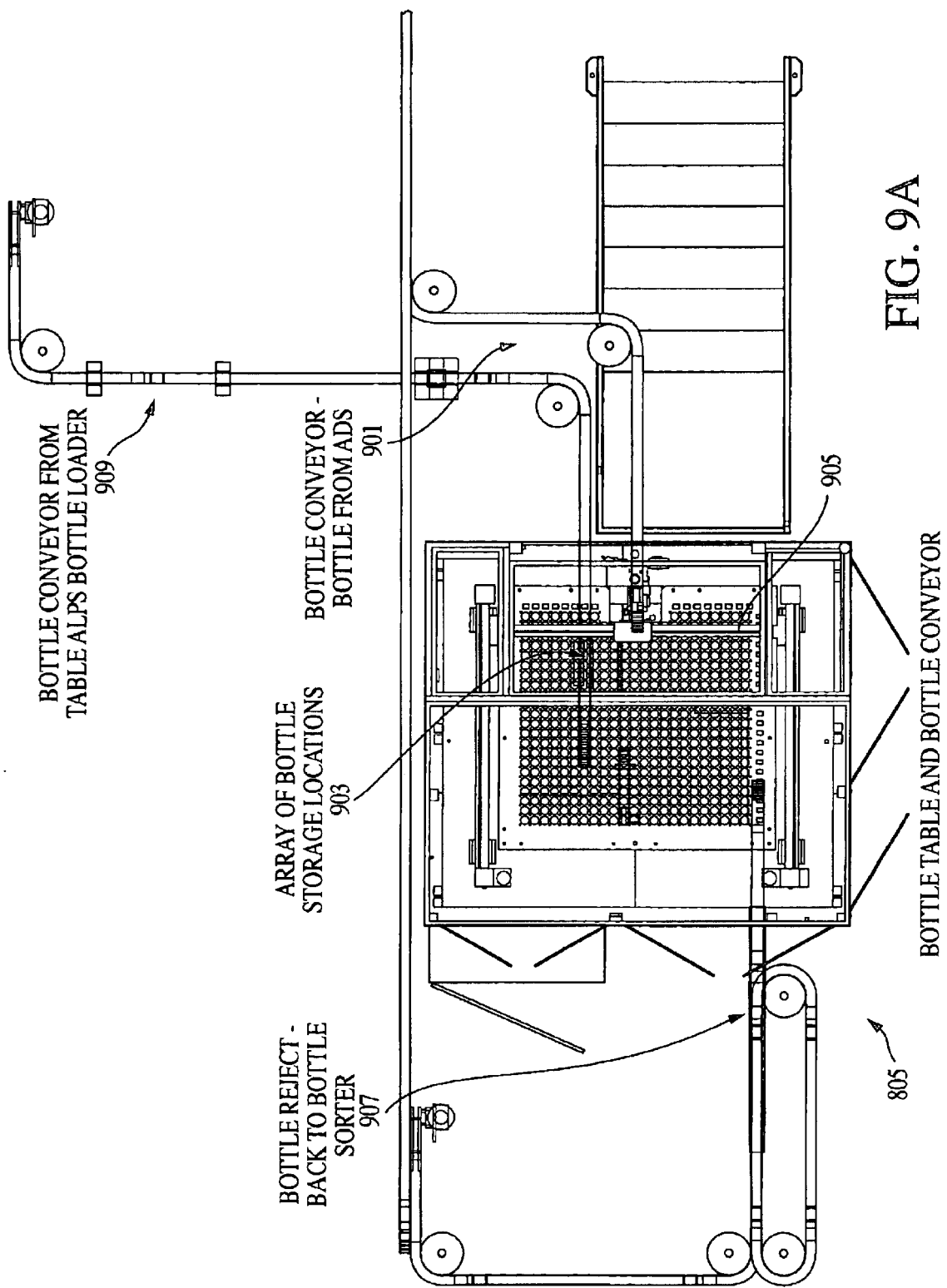
FIGS. 9A–9C are diagrams illustrating an example bottle storage table of embodiments of the present invention.

FIG. 9A illustrates a top view of an example of the bottle storage table 805 and its assembly that includes a bottle conveyor belt 901, an array of bottle storage locations 903, a standard gantry crane 905, a reject conveyor belt 907 and a bottle conveyor belt 909 to feed bottles from the bottle storage table 805 to the order consolidation station. In this example, the bottle storage table 805 receives bottles filled by an automated/manual process as described above in connection with FIG. 2. The labels on the bottles can be scanned to identify its order number. The order number can be barcodes that the host computer 201, or in combination with a local computer, can match to a specific order number. If no match can be made or if any other inconsistencies are detected, the bottle is rejected and sent to a quality assurance station via the bottle reject conveyor belt 907.

Once bottles arrive at the bottle storage table 805, the standard gantry crane 905 picks up the bottles and places them into one of an array of bottle storage locations 903. The gantry crane 905 is known in the art. Examples of such devices include 5126-620 Load to Storage H-BOT, ATS Standard Products, 30529-01370-1350-BV, H-BOT, and 5126-640 Unload from storage H-BOT, ATS Standard Products, 305290-1370-1350-BV, H-BOT, for example, as described in Canadian Patent Application No. 2,226,379, incorporated herein by reference. The local computer can determine which location to put each bottle and instruct the crane 905. The location information is then matched and stored into the local computer along with a corresponding order number. In some embodiments, each location may hold only one bottle. In other embodiments, each location may hold more than one bottle (e.g., four) belonging to the same order. Whether the locations can hold one bottle only or more than one bottle, the local computer is configured to store their corresponding order numbers. Accordingly, when the local computer is instructed to release all the bottles belonging to one order, they can all be located. When one or more locations are identified as having bottles to be released, the bottles in those locations can be then picked up by the crane 905. FIGS. B–C show different perspective view of the bottle storage table.

Figure 9B:
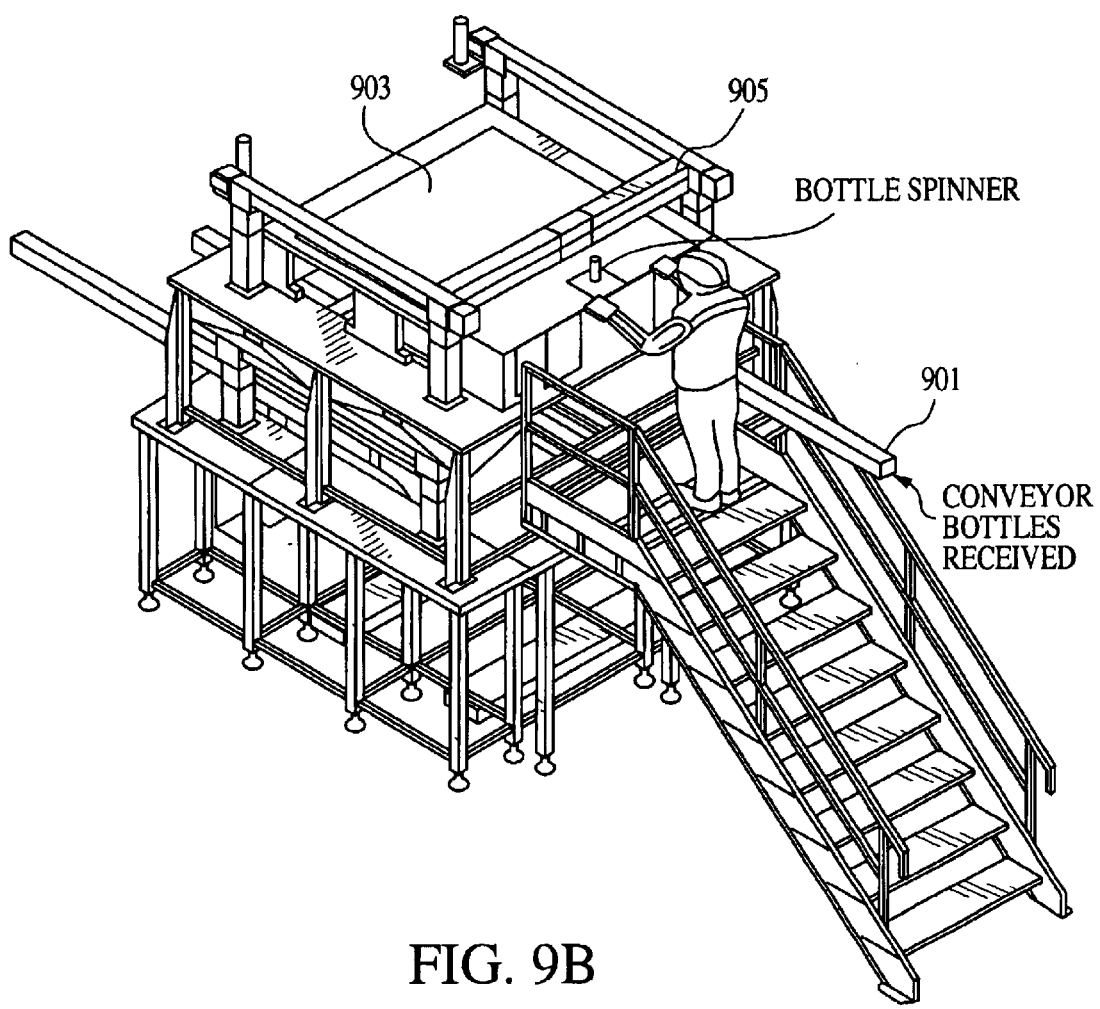
Figure 9C:
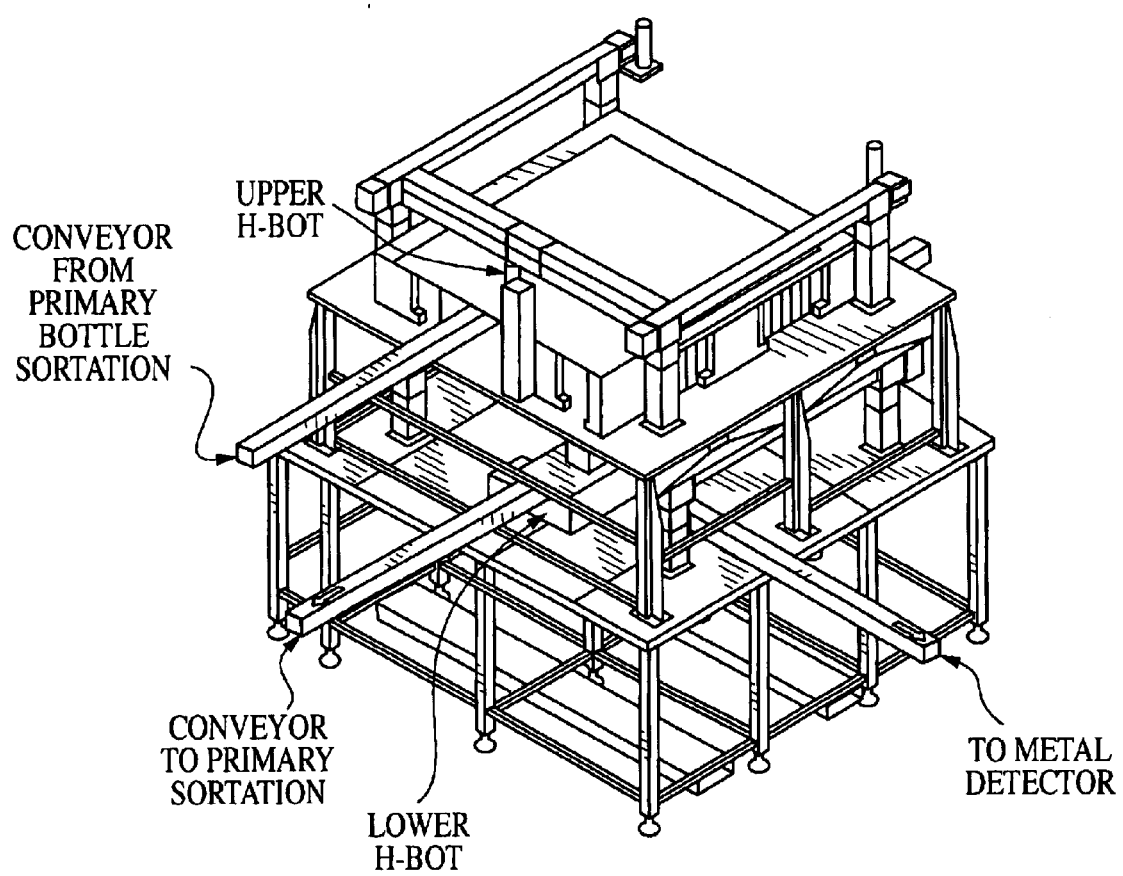
Figure 10:
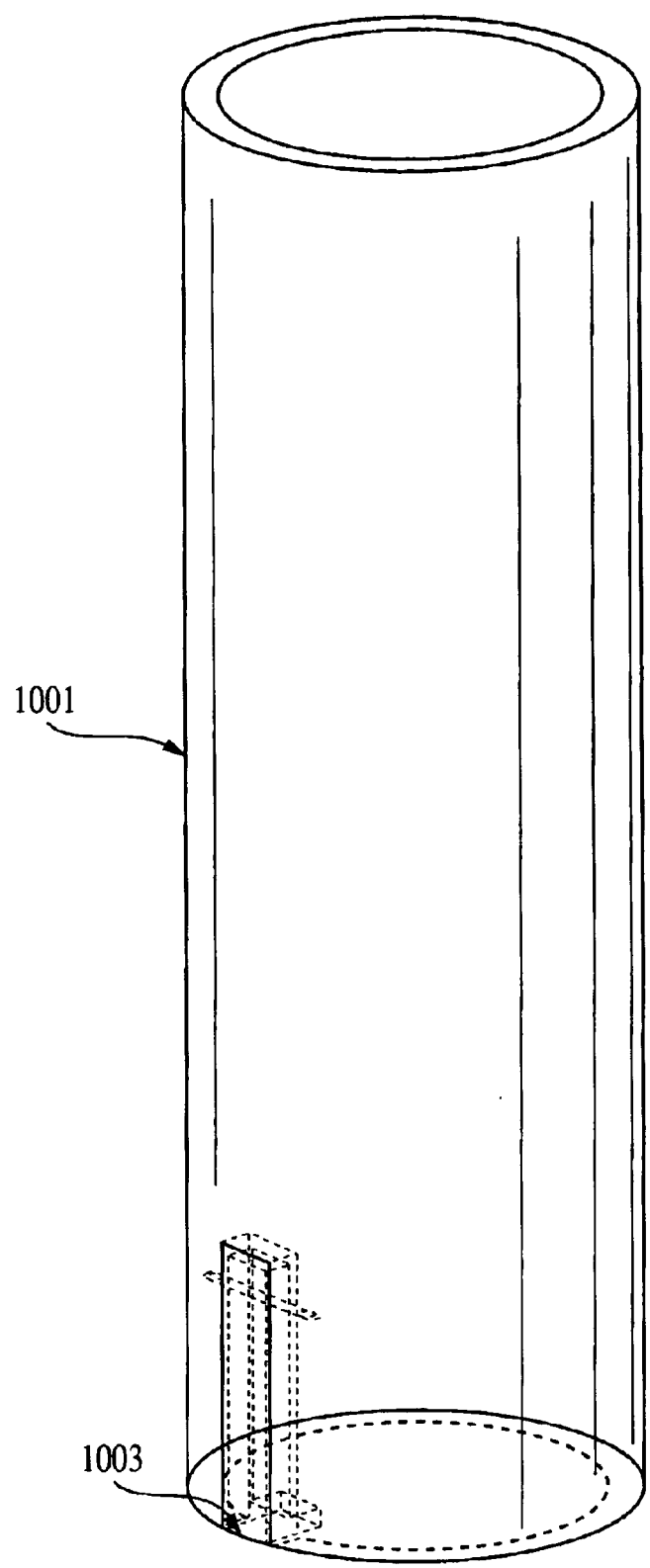
FIG. 10 is a diagram illustrating a tube structure of the example bottle storage table of embodiments of the present invention.

In some embodiments, each storage location is in the form of a tube structure 1001 with a pin switch 1003 near its bottom opening (as shown in FIG. 10). In these embodiments, the tube 1001 structure is configured to receive the bottles via its top opening and hold them therein supported by the pin switch 1003. When the bottles in the tube structure are to be sent over to the order consolidation station 811, the pin 1003 is opened by another gantry crane (part of which is shown in FIGS. 9B–C). When the pin 1003 is opened, the bottles stored in the tube structure 1001 (belong to the same order) slide down through the bottom opening of the tube structure 1001. The bottles are then collected and sent over to the order consolidation station 811 via the bottle conveyor 909.

In the example shown in FIG. 9A, the bottle storage table 805 has a two-dimensional array of storage locations. It should be noted that the bottle storage table 805 can have a one-dimensional array of locations or any other shape of array of locations as long as each location can be identified by the local computer.

Figure 11:
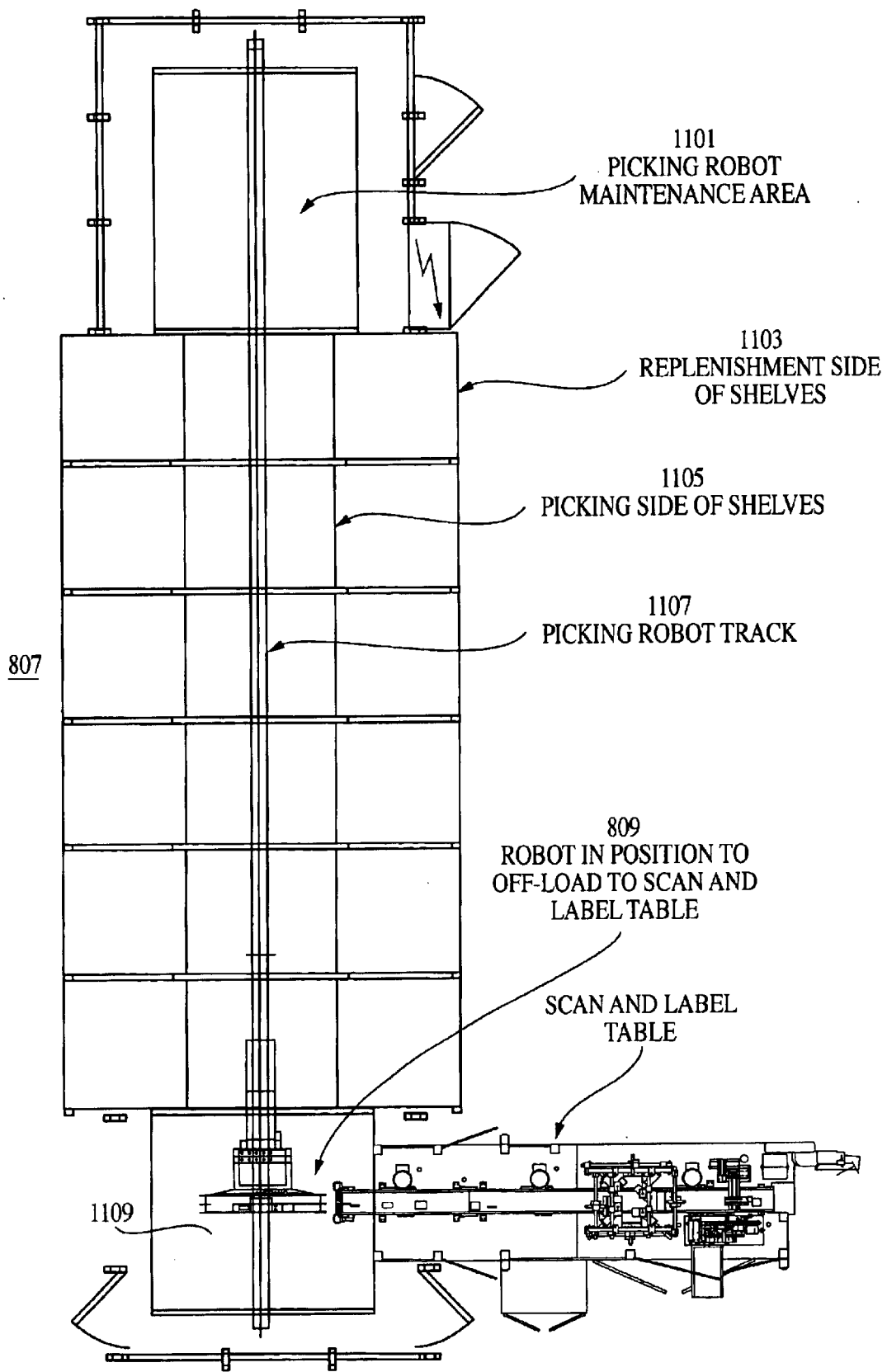
FIG. 11 is a diagram illustrating an example storage device and dispenser for packages of embodiments of the present invention.

Now referring to FIG. 11, there is shown a more detailed example of the storage device for packages 203. In this example, the storage device for packages 203 includes a number of shelves 807 to store various packages to be dispensed, a picking robot maintenance area 1101, a picking robot track and the picking robot 809, such as the MDS picker MODEL-MDS01 manufactured by KNAPP Logistics & Automation, 659 Henderson Drive, Suite I, Catersville, Ga. 30120 U.S.A. and/or Knapp Logistik Automation Ges. m. b. H., Günter-Knapp Str. 5-7 A-8075 Hart bei Graz, Osterrich/Austria. In this example embodiment, the shelves are divided into an array of identifiable locations. Each shelving location has a replenishing side 1103 and picking side 1105. One type of package is fed into each shelving location from its replenishing side 1103 and picked up by the picking robot 809 from the picking side 1105. The shelves are optionally arranged so that the replenishing side 1103 is vertically higher than the picking side 1105. This allows the packages to slide 211 down to the picking side 1105 from the replenishing side 1103.

The locations are stored in a local computer of the storage device for packages 203. The shelf locations can be in a two-dimensional array. In such an embodiment, the picking robot grabbing mechanism 1109 is mounted on an elevator to move up/down/forward/backward. It should be noted that the shelves 807 can also be in one-dimensional array or any other shaped arrays as long as its local computer can identify each individual shelf location. Furthermore, the shelves 807 can be located on two sides of the picking robot 809. Accordingly, the picking robot 809 is configured to pick up packages from both sides thereof. It should also be noted that three-sided, oval shaped, semi-circular shaped shelf formations and/or corresponding picking robots are also contemplated within embodiments of the present invention.

When in operation, the local computer receives instructions from the host computer 201 that include information relating to the quantity and type of drugs to be dispensed from the storage device for packages 203. The local computer then commands the picking robot 809 to traverse on the track 1107 to the location where the package for one type of drug requested is located. The picking robot 809 then picks up the requested quantity of the packages (using its grabbing mechanism or end effector 1109, for example, a pair of fingers) and so on until the request is filled. The request can be filled in a certain sequence parallel, and/or in a random fashion. The picking robot 809 can also have sufficient space to temporarily store all the requested packages to fill the request. In some embodiments, the picking robot 809 is configured to have only limited space to temporarily store the packages. In such embodiments, the local computer is configured to calculate the maximum number of packages (based on information of the foot print sizes of each packages) that can be fit on the limited space. The local computer then commands the picking robot 809 to pick up only the maximum number of packages per load. In an alternative embodiment, the picking robot can be replaced with an A-frame or other picking methods, including manual methods. Alternative control structures or architectures may be used with respect to the local and host computers. For example, in an alternative embodiment, the host computer or other central computer may perform one or more of the functions of the local computer.

Once the packages are picked up, the picking robot 809 traverses to the package disposing location to unload the picked packages. The picking robot 809 can be placed into the picking robot maintenance area 1101 for regularly scheduled maintenance.

Figure 12:
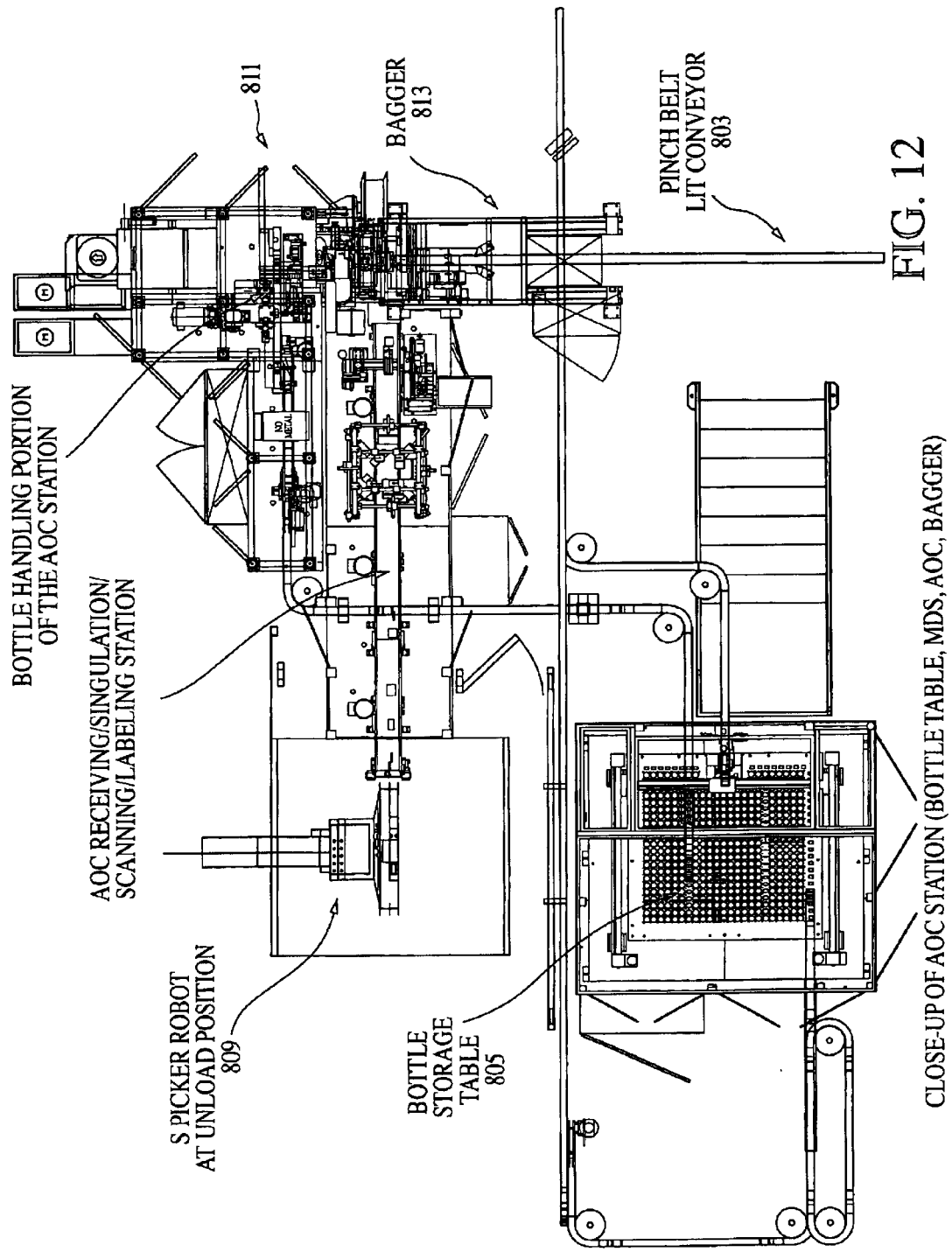
FIG. 12 is a diagram illustrating an example consolidation station and its associated components of embodiments of the present invention.
Figure 13:
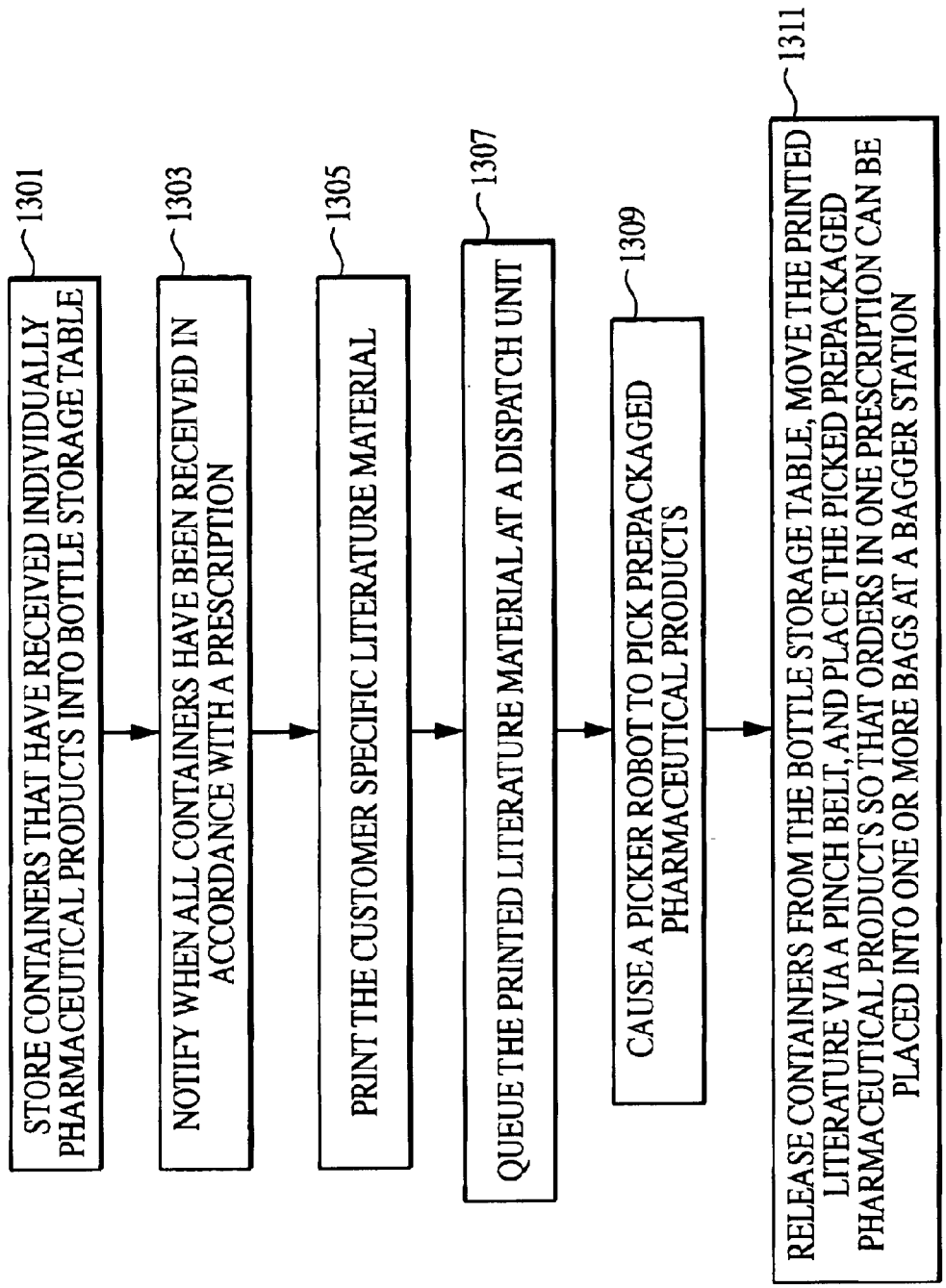
FIG. 13 is a diagram illustrating the steps performed by the consolidation station and its associated components of embodiments of the present invention.

FIGS. 12 and 13 show certain components of the example embodiment shown in FIGS. 9–11 and operations thereof. More specifically, FIG. 12 illustrates the bottle storage table 805 for the bottles, the picking robot 809 and the conveyor belt 803 for the literature packs. The bottles, packages and literature packs are combined in the order consolidation station 811 and put into one or more bags at the bagger 813. In operation, bottles filled with counted pills are stored into the bottle storage table 805 (step 1301). When a complete set of bottles is received by the bottle storage table 805, its local computer notifies the host computer 201 that all the bottles for a particular order have been received (step 1303). In response, the host computer 201 causes literature packs for the order to be printed (step 1305) and sent to the dispatch unit (either in a batch or individually) (step 1307). When the literature packs are received, they are organized such that literature packs for one order are next to each other. The dispatch unit 801 also determines the sequence of orders that the literature packs are received by reading identification codes affixed (or printed) on the literature packs. The dispatch unit 801 then sends the literature packs, as they are received and sequenced, to the order consolidation station 811 via the conveyor belt 803. The dispatch unit 801 also notifies the host computer 201 the sequence of literature packs.

Upon receiving the information from the dispatch unit 801, the host computer 201 then instructs the bottle storage table 805 to release corresponding bottles and the picking robot 809 to pick corresponding packages of the order (steps to 1309 and 1311). The example embodiment is further configured such that the bottles, packages and literature packs all arrive at the bagger 803 simultaneously for each order, although the bagger 803 can optionally receive them at different times in storage locations for later bagging. This configuration allows the bagger 803 to put the bottles, packages, and literature packs into one or more bags automatically.

Figure 14:
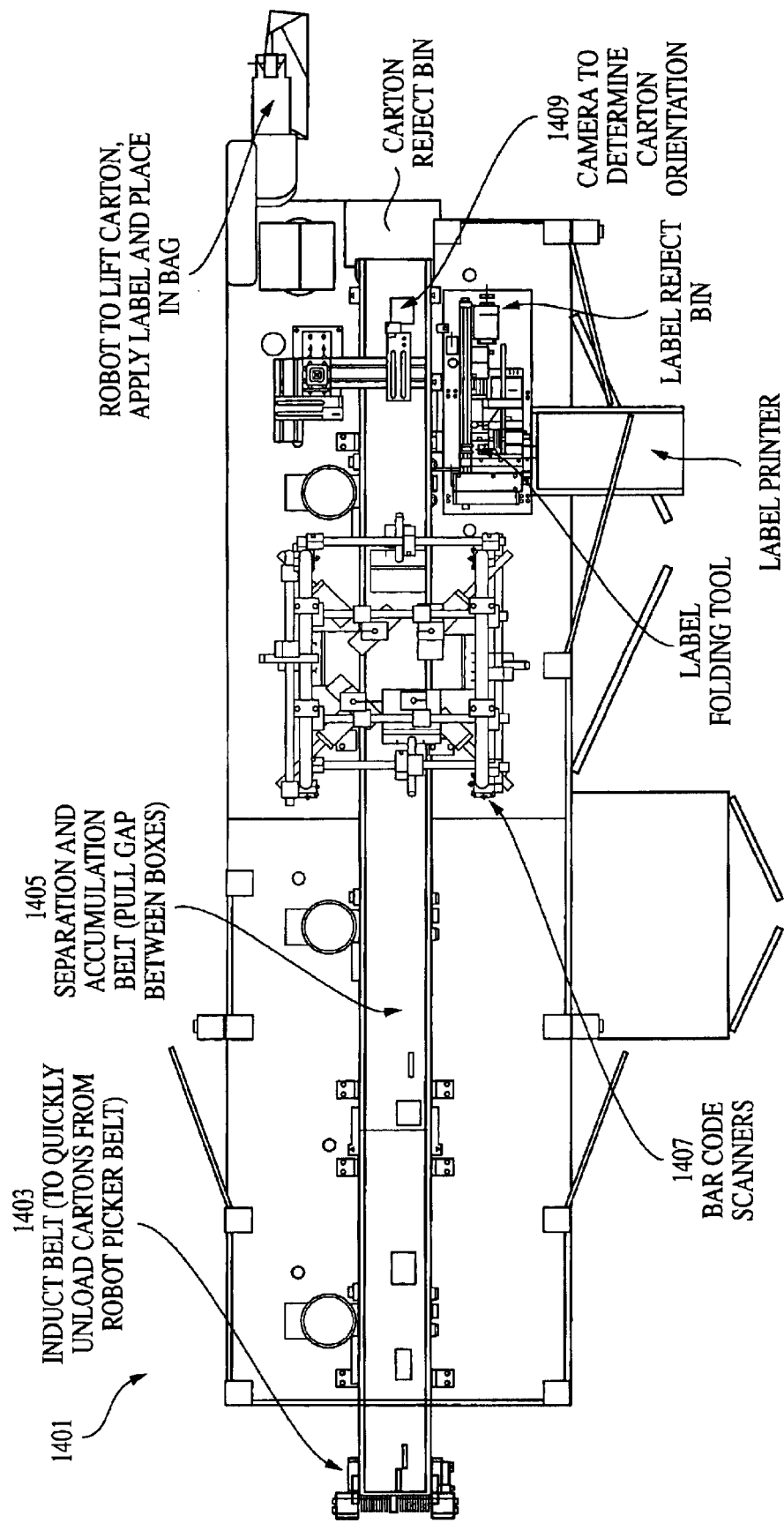
FIG. 14 is a diagram illustrating an example package scanning and labeling station of embodiments of the present invention.

Now referring to FIG. 14, there is shown mechanical/schematic illustration of an example embodiment of the dispenser for the packages 205 and consolidation station 215. In particular, FIG. 14 shows an example package scanning and labeling station 1401. The station 1401 includes an induct belt 1403 configured to receive packages picked and unloaded by the picking robot 809. The received packages are then transported to a separation and accumulation belt 1405 configured to put gaps between the packages. The separation and accumulation belt 1405 then moves the packages into a set of barcode scanners 1407 configured to detect and read barcodes from any of five exposed sides of the packages. (Since the packages are boxes, when the packages are placed on the belt 1405, five sides are exposed other than the side that touches the belt.) In such embodiments, when the packages are replenished into the shelves, their barcodes should not be on the bottom. In some other embodiments, only a top side can be scanned as long as the packages are placed into the shelves so that their barcodes are on the top. Accordingly, any combination of barcode readers can be used as long as barcodes on the packages can be detected and read. It should be noted that in some embodiments of the present invention, the belt 1405 can be transparent so that barcodes from the bottom side of the packages can also be detected and read by a barcode reader located below the belt 1405.

When barcodes are read, they are verified by a local computer. The local computer ensures that the scanned package actually belongs to the order that is about to be filled by the consolidation station 215. After the barcode scanners 1407 are used, the images of the packages are captured by a camera 1409. The images are then sent to the local computer to determine the shape and orientation of the packages as they lay on the belt 1405. Based on the determined shape, height and orientation, the local computer commands a robot arm to pick up the package from the belt 1405. An example of conventional computer vision software includes Adept AIM System, Motionware, Robot & Vision, Version 3.3B-Jun. 9, 1999, U.S. Pat. No. 4,835,730.

Figure 15A:
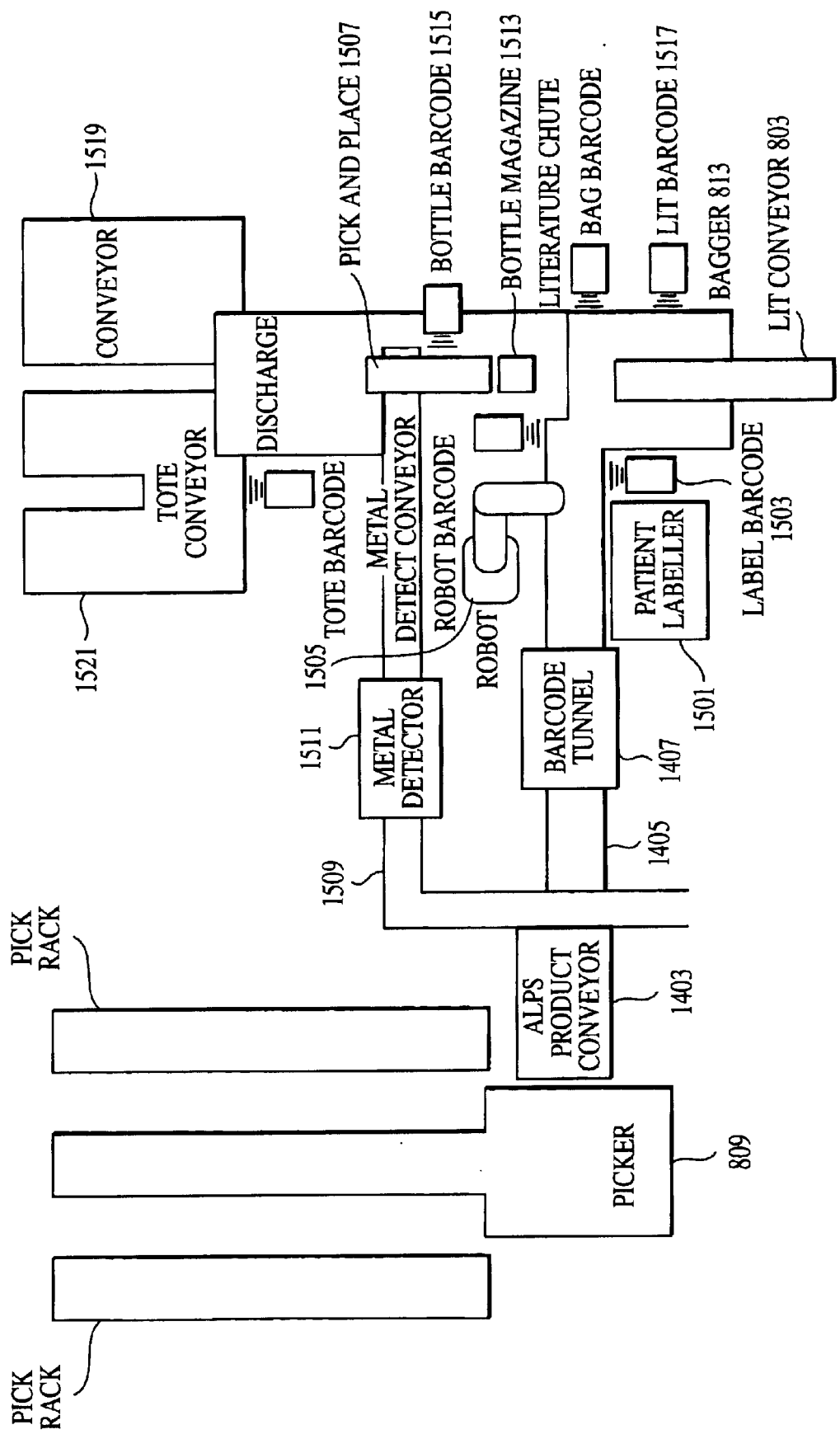
FIGS. 15A–15E are diagrams of an example consolidation station and its associated components of embodiments of the present invention.
Figure 15B:
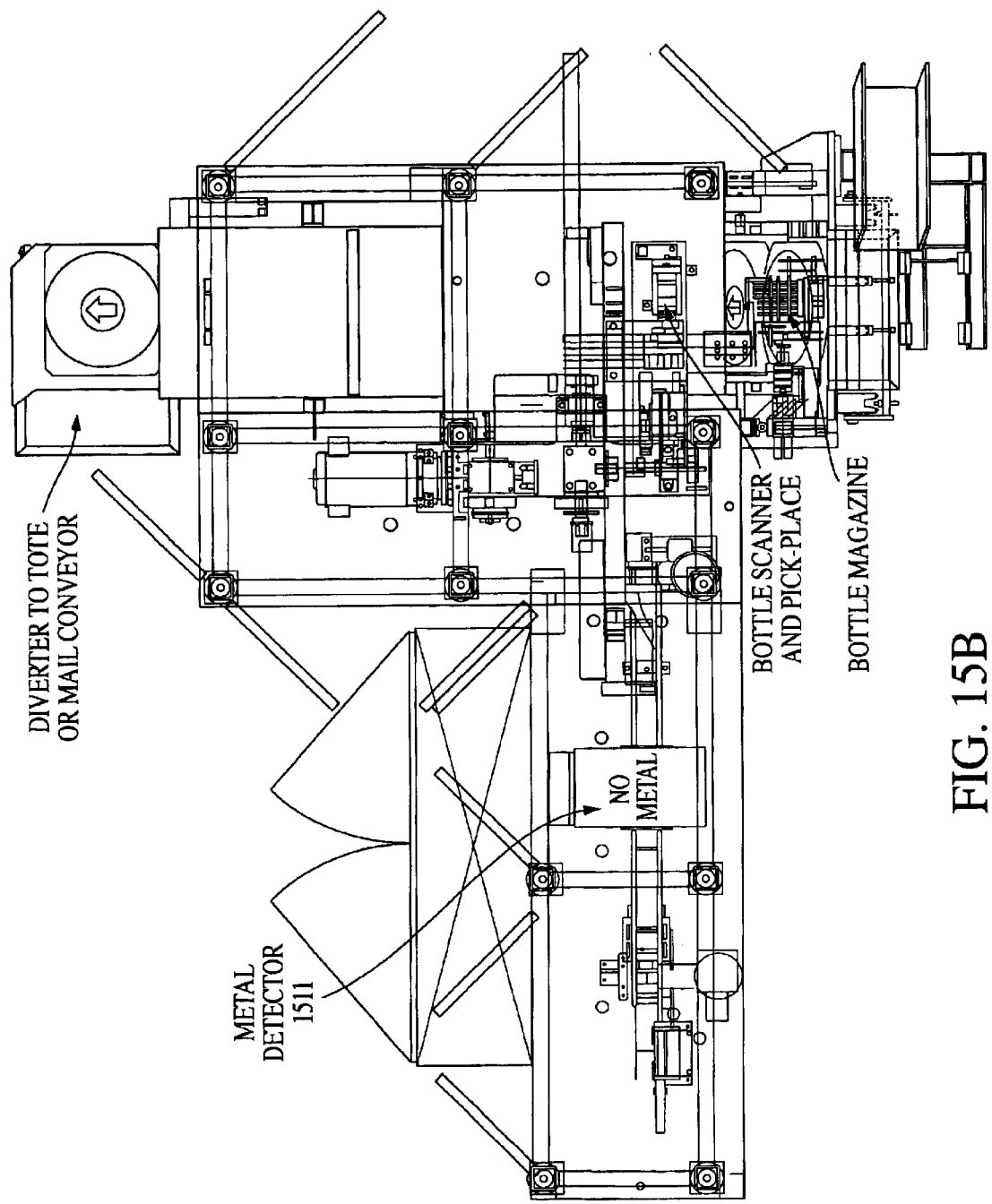
Figure 15C:
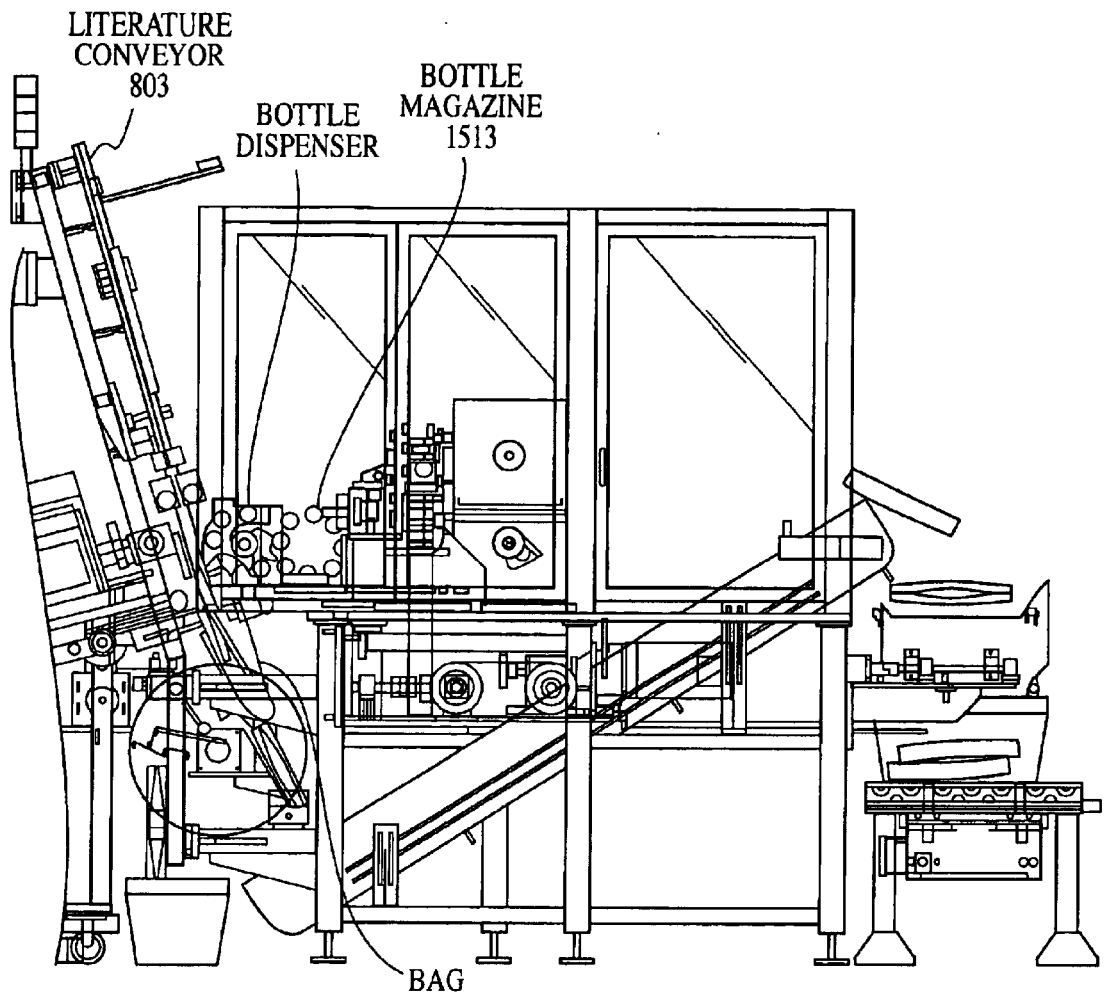
Figure 15D:
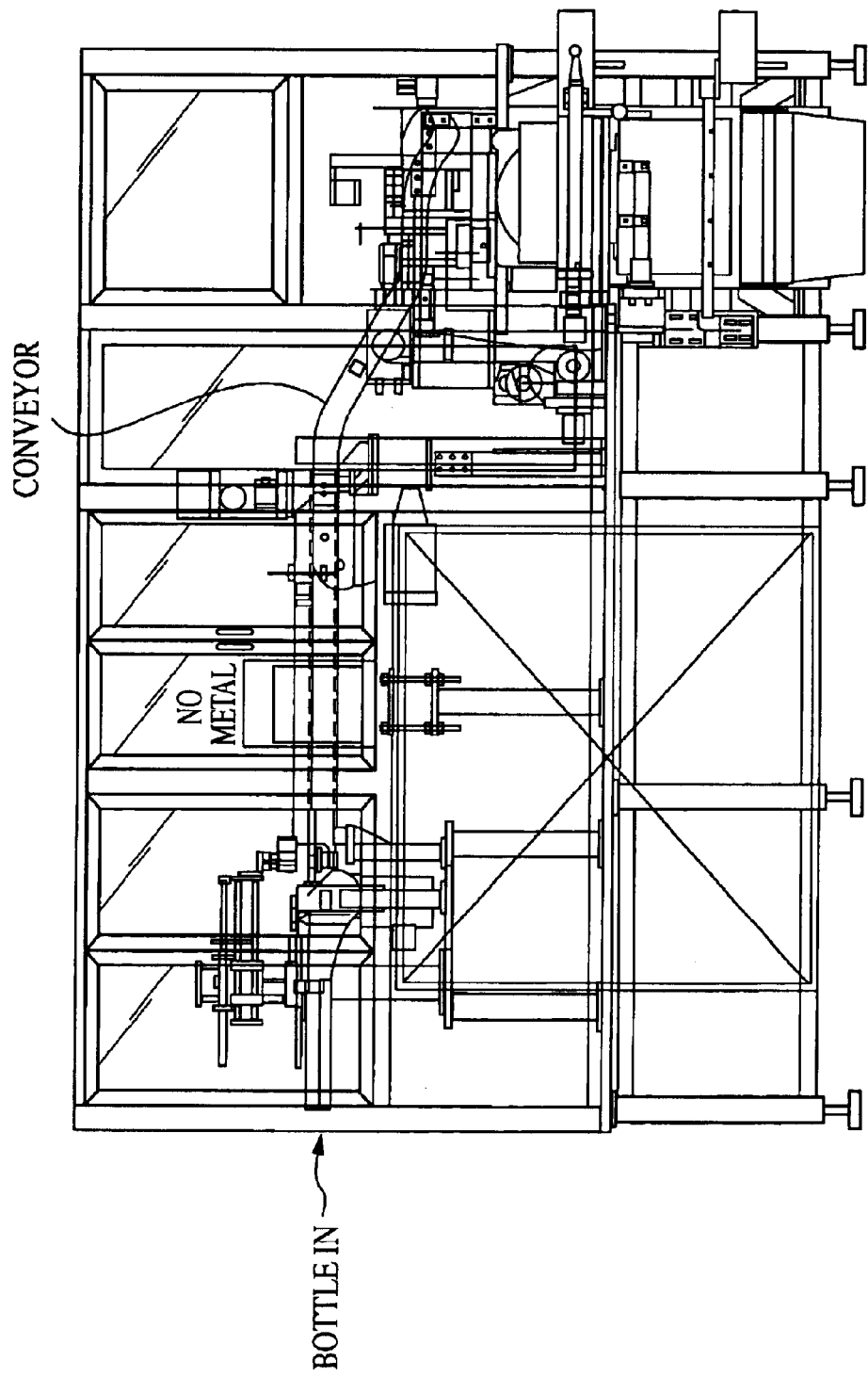
Figure 15E:
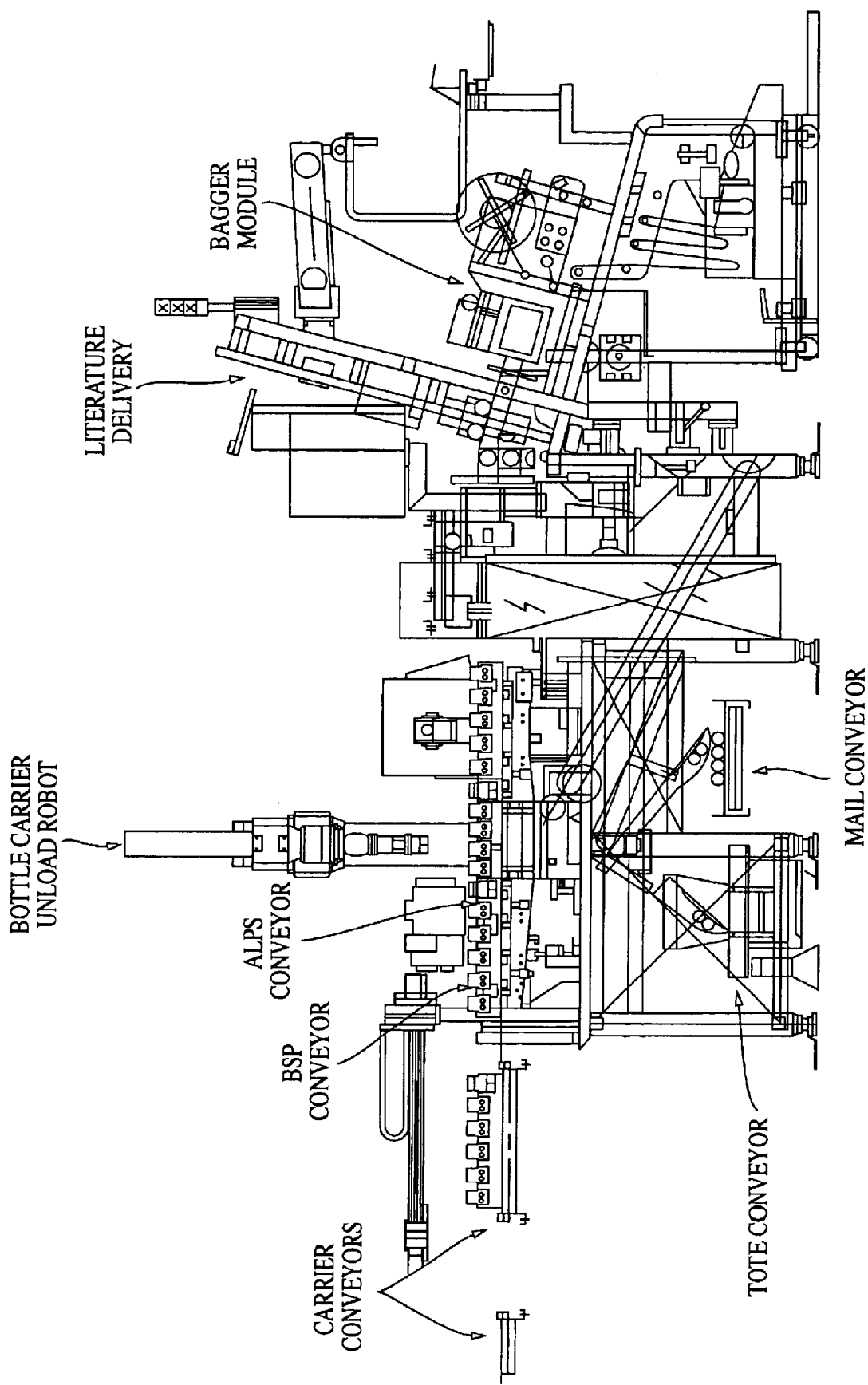
Figure 16:
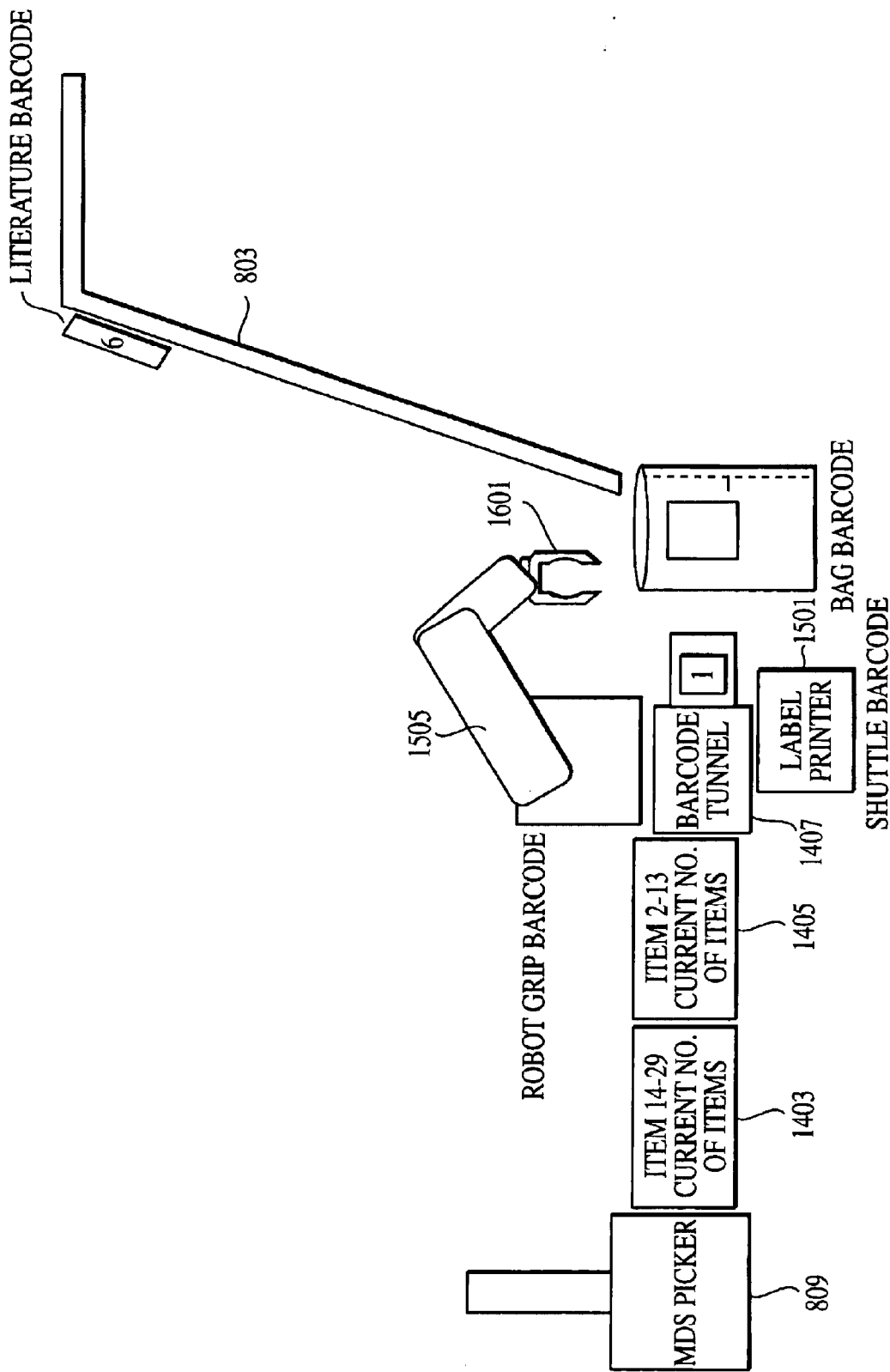
FIG. 16 is a schematic diagram of example bagger and dispenser for packages of embodiments of the present invention.
Figure 17:
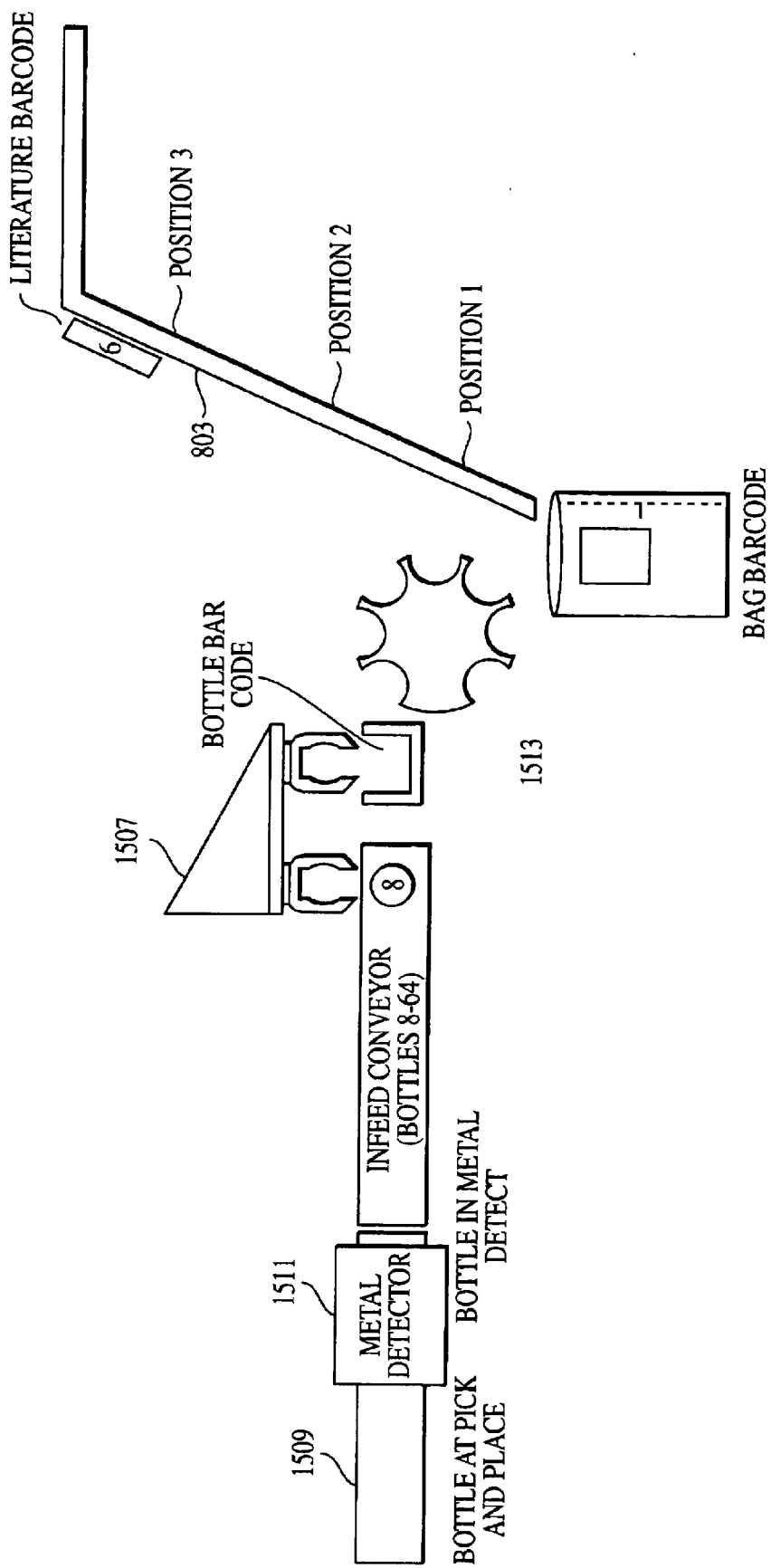
FIG. 17 is a schematic diagram of an example bagger and dispenser for bottles of embodiments of the present invention.

FIGS. 15A, 16 and 17 schematically show example components of the storage device for packages 203, dispenser for the packages 205 and consolidation station 215. FIGS. 15B–E show mechanical drawings of parts of these example components in different perspective views. As part of the dispenser for the packages 205, the example embodiment includes the induct conveyor belt 1403 for the packages, the conveyor belt 1405 for the packages, the barcode tunnel 1407, a order labeler 1501, a label barcode reader 1503 and a robot 1505. An example of conventional label printers includes Zebra Technologies Corp., Model: 90XiIII, Address: 333 Corporate Woods Parkway, Vernon Hills, Ill. 60061. And, and example of conventional robots includes Staubi Corp., Model: RX60, Address: 201 Parkway West, P.O Box 189; Hillside Park, Duncan, S.C. 29334.

Similar to the example embodiment shown in FIG. 14, the packages are transported through the barcode tunnel 1407 that detects and reads barcodes on the packages. The packages are then picked up by the robot 1505 (using its end effector 1601 as shown in FIG. 16). The local computer causes a patient label to be printed by the patient labeler 1501 for each package. The information printed on the labels and the form of the labels are discussed below in connection with FIG. 18. While a package is picked up by the robot 1505 and being transported, its label is affixed to the package. Then the robot 1505 swings the package next to the barcode reader 1503. The presence of a correct label is determined by the label barcode reader 1503. In addition, the robot 1501, label barcode reader 1503, and their local computer can also be configured to cooperate with each other to detect the labels and reject any packages without a label or with an incorrect label. Once, the package is determined to have a correct label affixed thereto, the robot 1505 can drop the package into the bag opened in the bagger 813 as will be discussed below in connection with FIGS. 19–20.

With respect to the bottles, they are transported via a metal detect conveyor 1509 which has a metal detector 1511 rejected thereon. In such example embodiments, the bottles are passed through the metal detector 1511 which determines any presence of metallic substances in the bottles. Bottles with metallic substances are rejected. The bottles belonging to one order are then placed into a bottle magazine 1513 by a pick-and-place device 1507. An example of pick-and-place devices includes Stelron, Model: SVIP-A-M-P-6.00, X-2.00 Y-spec, U.S. Pat. No. 3,703,834, Mahwah, N.J. In this example embodiment, a bottle barcode reader is provided to ensure that correct bottles have been delivered to the bottle magazine. Once all the bottles have been loaded to the bottle magazine, they can be released into the bag opened by the bagger 813 all will be discussed below in connection with FIGS. 19–20.

With respect to the literature packs, they are transported to the bagger 813 via the literature conveyor 803. As the packs arrive at the bagger 813, their barcodes are detected and checked by a literature barcode reader 1517. The literature barcode reader 1517 and it local computer ensures that correct literature packs are to be included in the bag. As the literature packs arrive, they are discharged into the bag as will be discussed below in connection with FIGS. 19–20.

Figure 18:
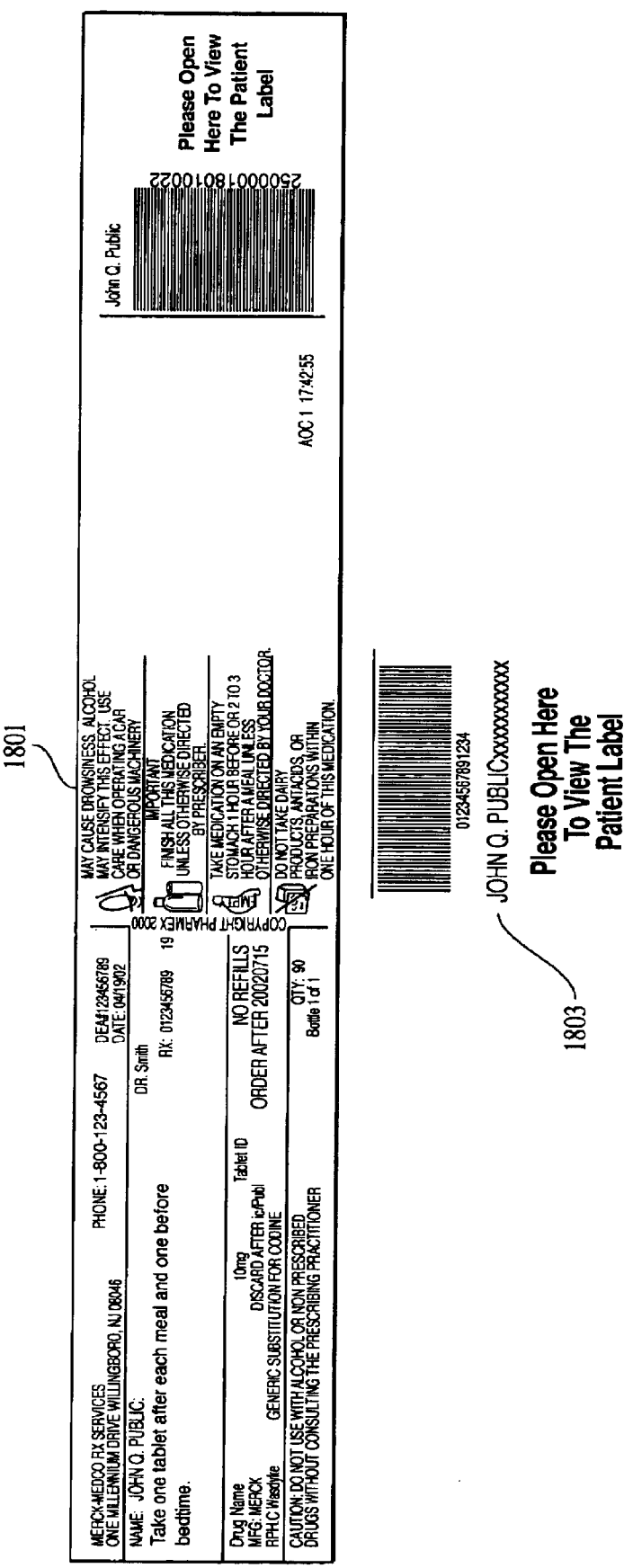
FIG. 18 is a diagram illustrating a label for a package of embodiments of the present invention.

FIG. 18 illustrates an example label 1801 to be affixed on a package. The label has patient information printed thereon. For instance, the patient information may include one or any combination of the following information: the name of the doctor; how often the package is to be taken by the patient; the name of the drug; the manufacturer of the drug; the number or strength of the drug; any warnings; any refills; and/or the number of or quantity of the packages being dispensed, directly or indirectly, to the patient, if it is standard patient label information. Other information as required may alternatively be printed or placed on the label as well.

The label, after being printed, is folded up so that one surface has adhesive placed thereon and the other surface has an identification mark (e.g., barcodes) printed thereon. An example of a folded label is shown as 1803. The side with the adhesive is placed on its corresponding package and pressed thereon in order to securely attach the label to its package. When the label is folded up, its size is approximately, a one and one-half inch long by one and one-half inch wide. When the label is not folded, the label is about eleven inches long in its width is one and one-half inches. A wrapping tool is provided to fold up the labels.

In contrast to the prior art Outserts which do not contain information specific to any patient, the present invention advantageously includes patient specific information on the label.

Figure 19:
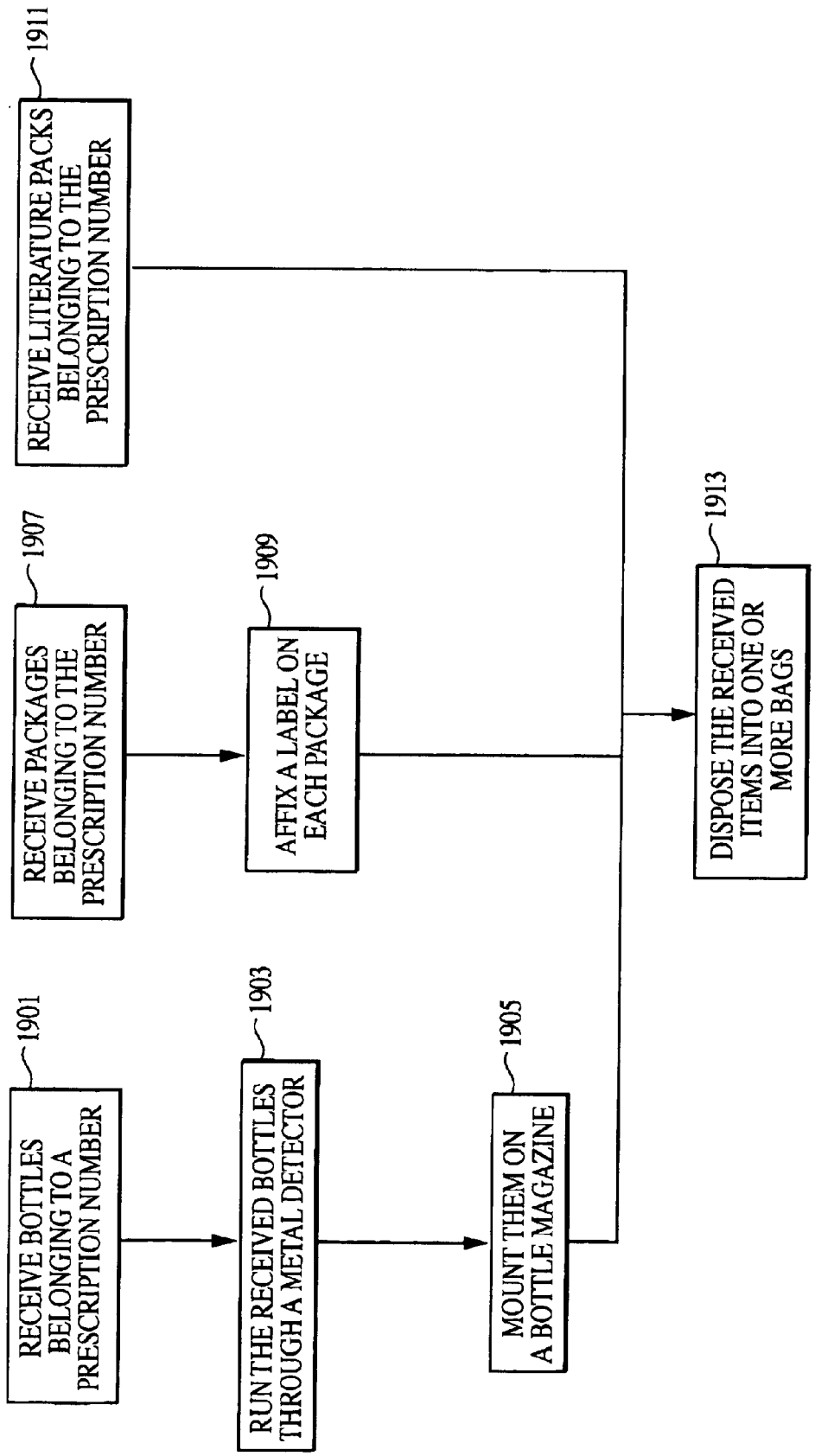
FIG. 19 is a diagram illustrating the steps performed and dispenser for packages and its local computer of embodiments of the present invention.

FIG. 19 illustrates the steps taken by the various components, their local computers, and the host computer 201 in the order consolidation station 215. In particular, bottles belonging to one order number are received from the bottle storage table 805 (step 1901). The received bottles are run through the metal detector 1511 (step 1903). The bottles are then mounted on the bottle magazine 1513 by the pick-and-place device 1507 (step 1905). Simultaneously, packages belonging to the same order number are received from the storage device for packages 203 (step 1907). A label is affixed to each of the received packages (step 1909). Again simultaneously, the conveyor belt 803 moves literature packs belonging to the same order number to the bagger. When all the items arrive, they are disposed into one or more bags at the bagger 813.

If any error is detected, the items belonging to the same order number are all sent to a quality assurance station. If the error cannot be resolved, the order is cancelled and re-ordered. The host computer 201 reinitiates the process from the beginning to fill the order again. The example errors can be a rejected bottle because a metallic substance was detected, a patient label not being affixed to a package, incorrect literature packs being delivered, etc.

Figure 20:
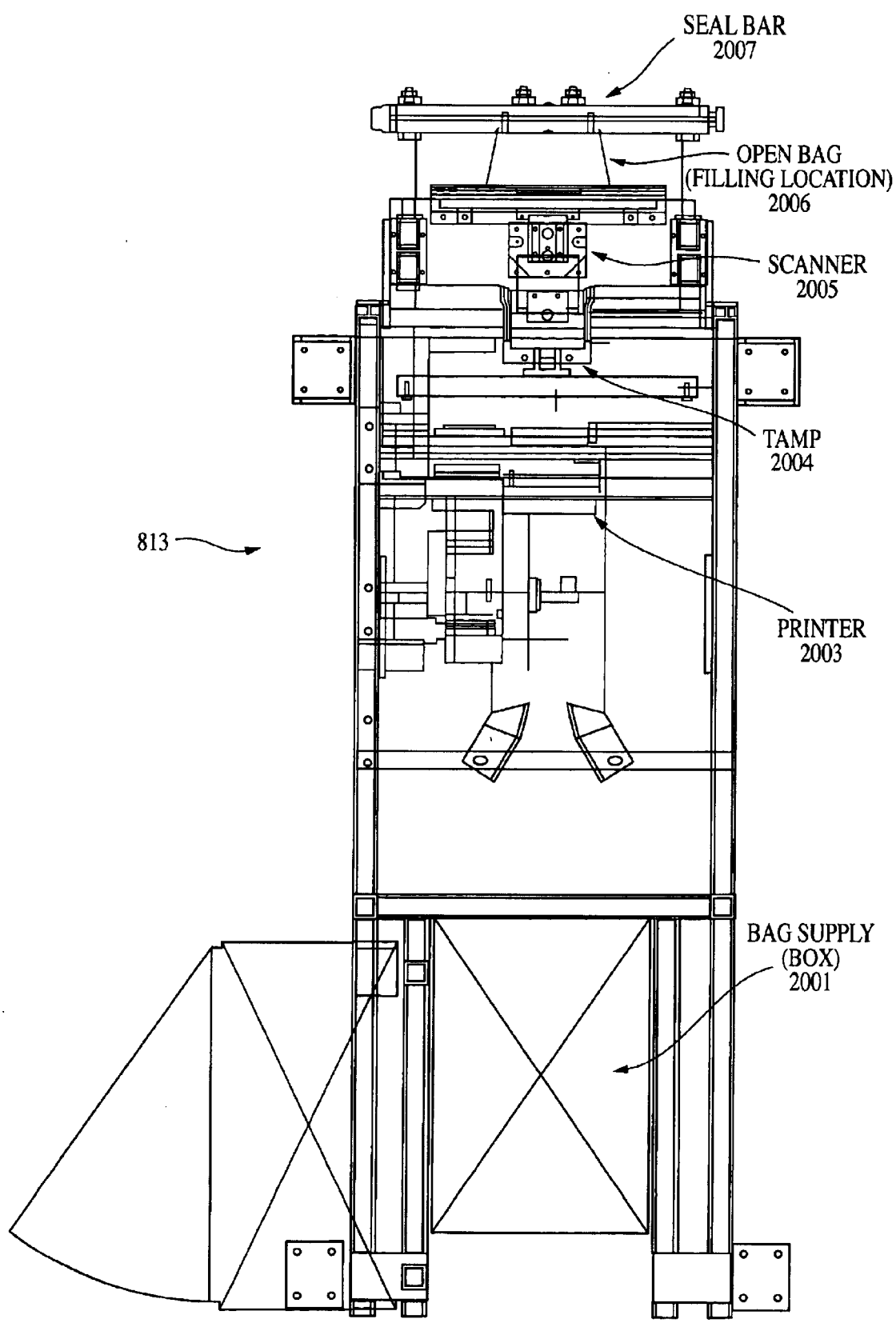
FIG. 20 is diagram illustrating an example bagger of embodiments of the present invention.

Now referring to FIG. 20, there is shown an example embodiment of the bagger 813 in detail. The example bagger 813 includes a supply of bags 2001, a printer 2003, tamp 2004, a scanner 2005, a mechanism 2006 to open a bag and hold it open and a mechanism 2007 to seal the bag. In operation, bags are fed from the bag supply 2001 one at a time. As the bags move up through the bagger 815, a label or information about the order that is about to be filled is placed on the bag. For example, The label may be printed and then pressed against the bag by the tamp 2004. The label or information is then detected and read by the scanner 2005. The scanner determines whether the correct label is printed and/or the label is properly affixed to the bag. The bag is then opened to receive the items in the manner as described above in connection with FIG. 19. If the bag contains all the items necessary to fill the order, then the bag is sealed. Optionally, the bag is not sealed, if an error is detected. If one or more manually picked packages are required as described above in connection with FIG. 7, then the bag is left unsealed. Although the present invention includes a bagger as described above, any container that can receive various pharmaceutical products and literature packs are also contemplated within this invention.

Now referring back to FIG. 15A, since the sealed bags are ready to be distributed or mailed, they are put on, for example, a conveyor belt 1519. For the unsealed bags, they are put on a tote conveyor 1521 in a tote. The tote is then transferred to an operator who can then completely fill the order by manually adding the required package(s).

Figure 21:
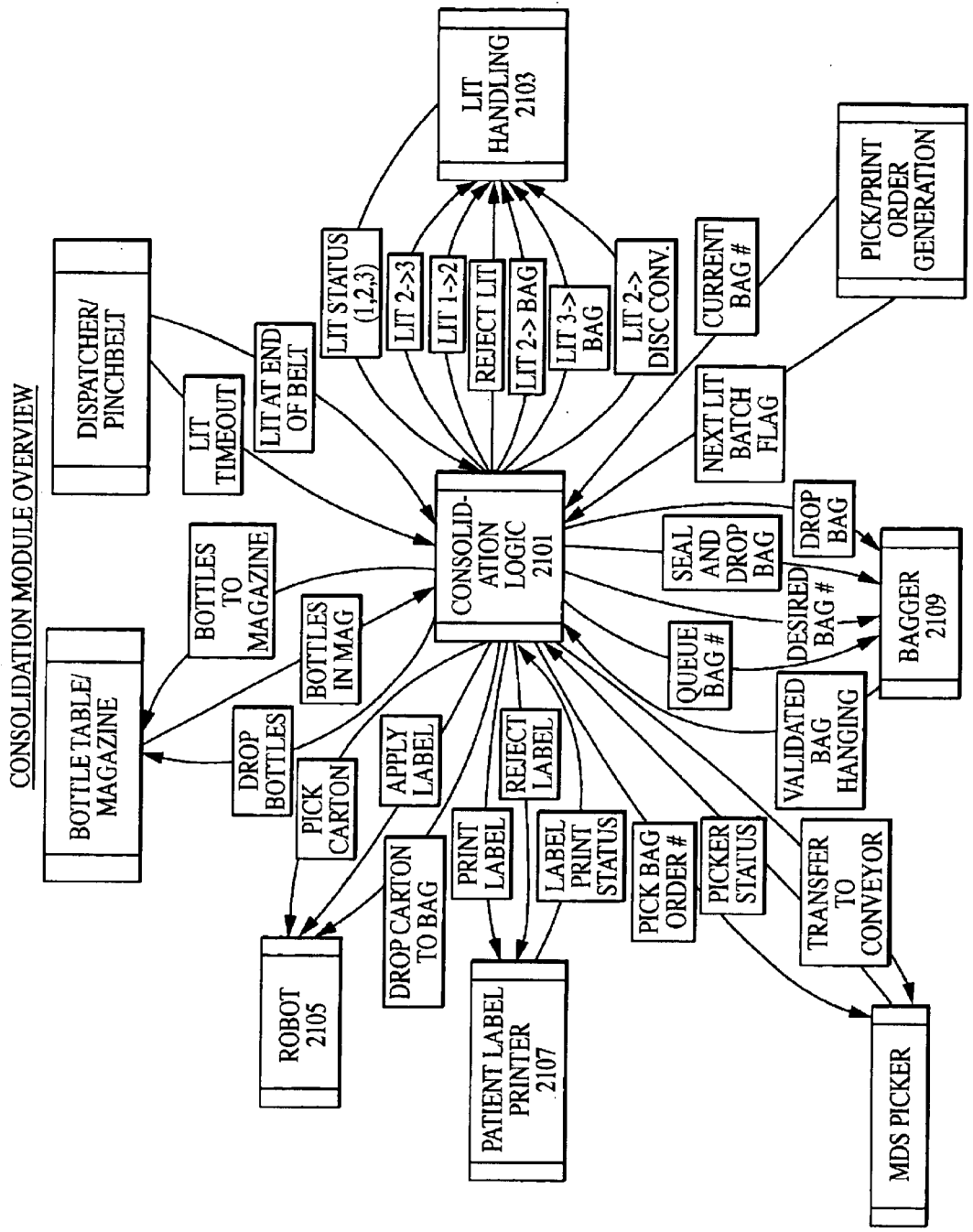
FIG. 21 is a diagram illustrating example control processes for embodiments of the present invention.

In order to fill order in the manner described above in connection with FIG. 19 in a continuous basis, flow logic, error detection and/or correction may be required. FIG. 21 illustrates an example process called consolidation logic 2101 and its interface with other example control logic processes for various components. The logic processes can run on the host computer 201 and/or in combination with the local computers.

For example, a literature handling process 2103 can interact with the consolidation logic process 2101 to ensure correct literature packs are included when a order is filled. As shown in FIG. 17, the conveyor belt has three positions. Position 1 designates the position on the belt 803 in which its literature pack is ready to be disposed into the bag at the bagger 813. Position 2 designates the position on the belt 803 in which its literature pack can be discarded if some error is detected. Position 3 designates the position on the belt in which the barcode reader 1517 shown in FIG. 15A detects and reads the barcode of the literature pack. The literature handling logic 2103 can report on the status of the literature packs in the three positions. In turn, the consolidation logic process 2101 can instruct the literature handling logic process 2103 to perform one or more tasks (e.g., accept or reject certain literature packs and/or advance the conveyor belt 803).

Figure 22:
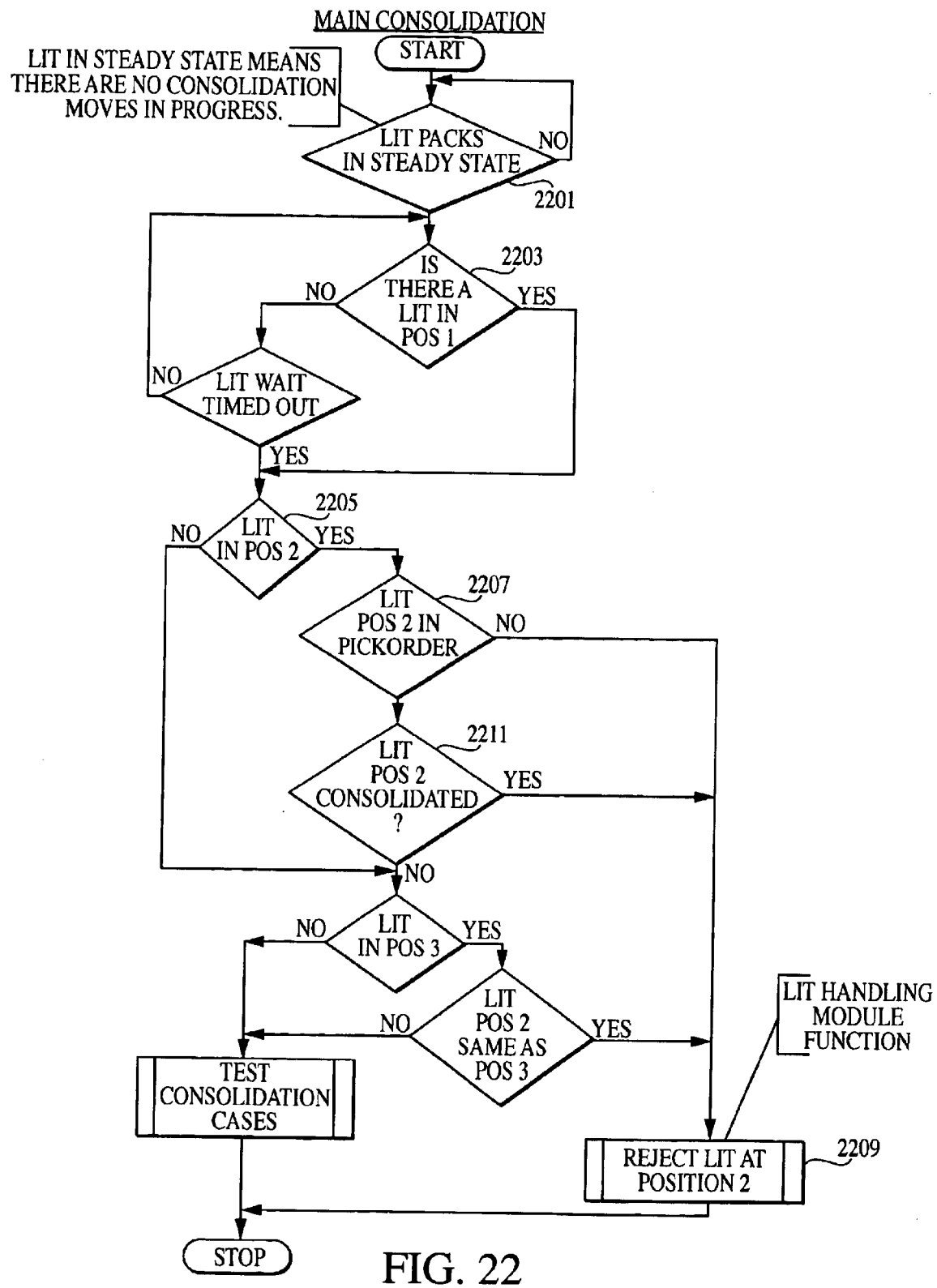
FIGS. 22–26 are diagrams illustrating example control schemes for literature packs of embodiments of the present invention.

For example, in FIG. 22, the consolidation logic 2101 starts by querying whether the literature packs are in a steady state (step 2201). In other words, the process 2101 is attempting to determine if the literature packs are being supplied by the conveyor belt 803. It is also attempting to determine if any literature packs have been consolidated. It then determines if there are literature packs in positions 1 and 2 (steps 2201 and 2203). If the answer is affirmative, then it further determines if the literature pack in the position 2 is in the same order as the literature packs were picked by the dispatch unit 801 and fed to the conveyor belt 803 (step 2209). If not, the literature pack in the position 2 is discarded (step 2209). If affirmative, then the consolidation logic 2101 further determines if the literature pack in the position 2 is consolidated (step 2211). If affirmative, then the literature pack in position 2 is discarded (step 2209). Subsequently, the belt 803 is moved one position to repeat the processes. In this way, multiple literature packs can be put into one bag.

Figure 23:
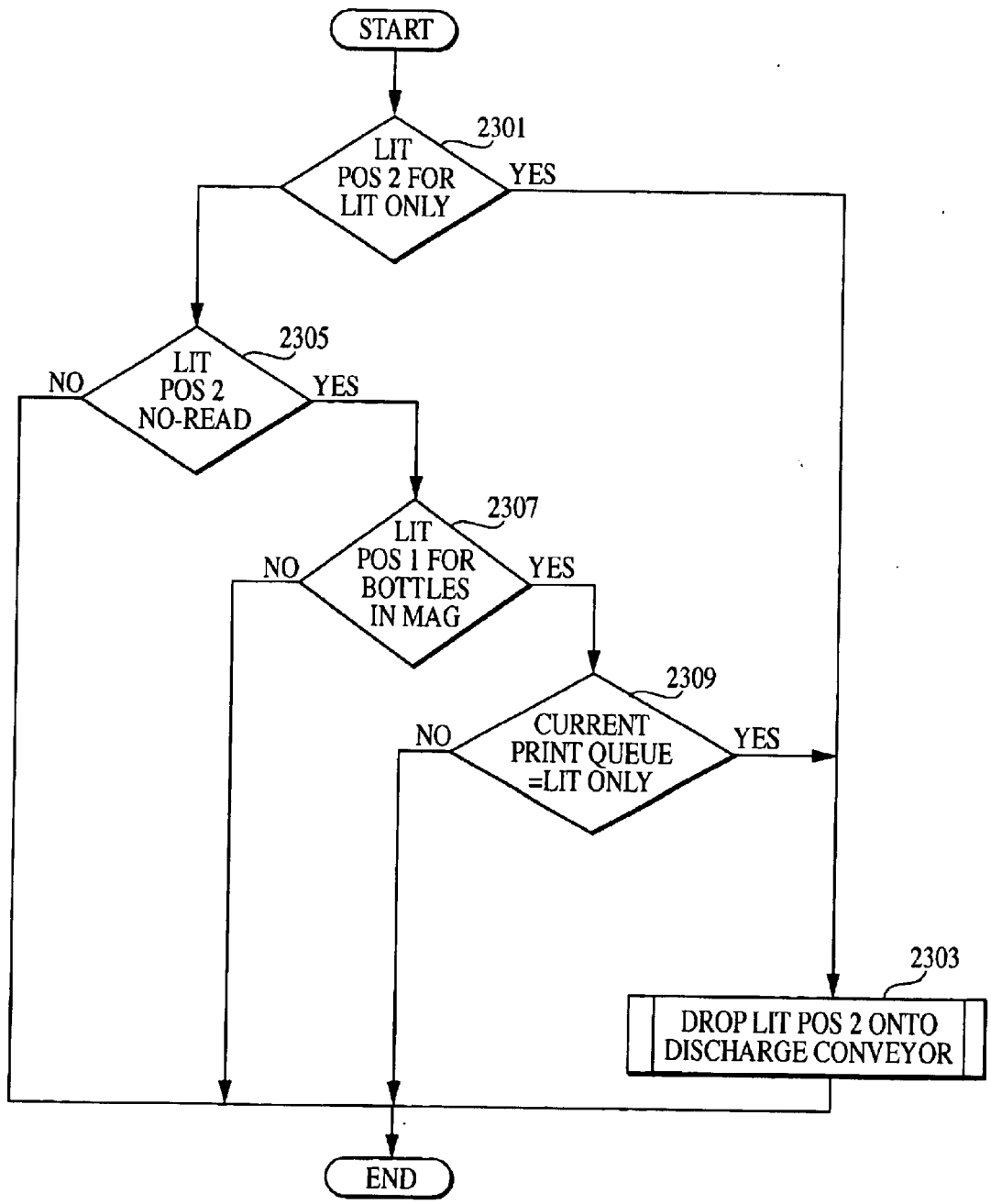
Figure 24:
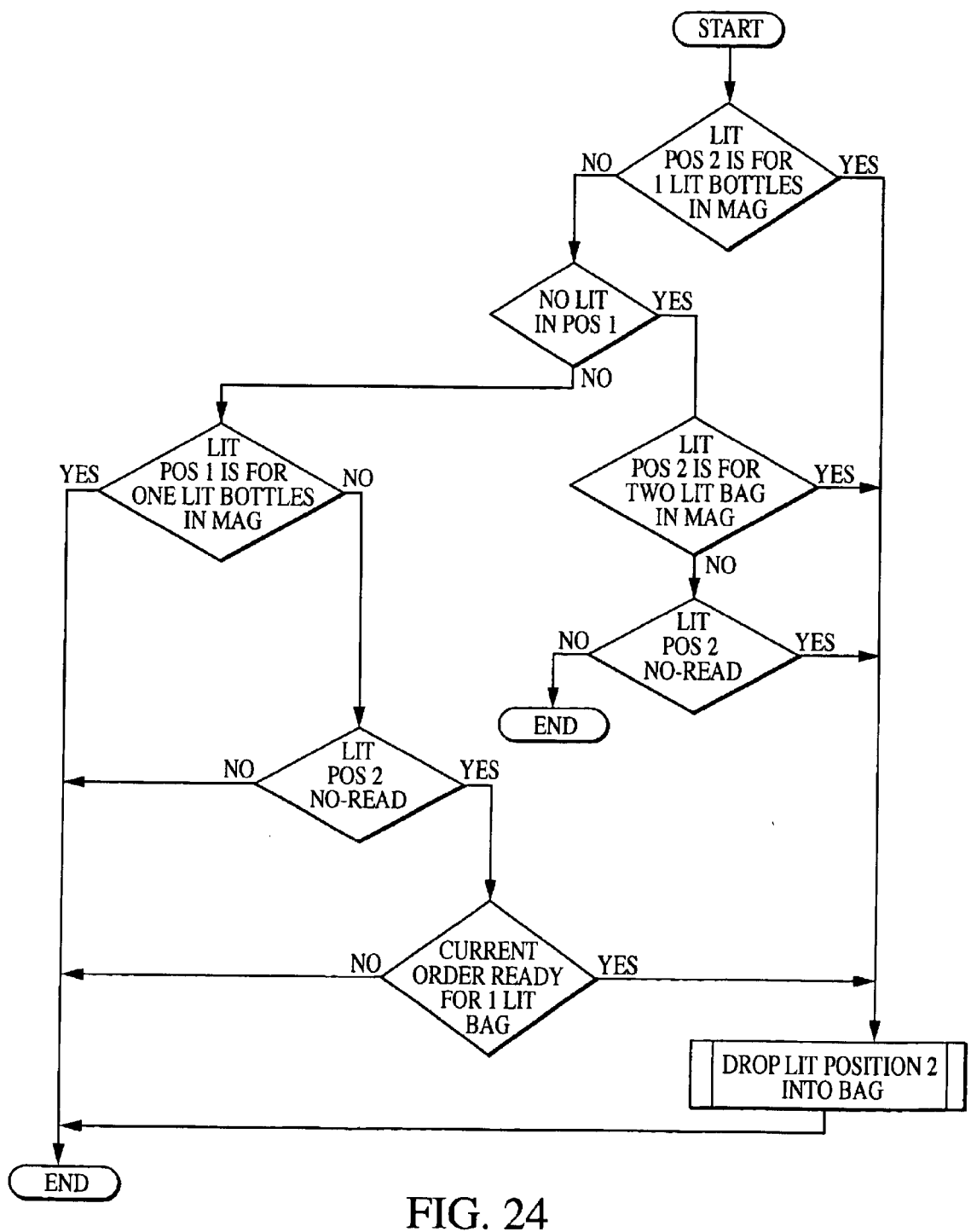
Figure 25:
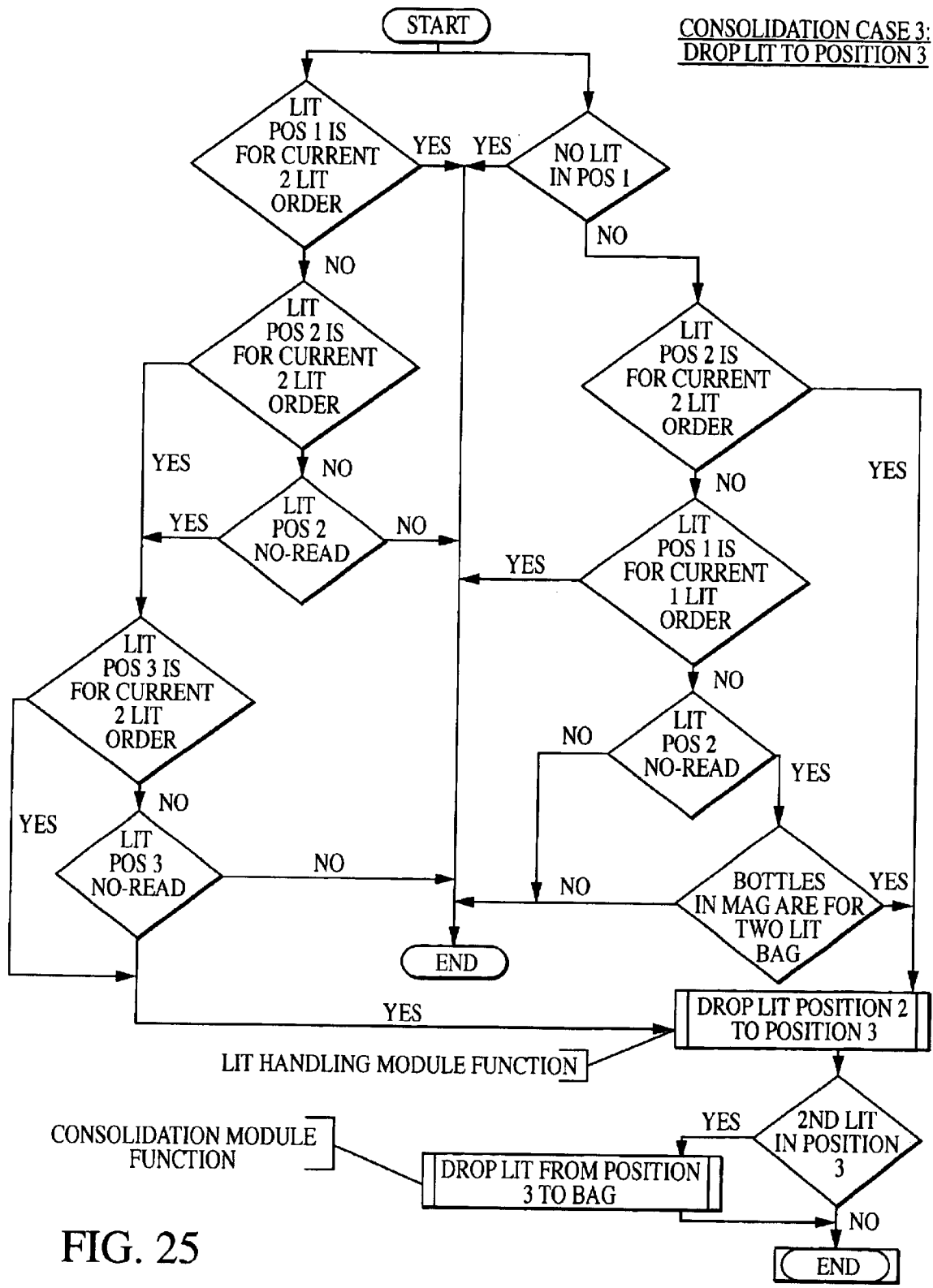
Figure 26:
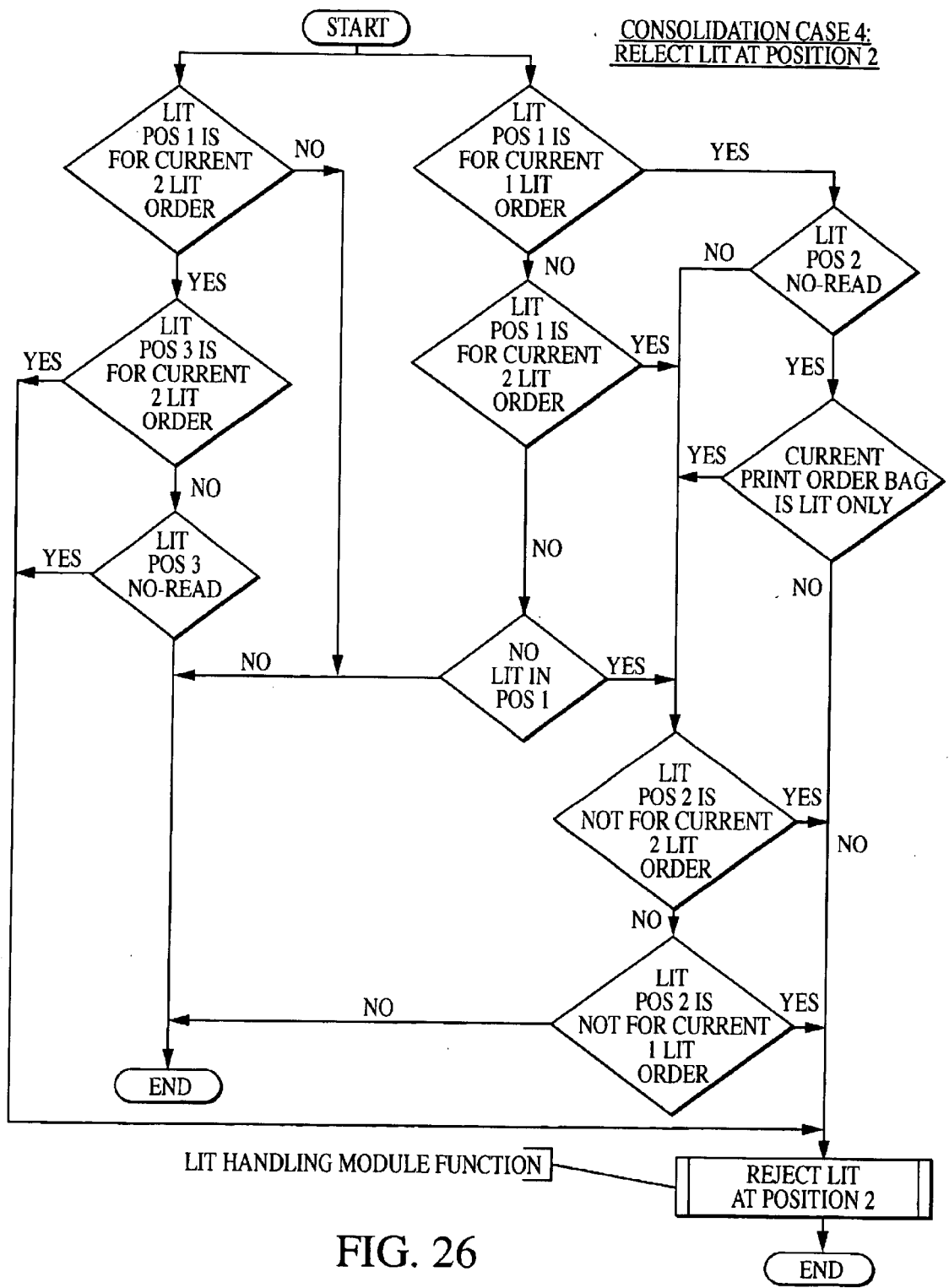

In some occasions, a bag at the bagger 813 cannot receive all the items. A second bag may be required to put literature packs only. This is called a literature pack only order. For such an order, the bagger 813 is not required to print a mailing label. As shown in FIG. 23, the logic process 2101 first determines if the literatures pack in the position 2 is for literature only order (step 2301). If so, the literature pack is discharged (step 2303). If not, the process confirms the barcode is detected and read the barcode on the literature pack (step 2305). If so, the process further determines if the literature pack in the position 1 is for the bottles in the bottle magazine (step 2307). If so, the process also determines if the print queue in the bagger is in a literature only mode (i.e., not required to print any label) (step 2309). If so, then the literature pack is discharged (step 2303). FIGS. 24–26 show various other decisions to be made by the literature handling logic process 2103 and consolidation logic process 2101.

Now referring back to FIG. 21, besides the literature handling logic 2103, the consolidation logic process 2101 also interacts with other processes (e.g., a robot process 2105, patient label printer process 2107, bagger process 2109, etc.). It should be noted that FIGS. 21–26 are provided herein only as a part of an example embodiment in which orders are continuously filled in a high speed. Furthermore, these logic processes are specifically engineered only in the case with specific implementations. For example, if there are four or more positions for the literature packs rather than three as described above, then the logic processes would be required to be correspondingly changed. Hence, one of ordinary skill in the art can appreciate possible permutations and combination of logic processes for various control flow logic implementations.

In addition, instead of relying solely on logic processes, in other example embodiments, manual processes can also be implemented. For instance, if an error is detected, the bag and its contents can be sent to quality assurance stations where one or more operators can check and correct the errors.

Figure 1A:
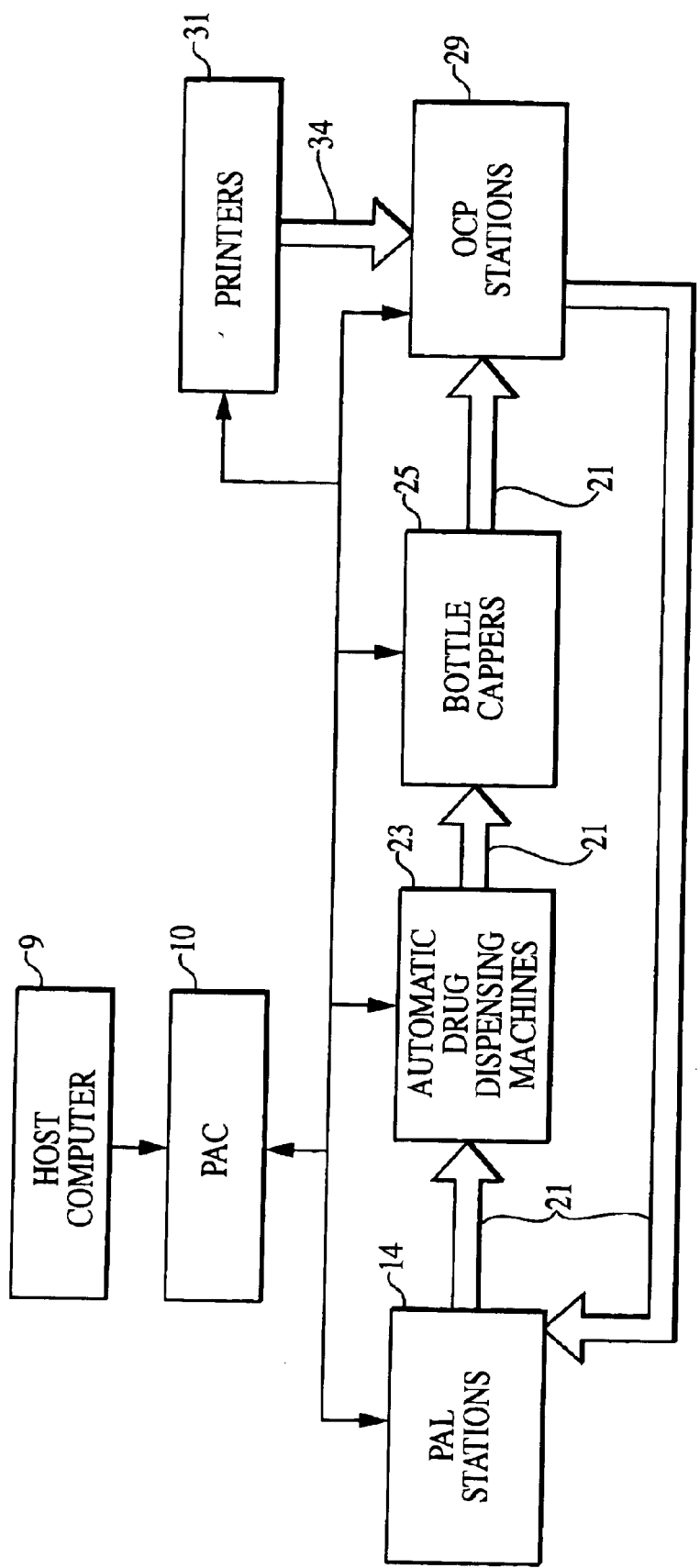
FIGS. 1A–1B are diagrams illustrating a conventional automated pill dispenser.
Figure 1B:
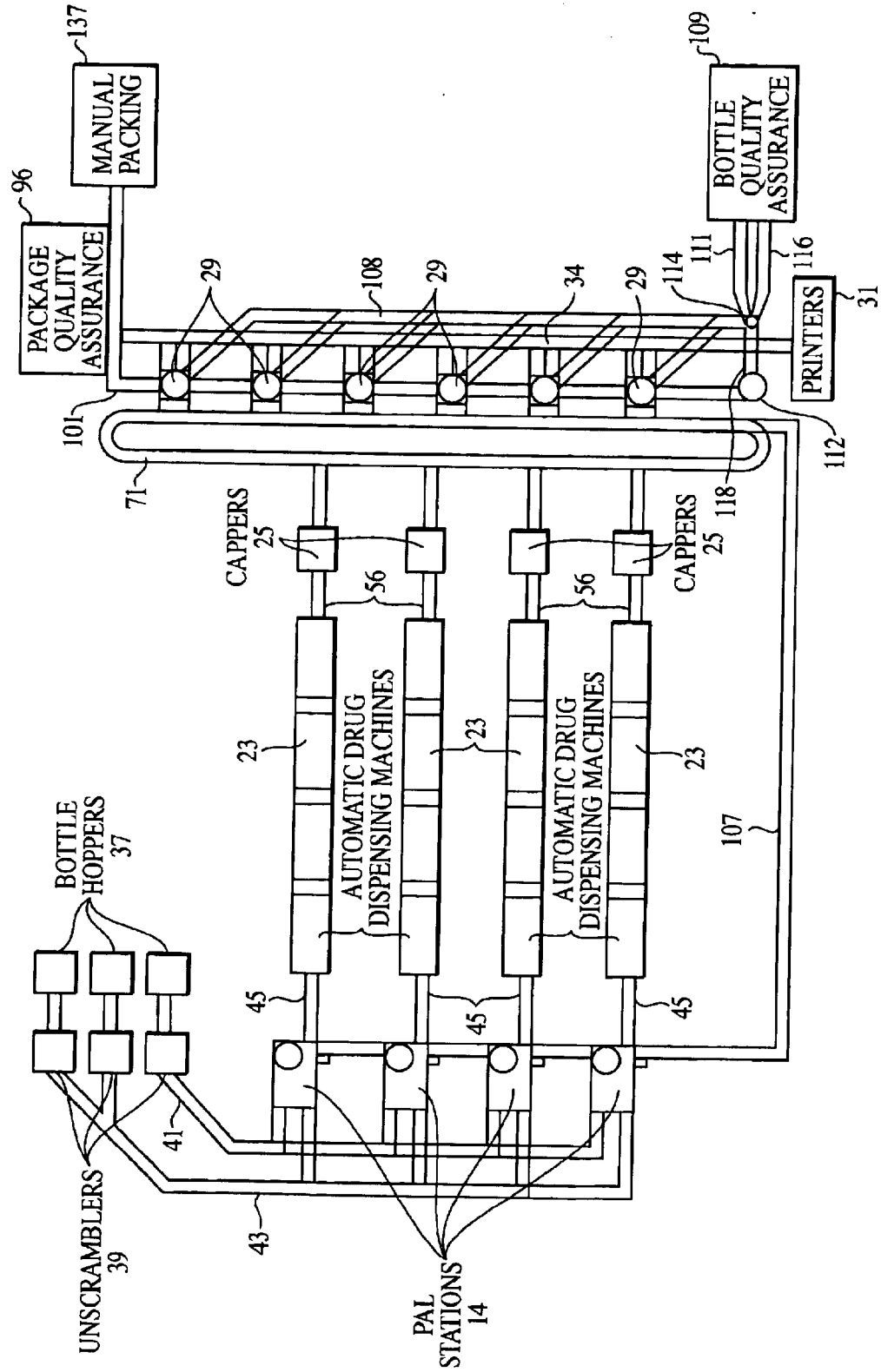
Figure 27:
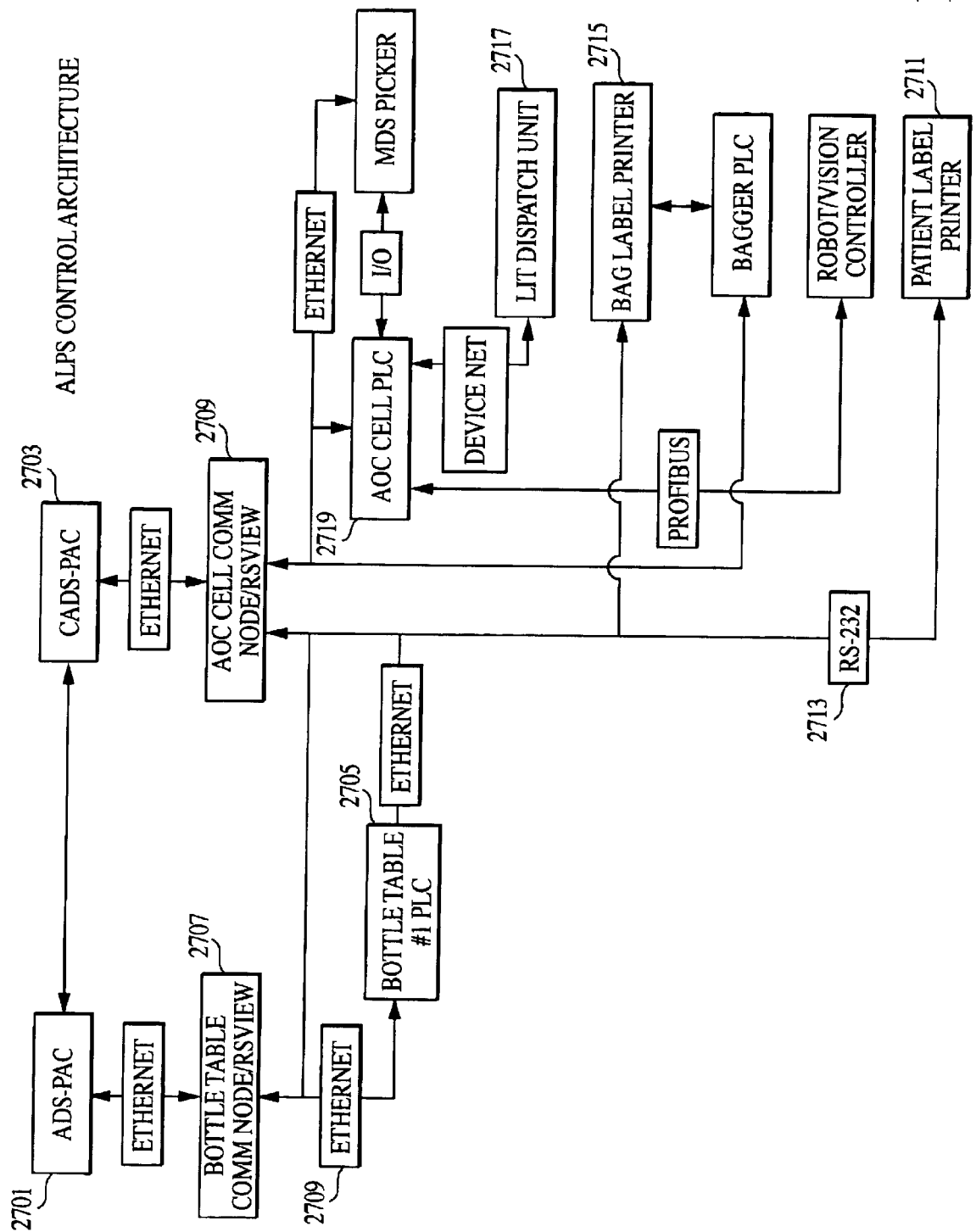
FIG. 27 is a diagram illustrating an example computer network scheme for embodiments of the present invention.

FIG. 27 is a computer networking diagram illustrating an example embodiment in which the host computer 201, local computers and their various processes are connected to each other. In this example embodiment, the host computer 201 includes two main processes: an ADS-PAC process 2701 and a CADS-PAC process 2703. The ADS-PAC process 2701 controls the way in which pills are dispensed into bottles in an automated pill dispensing device (e.g., the ADDS shown in FIG. 1). A bottle table 1 (one of many tables) includes a PLC 2705. The PLC 2705 is in turn connected to a bottle table communication node 2707 via a dedicated link 2709 (e.g., Ethernet). The node 2707 is then connected to the ADS-PAC 2701 via another dedicated link. Alternatively, the ADS-PAC and the CADS-PAC process may be combined or separated using a variety of standard methods or programming techniques.

Once bottles are filled for one or more orders, the information relating to those orders is transferred over to the CAD-PAC process 2703. This process then carries out the consolidation process. For example, the CAD-PAC process 2703 is connected to an AOC cell communication node 2709 via a dedicated line. The controller for the patient label printer 2711 is controlled directly by the AOC node 2709 over an RS-232 line 2713 because relatively large data need to be transferred to the printer to print the patient labels (similarly, the controller for the bagger printer 2715 also has a direct connection to the AOC node 2709). Other devices, for example, the controller for literature dispatch unit 2717, are indirectly connected to the AOC node 2709 via an AOC cell PLC 2719.

Figure 28:
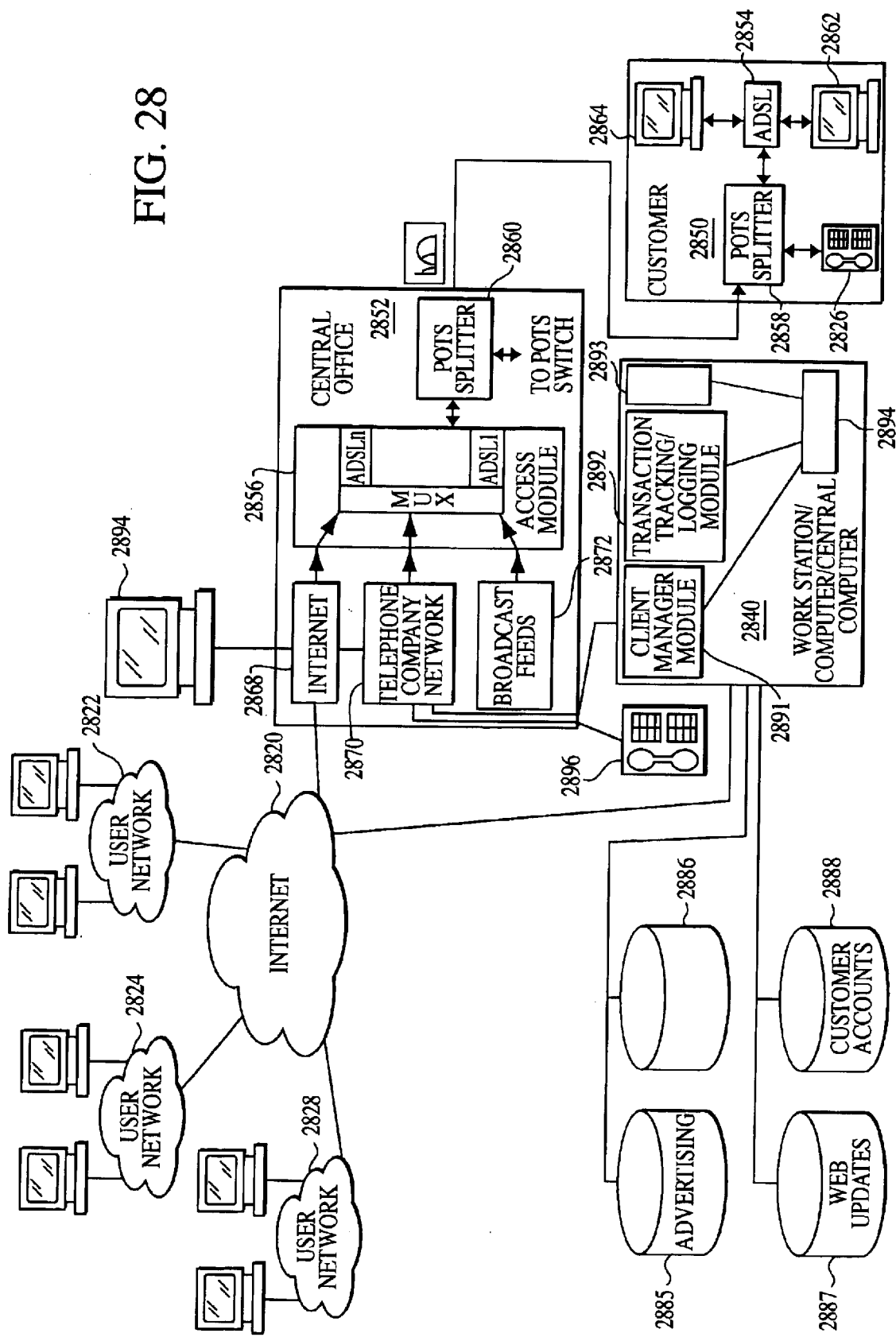
FIG. 28 is a block diagram representation of an example embodiment of computer network(s) implementing embodiments of the present invention.

FIG. 28 is an illustration of the architecture of the combined Internet, POTS (plain, old, telephone service), and ADSL (asymmetric, digital, subscriber line) for use in accordance with the principles of the present invention. In other words, instead of using dedicated lines and such communication schemes as shown in FIG. 27, this example embodiment envisions a remotely controllable system. Furthermore, it is to be understood that the use of the Internet, ADSL, and POTS are for exemplary reasons only and that any suitable communications network may be substituted without departing from the principles of the present invention. This particular example is briefly discussed below.

In FIG. 28, to preserve POTS and to prevent a fault in the ADSL equipment 2854, 2856 from compromising analog voice traffic 2826 the voice part of the spectrum (the lowest 4 kHz) is separated from the rest by a passive filter, called a POTS splitter 2858, 2860. The rest of the available bandwidth—from about 10 kHz to 1 MHz—carries data at rates up to 6 bits per second for every hertz of bandwidth from data equipment 2862, 2864, and 2894. The ADSL equipment 2856 then has access to a number of destinations including significantly the Internet 2820 or other data communications networks, and other destinations 2870, 2872.

To exploit the higher frequencies, ADSL makes use of advanced modulation techniques, of which the best known is the discrete multitone (DMT) technology. As its name implies, ADSL transmits data asymmetrically—at different rates upstream toward the central office 2852 and downstream toward the subscriber 2850.

Cable television services are providing analogous Internet service to PC users over their TV cable systems by means of special cable modems. Such modems are capable of transmitting up to 30 Mb/s over hybrid fiber/coax system, which use fiber to bring signals to a neighborhood and coax to distribute it to individual subscribers.

Cable modems come in many forms. Most create a downstream data stream out of one of the 6-MHz TV channels that occupy spectrum above 50 MHz (and more likely 550 MHz) and carve an upstream channel out of the 5–50-MHz band, which is currently unused. Using 64-state quadrature amplitude modulation (64 QAM), a downstream channel can realistically transmit about 30 Mb/s (the oft-quoted lower speed of 10 Mb/s refers to PC rates associated with Ethernet connections). Upstream rates differ considerably from vendor to vendor, but good hybrid fiber/coax systems can deliver upstream speeds of a few megabits per second. Thus, like ADSL, cable modems transmit much more information downstream than upstream. Then Internet architecture 2820 and ADSL architecture 2854, 2856 may also be combined with, for example, user networks 2822, 2824, and 2028.

In accordance with the principles of the present invention, in one example, a main computing server (e.g., the host computer 201) implementing the process of the invention may be located on one or more computing nodes or terminals (e.g., on user networks 2822, 2824, and 2828 or system 2840). Then, various users (e.g., one or more of the local computers described above) may interface with the main server via, for instance, the ADSL equipment discussed above, and access the information and processes of the present invention from remotely located PCs. As illustrated in this embodiment, users may access, use or interact with the computer assisted program in computer system 2840 via various access methods. Databases 2885, 2886, 2887, 2888, and 2840 are accessible via, for example computer system 2840 and may be used in conjunction with client manager module 2891, tracking module 2892, for the various functions described above.

Figure 29:
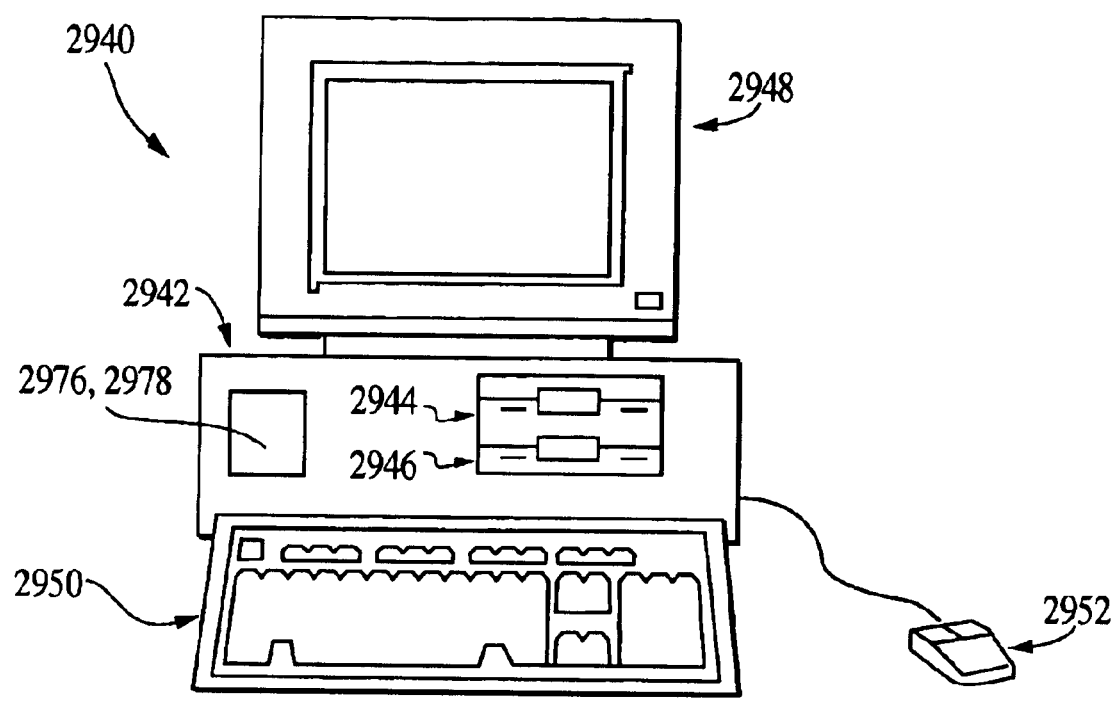
FIG. 29 illustrates a computer that can be used in implementing embodiments of the present invention.

Viewed externally in FIG. 29, a computer system (e.g., the host computer 201 or the local computers) designated by reference numeral 2940 has a computer 2942 having disk drives 2944 and 2946. Disk drive indications 2944 and 2946 are merely symbolic of a number of disk drives which might be accommodated by the computer system. Typically, these would include a floppy disk drive 2944, a hard disk drive (not shown externally) and a CD ROM indicated by slot 2946. The number and type of drives vary, typically with different computer configurations. Disk drives 2944 and 2946 are in fact optional, and for space considerations, are easily omitted from the computer system used in conjunction with the production process/apparatus described herein.

The computer system also has an optional display upon which information screens may be displayed. In some situations, a keyboard 2950 and a mouse 2952 are provided as input devices through which a user's actions may be inputted, thus allowing input to interface with the central processing unit 2942. Then again, for enhanced portability, the keyboard 2950 is either a limited function keyboard or omitted in its entirety. In addition, mouse 2952 optionally is a touch pad control device, or a track ball device, or even omitted in its entirety as well, and similarly may be used to input a user's selections. In addition, the computer system also optionally includes at least one infrared transmitter and/or infrared received for either transmitting and/or receiving infrared signals, as described below.

Figure 30:
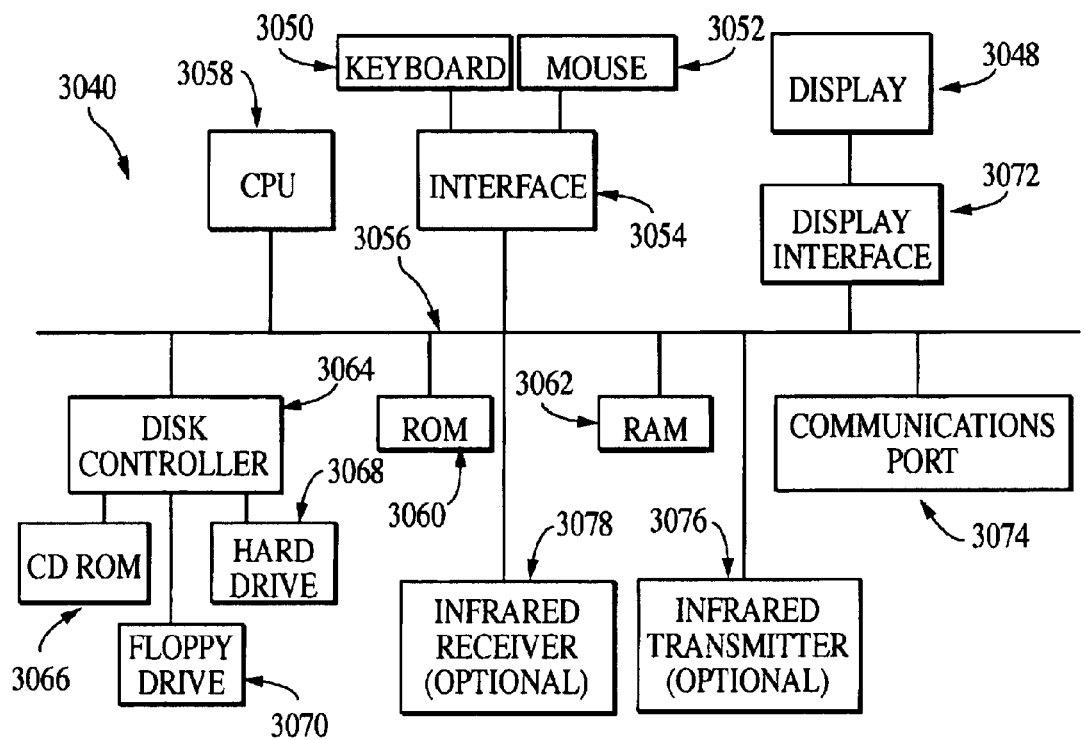
FIG. 30 is a block diagram of internal hardware of the example computer shown in FIG. 29.

FIG. 30 illustrates a block diagram of one example of the internal hardware 3040 configured to perform various example steps as described above. A bus 3056 serves as the main information highway interconnecting various components therein. CPU 3058 is the central processing unit of the internal hardware 3040, performing calculations and logic operations required to execute the control/operation processes of the present invention as well as other programs. Read only memory (ROM) 3060 and random access memory (RAM) 3062 constitute the main memory of the internal hardware 2140. Disk controller 3064 interfaces one or more disk drives to the system bus 3056. These disk drives are, for example, floppy disk drives 3070, or CD ROM or DVD (digital video disks) drives 3066, or internal or external hard drives 3068. These various disk drives and disk controllers are optional devices.

A display interface 3072 interfaces display 3048 and permits information from the bus 3056 to be displayed on display 3048. Communications with external devices such as the other components (e.g., a PLC) of the system described above, occur utilizing, for example, communication port 3074. Optical fibers and/or electrical cables and/or conductors and/or optical communication (e.g., infrared, and the like) and/or wireless communication (e.g., radio frequency (RF), and the like) can be used as the transport medium between the external devices and communication port 3074. Peripheral interface 3054 interfaces the keyboard 3050 and mouse 3052, permitting input data to be transmitted to bus 3056. In addition to these components, the internal hardware 3040 also optionally include an infrared transmitter and/or infrared receiver. Infrared transmitters are optionally utilized when the computer system is used in conjunction with one or more of the processing components/ stations/modules that transmits/receives data via infrared signal transmission. Instead of utilizing an infrared transmitter or infrared receiver, the computer system may also optionally use a low power radio transmitter 3080 and/or a low power radio receiver 3082. The low power radio transmitter transmits the signal for reception by components of the production process, and receives signals from the components via the low power radio receiver. The low power radio transmitter and/or receiver are standard devices in industry.

Figure 31:
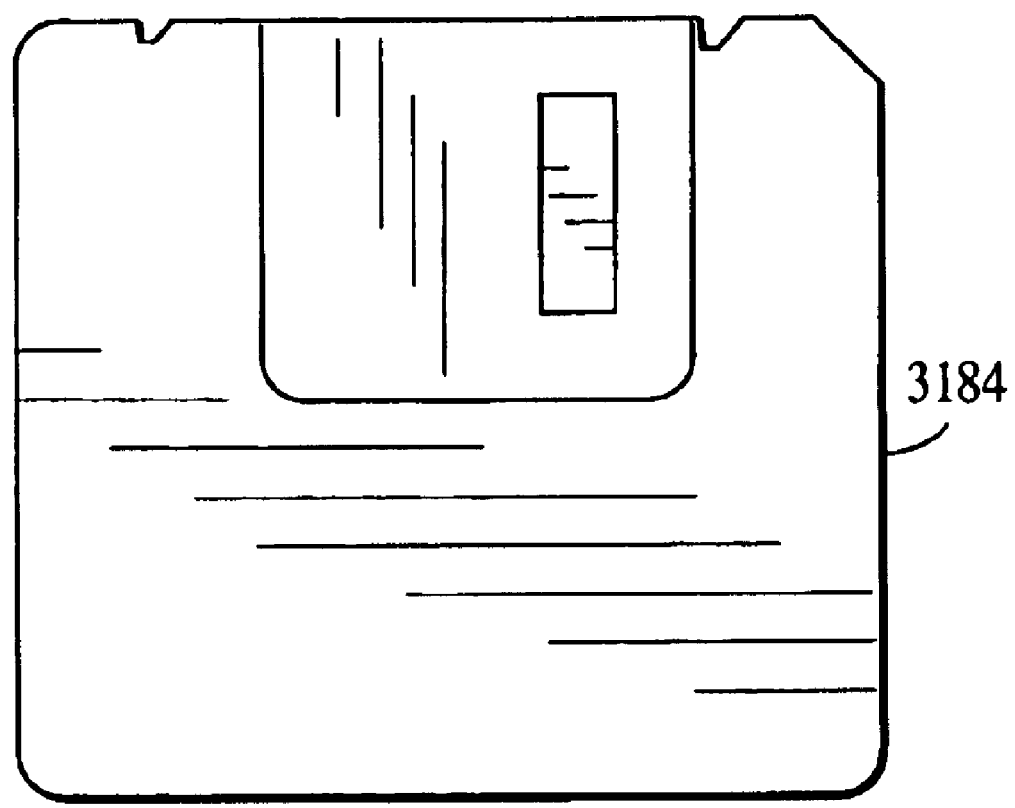
FIG. 31 illustrates one example of a memory medium which may be used for storing computer programs of embodiments of the present invention.

Although the server in FIG. 31 is illustrated having a single processor, a single hard disk drive and a single local memory, the analyzer is optionally suitably equipped with any multitude or combination of processors or storage devices. For example, the computer may be replaced by, or combined with, any suitable processing system operative in accordance with the principles of embodiments of the present invention, including sophisticated calculators, and hand-held, laptop/notebook, mini, mainframe and super computers, as well as processing system network combinations of the same.

FIG. 31 is an illustration of an example computer readable memory medium 3184 utilizable for storing computer readable code or instructions. As one example, medium 3184 may be used with disk drives illustrated in FIG. 30. Typically, memory media such as floppy disks, or a CD ROM, or a digital video disk will contain, for example, a multi-byte locale for a single byte language and the program information for controlling the modeler to enable the computer to perform the functions described herein. Alternatively, ROM 3060 and/or RAM 3062 illustrated in FIG. 30 can also be used to store the program information that is used to instruct the central processing unit 3058 to perform the operations associated with various automated processes of the present invention. Other examples of suitable computer readable media for storing information include magnetic, electronic, or optical (including holographic) storage, some combination thereof, etc.

In general, it should be emphasized that the various components of embodiments of the present invention can be implemented in hardware, software or a combination thereof. In such embodiments, the various components and steps would be implemented in hardware and/or software to perform the functions of embodiments of the present invention. Any presently available or future developed computer software language and/or hardware components can be employed in such embodiments of the present invention. For example, at least some of the functionality mentioned above could be implemented using Visual Basic, C, C++, or any assembly language appropriate in view of the processor(s) being used. It could also be written in an interpretive environment such as Java and transported to multiple destinations to various users.

The many features and advantages of embodiments of the present invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A system for filling at least one prescription order, said system comprising at least one order consolidation station configured to:

receive from a first transport system at least one bottle containing a number of pills individually counted as determined by the at least one prescription order;

receive from a second transport system at least one package containing prepackaged pharmaceutical products;

at least one identifier detector to detect at least one identification information associated with the at least one bottle, and to detect at least another identification information associated with the at least one package;

at least one mechanism to place the at least one bottle and the at least one package into a container; and a control system that coordinates the first and second transport systems and the at least one mechanism so that the at least one bottle and the at least one package are placed in the container when the at least one identification information associated with the bottle and the at least another identification information associated with the at least one container correspond to the at least one prescription order.

2. The system of claim 1, wherein the at least one order consolidation station is further configured to:

print at least one customized literature pack for the at least one prescription order comprising patient specific information; and insert automatically the at least one literature pack into the container.

3. The system according to claim 2, wherein the at least one identifier detector determines whether the at least one bottle, the at least one package, the at least one customized literature pack, and the container belong to the at least one prescription order.

4. The system of claim 1, further comprising:

a package storage device having an array of locations and configured to store the at least one package into one of the array of locations; and a package dispenser configured to identify the one of the array of locations, obtain the at least one package from the one of the array of locations and provide the at least one package to the second transport system.

5. The system of claim 4, wherein the package dispenser further includes a package label printer to print at least one label for the at least one package, wherein the label is printed with patient specific information.

6. The system of claim 5, wherein the package dispenser further includes a labeler to affix a label on the at least one package.

7. The system of claim 5, wherein the package dispenser further includes an error detection system configured to detect the label affixed on the at least one package and reject the at least one package if an error is detected.

8. The system of claim 1, further comprising:
a package storage device having an array of locations and configured to store a plurality of packages into the array of locations and store the at least one package into one of the array of locations; and
a package dispenser configured to identify the one of the array of locations, obtain the at least one package from the one of the array of locations and provide the at least one package to the second transport system.

9. The system of claim 1, further comprising:
a bottle storage device having an array of locations and configured to store the at least one bottle into one of the array of locations; and
a bottle dispenser configured to identify the one of the array of locations and dispense the at least one bottle from the one of the array of the locations.

10. The system of claim 9, further comprising a metal detector configured to detect a metallic substance in the at least one bottle, wherein the bottle is transported to a quality assurance area if a metallic substance is detected.

11. The system of claim 9, wherein the bottle dispenser comprises a bottle buffer configured to receive the at least one bottle belonging to the one of at least one prescription order, wherein the bottle buffer is disposed and configured to release the received at least one bottle to the first transport system.

12. The system of claim 1, further comprising a packager configured to open the container to receive the at least one bottle and at least one package.

13. The system of claim 12, wherein the packager comprises:
a printer configured to print an address or internal control information, and affix the address or the internal control information on the container.

14. The system of claim 12, wherein the packager comprises a bagger system, and wherein said container comprises a bag.

15. The system of claim 14, wherein the bagger system comprises:
a printer configured to print an address or internal control information, and affix the address or the internal control information on the bag.

16. The system of claim 1, wherein the at least one prescription order consolidation station is further configured to:
print at least one customized literature pack for the at least one prescription order comprising patient specific information; and
insert automatically the at least one literature pack for the at least one bottle and the at least one package into the container.

17. A system for filling at least one prescription order, comprising:
a bottle handling station configured to store and dispense at least one bottle containing a number of pills as determined by the at least one prescription order;
a package handling station configured to store and dispense at least one package containing prepackaged pharmaceutical products; and
an order consolidation station configured to receive the at least one bottle from a first transport system and receive the at least one package containing prepackaged pharmaceuticals from a second transport system;
at least one identifier detector to detect at least one identification information associated with the at least one bottle, and to detect at least one other identification information associated with the at least one package;
at least one mechanism to place the at least one bottle and the at least one package into a container; and
a control system that coordinates the first and second transport systems and the at least one mechanism so that the at least one bottle and the at least one package are placed into the container when the at least one identification information associated with the at least one bottle and the at least one other identifier information associated with the at least one package correspond to the at least one prescription order.

18. The system of claim 17, further comprising:
a literature handling station configured to print and store at least one literature pack containing patient specific information for the at least one prescription order, wherein the order consolidation station receives the at least one literature pack and inserts the at least one literature pack into the container.

19. The system according to claim 18, wherein the at least one identifier detector determines whether the at least one bottle, the at least one package, the at least one literature pack, and the container belong to a same prescription order.

20. The system of claim 17, wherein the package handling station comprises:
a package storage device having an array of locations and configured to store the at least one package into one of the array of locations; and
a package dispenser configured to identify the one of the array of locations, and obtain the at least one package from the one of the array of locations and provide the at least one package to the second transport system.

21. The system of claim 20, wherein the package dispenser further includes a package label printer to print at least one label for the at least one package, wherein the label is printed with patient specific information.

22. The system of claim 21, wherein the package dispenser further includes a device to affix the at least one label on the at least one package.

23. The system of claim 21, wherein the package dispenser further includes an error detection system configured to detect the label affixed on the at least one package and reject the at least one package and the label if an error is detected.

24. The system of claim 17, wherein the bottle handling station comprises:
a bottle storage device having an array of locations and configured to store the at least one bottle into one of the array of locations; and
a bottle dispenser configured to identify the one of the array of locations and dispense the at least one bottle from the one of the array of the locations.

25. The system of claim 24, further comprising a metal detector configured to detect a metallic substance in the at least one bottle, wherein the bottle is transported to a quality assurance area if a metallic substance is detected.

26. The system of claim 24, wherein the bottle dispenser comprises a bottle buffer configured to receive the at least one bottle belonging to one of at least one prescription order, wherein the bottle buffer is disposed and configured to release all received at least one bottle from said bottle storage area into the container.

27. The system of claim 17, further comprising a packager configured to open the container to receive the at least one bottle and at least one package.

28. The system of claim 27, wherein the packager comprises a printer configured to print a label comprising an address or internal control information, and affix the label on the container.

29. The system of claim 27, wherein the packager comprises a bagger system, and wherein said container comprises a bag.

30. The system of claim 29, wherein the bagger system comprises:
a printer configured to print an address or internal control information, and affix the address or the internal control information on the bag.

31. A system for filling a plurality of prescription orders, comprising:
a package handling station configured to store a plurality of packages containing prepackaged pharmaceutical products;
a literature handling station configured to print and store at least one literature pack relating to one of the plurality of prescription orders and coordinate the at least one literature pack with respect to corresponding prescription orders;
a computer system configured to monitor the package handling and literature handling stations and cause the package handling station to dispense the plurality of packages in coordination with the dispensing of the plurality of literature packs by the literature handling station;
at least one identifier detector to detect at least one identification information associated with the plurality of packages and at least another identification information associated with the at least one literature pack;
at least one mechanism to place the at least one bottle and the at least one package into a container;
an order consolidation station configured to receive the packages from a first transport system and the literature packs from a second transport system; and
a control system that coordinates the first and second transport systems and the at least one mechanism so that the packages and the literature packs are placed into the container when the at least one identification information and the at least one other identification information correspond to a same prescription order.

32. The system of claim 31, further comprising:
a bottle handling station configured to store a plurality of bottles, each bottle containing a number of pills as determined by a prescription order;
wherein the computer system is further configured to monitor the bottle handling station and cause the bottle handling station to dispense the bottles in coordination with the at least one literature pack, and
wherein the order consolidation station is further configured to receive the bottles associated with the corresponding prescription order and insert the bottles with the corresponding packages and literature packs into a container.

33. The system of claim 32, wherein the control system detects an error when the bottles received by the order consolidation station do not correspond with the at least one literature pack.

34. The system of claim 32, wherein the order consolidation station is configured to:
receive the bottles and the at least one literature pack in the order sequence in which the at least one literature pack is stored with respect to the corresponding prescription orders; and insert the bottles, packages and the at least one literature pack into the container.

35. The system of claim 34, wherein the control system detects an error when the bottles are not received by the order consolidation station in the order sequence in which the at least one literature pack is stored.

36. The system of claim 32, wherein the container comprises a bag.

37. The system according to claim 32, wherein the at least one identifier detector determines if the plurality of bottles, the plurality of packages, the at least one literature pack, and the container belong to a same prescription order.

38. The system of claim 31, wherein the control system detects an error when the packages received by the order consolidation station do not correspond with the at least one literature pack.

39. The system of claim 31, wherein the order consolidation station is configured to receive the packages and the at least one literature pack in the order sequence in which the at least one literature pack is stored with respect to the corresponding prescription orders.

40. The system of claim 39, wherein the control system detects an error when the packages are not received by the order consolidation station in the order sequence in which the at least one literature pack is stored.

41. A system for filling at least one prescription order, comprising:
a first transport means for receiving at least one bottle containing a number of pills individually counted as determined by a prescription order;
a second transport means for receiving at least one package containing prepackaged pharmaceutical products;
at least one identifier detector to detect at least one identification information associated with the at least one bottle, and to detect at least one other identification information associated with the at least one package;
at least one mechanism to place the at least one bottle into a container; and
an order consolidation means for receiving the at least one bottle from said first transport means and receiving the at least one package containing prepackaged pharmaceutical products from said second transport means; and
a control system that coordinates the first and second transport means and the at least one mechanism so that the at least one bottle and the at least one package are placed into a container when the at least one identification information and the at least one other identification information correspond to the at least one prescription order.

42. The system of claim 41, wherein the order consolidation means is further configured to receive at least one literature pack containing patient specific information relating to the at least one order and combine the at least one literature pack with the at least one bottle and the at least one package.

43. The system of claim 41, further comprising:
a package storage means, having an array of locations, for storing the at least one package into one of the array of locations; and a package dispense means for identifying the one of the array of locations, obtaining the at least one package from the one of the array of locations and providing the at least one package to the order consolidation means.

44. The system of claim 43, wherein the package dispense means includes a package label printer to print at least one label for the at least one package, wherein the label is printed with patient specific information.

45. The system of claim 44, the package dispense means further includes a device to affix the at least one label on the at least one package.

46. The system of claim 44, wherein the package dispense means further includes an error detection system configured to detect the label affixed on the at least one package and reject the at least one package and the label if an error is detected.

47. The system of claim 41, further comprising:
a bottle storage means, having an array of locations, for storing the at least one bottle into one of the array of locations; and
a bottle dispense means for identifying the one of the array of locations and dispensing the at least one bottle from the one of the array of the locations.

48. The system of claim 47, further comprising
a metal detector means for detecting the presence of a metallic substance in the at least one bottle, and for rejecting the at least one bottle if a metallic substance is detected therein.

49. The system of claim 47, wherein the bottle dispense means comprises:
a bottle buffer means for receiving the at least one bottle belonging to the one of at least one prescription order, wherein the bottle buffer means is disposed and configured to release all received at least one bottle.

50. The system of claim 41, wherein the system further comprises
a bagger means for opening the container to receive the at least one bottle and the at least one package into the container.

51. The system of claim 50, wherein the packager means comprises:
a printer means for printing an address or internal control information, wherein the bagger means is further configured for affixing the address or the internal control information on the container.

52. The system of claim 41, wherein the container comprises a bag.

53. A system for filling at least one prescription order, comprising:
a bottle handling means for storing and dispensing at least one bottle containing a number of pills as determined by the at least one prescription order;
a package handling means for storing and dispensing at least one package containing prepackaged pharmaceutical products;
at least one identifier detector to detect at least one identification information associated with each of the at least one bottle, and to detect at least one other identification information associated with each of the at least one package:
an order consolidation means for receiving the at least one bottle from a first transport system and receiving the at least one package from a second transport system; and
at least one mechanism for inserting the at least one bottle and the at least one package into a container when the at least one identification information and the at least one other identification information are detected corresponding to a common prescription order.

54. The system of claim 53, further comprising:
a literature handling means for printing and storing at least one literature pack containing patient specific information for the at least one prescription order,
wherein the order consolidation means receives the at least one literature pack and inserts the at least one literature pack into the container.

55. The system of claim 53, wherein the container comprises a bag.

56. A system for filling a plurality of prescription orders, comprising:
package handling means for storing a plurality of packages having at least one identification information and containing prepackaged pharmaceutical products;
literature handling means for printing and storing at least one literature pack relating to one of the plurality of prescription orders and coordinating the at least one literature pack with respect to corresponding prescription orders, the at least one literature pack having another identification information associated therewith;
a computer system configured to monitor the package handling and literature handling means and control the package handling means to dispense the plurality of packages in coordination with the dispensing of the at least one literature pack by the literature handling means; and
order consolidation means for receiving at least one prepackaged pharmaceutical product from a first transport system and at least one literature pack from a second transport system, said order consolidation means comprising a control system that enables at least one mechanism to place the at least one prepackaged pharmaceutical product having identification information corresponding to a particular prescription order and the at least one literature pack having another identification information corresponding to the same particular prescription order into at least one container corresponding to the same prescription order.

57. The system of claim 56, further comprising:
bottle handling means for storing a plurality of bottles each containing a number of pills as determined by a prescription order,
wherein the computer system is further configured to monitor the bottle handling means and cause the bottle handling means to dispense the bottles in coordination with the at least one literature pack, and
wherein the order consolidation means is further configured to receive the bottles associated with the prescription order and combine the bottles associated with the prescription order with the packages and literature packs.

58. The of claim 57, wherein the order consolidation means is configured to receive the bottles and the at least one literature pack in a same order sequence in which the at least one literature pack is stored with respect to the corresponding prescription orders and combine the bottles associated with the corresponding prescription orders with the combined packages and the at least one literature pack.

59. The system of claim 58, wherein the control system detects an error when the order consolidation means does not receive the bottles in the order sequence in which the at least one literature pack is stored.

60. The system of claim 56, wherein the order consolidation means is configured to receive the packages and the at least one literature pack in a same order sequence in which the at least one literature pack is stored with respect to the corresponding prescription orders.

61. The system of claim 60, wherein the control system detects an error when the order consolidation means does not receive the packages in the order sequence in which the at least one literature pack is stored.

62. A system for filling a plurality of prescription orders, comprising:
   a belt mechanism including a plurality of locations each of which is capable of carrying a pack of printed material corresponding with a prescription order;
   a bottle storage table including a plurality of tubes to store at least one bottle belonging to the prescription order;
   a first conveyor located to receive the at least one bottle from the bottle storage table and move the at least one bottle;
   means for receiving and holding the at least one bottle prior to placing the bottle into a container;
   a plurality of shelf locations, wherein each shelf location contains at least one package;
   a first robot mechanism having an end effector to obtain the at least one package and a means to release the at least one package;
   a second conveyor having a moving surface to move the at least one package received from the first robot mechanism;
   a second robot mechanism having an end effector to pick up the at least one package;
   a packager to open and hold the container; and
   a control system configured to coordinate the activities of: a) the belt mechanism to convey at least one pack of printed material and discharge the at least one pack into the container, b) the means for receiving and holding to obtain and dispose the at least one bottle into the container, and c) the second robot mechanism to obtain and dispose the at least one package into the container.

63. A system for filling at least one prescription order, comprising at least one order consolidation station configured to:
   receive from a first transport system at least one literature pack comprising patient specific information associated with a prescription order;
   receive from a second transport system at least one package containing prepackaged pharmaceutical products associated with the prescription order;
   detect at least one identification information associated with each of the at least one literature pack, and to detect at least another identification information associated with each of the at least one package;
   place the at least one package into a container; and
   coordinate the first and second transport systems and the at least one mechanism so that the at least one literature pack and the at least one package are placed in a container when the at least one identification information associated with the at least one literature pack and the at least another identification information associated with the at least one package correspond to the at least one prescription order, to thereby fill the at least one prescription order.

64. The system of claim 63, wherein the at least one order consolidation station is further configured to receive at least one bottle containing a number of counted pills corresponding to the prescription order, and combine the at least one literature pack with the at least one bottle and the at least one package.

65. The system of claim 64, further comprising:
   a bottle storage device having an array of locations and configured to store the at least one bottle into one of the array of locations; and
   a bottle dispenser configured to identify the one of the array of locations and dispense the at least one bottle from the one of the array of the locations.

66. The system of claim 65, further comprising
   a metal detector configured to detect a metallic substance in the at least one bottle, wherein the bottle is transported to a quality assurance area if a metallic substance is detected.

67. The system of claim 65, further comprising
   a bottle buffer configured to receive the at least one bottle belonging to the one of at least one prescription order, wherein the bottle buffer is disposed and configured to release the received at least one bottle from said storage device.

68. The system of claim 63, further comprising:
   a package storage device having an array of locations and configured to store the at least one package into one of the array of locations; and
   a package dispenser configured to identify the one of the array of locations, obtain the at least one package from the one of the array of locations and provide the at least one package to the order consolidation station.

69. The system of claim 68, wherein the package dispenser further includes a package label printer to print at least one label for the at least one package, wherein the label is printed with patient specific information.

70. The system of claim 69, wherein the package dispenser further includes a labeler to affix the at least one label on the at least one package.

71. The system of claim 69, wherein the control system comprises an error detection system configured to detect the label affixed on the at least one package and reject the at least one package and the label if an error is detected.

72. The system of claim 63, further comprising:
   a package storage device having an array of locations and configured to store a plurality of packages into the array of locations and store the at least one package into one of the array of locations; and
   a package dispenser configured to identify the one of the array of locations, obtain the at least one package from the one of the array of locations and provide the at least one package to the order consolidation station.

73. The system of claim 63, further comprising a packager configured to open a container to receive the at least one literature pack and the at least one package.

74. The system of claim 73, wherein the packager comprises:
   a printer configured to print an address or internal control information, and wherein the packager is further configured to affix the address or the internal control information on the container.

75. The system of claim 63, wherein the container comprises a bag.

* * * * *